(12) United States Patent
Huang et al.

(10) Patent No.: US 8,846,664 B2
(45) Date of Patent: Sep. 30, 2014

(54) PYRAZINOPYRAZINES AND DERIVATIVES AS KINASE INHIBITORS

(75) Inventors: Wei-Sheng Huang, Acton, MA (US); R. Mathew Thomas, Sharon, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 297 days.

(21) Appl. No.: 12/998,634

(22) PCT Filed: Nov. 12, 2009

(86) PCT No.: PCT/US2009/006057
§ 371 (c)(1),
(2), (4) Date: Aug. 12, 2011

(87) PCT Pub. No.: WO2010/056311
PCT Pub. Date: May 20, 2010

(65) Prior Publication Data
US 2011/0288078 A1    Nov. 24, 2011

Related U.S. Application Data

(60) Provisional application No. 61/198,995, filed on Nov. 12, 2008.

(51) Int. Cl.
| | |
|---|---|
| A01N 43/62 | (2006.01) |
| A61K 31/55 | (2006.01) |
| A61K 31/497 | (2006.01) |
| C07D 491/00 | (2006.01) |
| C07D 513/00 | (2006.01) |
| C07D 515/00 | (2006.01) |
| C07D 471/00 | (2006.01) |
| C07D 487/00 | (2006.01) |
| C07D 495/00 | (2006.01) |
| C07D 497/00 | (2006.01) |
| A61K 9/48 | (2006.01) |
| C07D 471/04 | (2006.01) |
| A61K 9/28 | (2006.01) |
| A61K 47/10 | (2006.01) |
| A61K 9/20 | (2006.01) |
| A61K 9/00 | (2006.01) |
| C07D 487/04 | (2006.01) |

(52) U.S. Cl.
CPC ............ C07D 471/04 (2013.01); A61K 9/4858 (2013.01); A61K 9/2866 (2013.01); A61K 47/10 (2013.01); A61K 9/2018 (2013.01); A61K 9/0019 (2013.01); A61K 9/008 (2013.01); C07D 487/04 (2013.01)
USPC ....... 514/221; 514/252.11; 540/568; 544/350

(58) Field of Classification Search
CPC .......................... A61K 31/4985; C07D 403/04
USPC ..................... 514/221, 249, 252.11; 540/568; 544/350
See application file for complete search history.

(56) References Cited

U.S. PATENT DOCUMENTS

| | | | |
|---|---|---|---|
| 6,635,641 B2 | 10/2003 | Bender et al. | |
| 6,713,462 B2 | 3/2004 | Metcalf et al. | |
| 7,115,589 B2 | 10/2006 | Weigele et al. | |
| 7,132,427 B2 | 11/2006 | Wang et al. | |
| 7,238,679 B2 | 7/2007 | Keenan et al. | |
| 7,776,869 B2 | 8/2010 | Chaffee et al. | |
| 8,039,479 B2 | 10/2011 | Mechellys et al. | |
| 8,071,609 B2 | 12/2011 | Wang et al. | |
| 8,114,874 B2 | 2/2012 | Zou et al. | |
| 8,278,307 B2 | 10/2012 | Shakespeare et al. | |
| 2003/0207885 A1 | 11/2003 | Hutchison et al. | |
| 2004/0058903 A1 | 3/2004 | Takasugi et al. | |
| 2004/0092747 A1 | 5/2004 | Bender et al. | |
| 2005/0054614 A1 | 3/2005 | Diacovo et al. | |
| 2005/0159446 A1 | 7/2005 | Chew et al. | |
| 2005/0267304 A1 | 12/2005 | Cox et al. | |
| 2006/0217380 A1 | 9/2006 | Chaffee et al. | |
| 2007/0191376 A1 | 8/2007 | Zou et al. | |
| 2008/0027076 A1 | 1/2008 | Jones et al. | |
| 2008/0108608 A1 | 5/2008 | Jones et al. | |
| 2008/0153838 A1 | 6/2008 | Jones et al. | |
| 2008/0194552 A1 | 8/2008 | Jones et al. | |
| 2009/0149471 A1 | 6/2009 | Shakespeare et al. | |
| 2011/0112110 A1 | 5/2011 | Gambacorti Passerini et al. | |

FOREIGN PATENT DOCUMENTS

| | | |
|---|---|---|
| EP | 1132387 | 9/2001 |
| EP | 2123654 | 11/2009 |
| WO | WO 98/05335 | 2/1998 |
| WO | WO 98/43960 | 10/1998 |
| WO | WO 00/26202 | 5/2000 |

(Continued)

OTHER PUBLICATIONS

International Search Report for PCT/US09/06057 dated Mar. 11, 2010.

(Continued)

*Primary Examiner* — Sarah Pihonak
(74) *Attorney, Agent, or Firm* — David L. Berstein; Gretchen S. Peterson

(57) ABSTRACT

This invention relates to compounds of the general formula: in which the variable groups are as defined herein, and to their preparation and use.

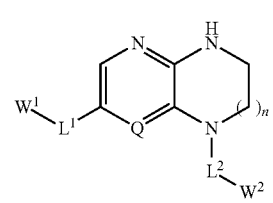

(I)

34 Claims, No Drawings

(56) References Cited

FOREIGN PATENT DOCUMENTS

| | | |
|---|---|---|
| WO | WO 00/43384 | 7/2000 |
| WO | WO 00/49018 | 8/2000 |
| WO | WO 01/44258 | 6/2001 |
| WO | WO 01/44260 | 6/2001 |
| WO | WO 01/53274 | 7/2001 |
| WO | WO 01/81311 | 11/2001 |
| WO | WO 02/24682 | 3/2002 |
| WO | WO 02/24683 | 3/2002 |
| WO | WO 02/24686 | 3/2002 |
| WO | WO 02/24687 | 3/2002 |
| WO | WO 02/074752 | 9/2002 |
| WO | WO 03/000011 | 1/2003 |
| WO | WO 03/000187 | 1/2003 |
| WO | WO 03/000270 | 1/2003 |
| WO | WO 2004/018428 | 3/2004 |
| WO | WO 2004/058776 | 7/2004 |
| WO | WO 2004/072025 | 8/2004 |
| WO | WO 2005/009348 | 2/2005 |
| WO | WO 2005/030705 | 4/2005 |
| WO | WO 2005/060969 | 7/2005 |
| WO | WO 2005/060970 | 7/2005 |
| WO | WO 2005/097773 | 10/2005 |
| WO | WO 2006/044823 | 4/2006 |
| WO | WO 2006/082404 | 8/2006 |
| WO | WO 2006/103449 | 10/2006 |
| WO | WO 2007/013673 | 2/2007 |
| WO | WO 2007/021937 | 2/2007 |
| WO | WO 2007/075869 | 7/2007 |
| WO | WO 2007/120339 | 10/2007 |
| WO | WO 2007/130468 | 11/2007 |
| WO | WO 2007/133560 | 11/2007 |
| WO | WO 2007130468 A2 * | 11/2007 |
| WO | WO 2008/051493 | 5/2008 |
| WO | WO 2009/143389 | 11/2009 |
| WO | WO 2010/062571 | 6/2010 |
| WO | WO 2011/053518 | 5/2011 |

OTHER PUBLICATIONS

Liao, "Molecular Recognition . . . and Selective Kinase Inhibitors", Jrnl of Medicinal Chemistry, 2007, pp. 409-424, vol. 50.

EP Supplementary Search Report dated Oct. 5, 2012 for EP Appl. No. 09826414.6.

Acevedo et al, "Inducible FGFR-1 Activiation Leads to Irreversible Prostate Adenocarcinoma and an Epithelial-to-Mesenchymal Transition", Cancer Cell, 2007, pp. 559-571,vol. 12.

Boesen et al, "Preparation of N-(alk-1-enyl) nucleobase compounds by Horner and Horner-Wadsworth-Emmons reactions", Jrnl of Chem. Soc., Perkin Trans 1, 2000, pp. 2015-2021.

Bonafoux et al, "Inhibition of IKK-2 by 2-[(aminocarbonyl)amino]-5-acetylenyl-3-thiophenecarboxamides", Bioorganic & Medicinal Chemistry Letters, 2005, pp. 2870-2875, vol. 15.

Boschelli et al, "Synthesis and SRC Kinase Inhibitory Activity of a Series of 4-Phenylamino-3-quinolinecarbonitriles", J. Med. Chem., 2001, pp. 822-833, vol. 44.

Camerel et al., "New Platforms Integrating Ethynyl-Grafted Modules for Organogels and Mesomorphic Superstructures", Organic Letters, 2004, pp. 4171-4174, vol. 6, No. 23.

Carmi et al., "Novel Irreversible Epidermal Growth Factor Receptor . . . Chemical Modulation of the Cysteine-Trap Portion", J. Med. Chem., 2010, pp. 2038-2050, vol. 53.

Cee, Victor J. et al., "Alkynylpyrimidiine Amide Derivatives as Potent, Selective, and Orally Active Inhibitors of Tie-2 Kinase", J. Med. Chem. 2007, pp. 627-640, vol. 50.

Cortes et al., "A Phase 1 Trial of Oral Ponatinib . . . Clinical Response Findings", American Society of Hematology (ASH), 2010, Abstract No. 210.

Dalgarno et al., "Structural Basis of Src Tyrosine Kinase Inhibition . . . Trisubstituted Purine-based Compounds", Chem. Biol. Drug Des., 2006, pp. 46-57, vol. 67.

Database CA on STN, Chemical Abstracts, (Columbus, OH, US), No. 132:35620, Wissner, abstract, US Patent 6,002,008, Dec. 1999.

Database CA on STN, Chemical Abstracts, (Columbus, OH US), No. 134:100834, Wang, abstract, Bioorganic & Medicinal Chem Letters, 2000, pp. 2477-2480, vol. 10.

Database CA on STN, Chemical Abstracts, (Columbus, OH US), No. 129:302564, Wissner, abstract, WO9843960, Oct. 1998.

Deng et al., "Broad spectrum alkynyl inhibitors of T315I Bcr-Abl", Bioorganic & Medicinal Chem. Ltrs., 2010, pp. 4196-4200, vol. 20.

Dorwald, "Side Reactions in Organic Synthesis: A Guide to Successful Synthesis Design", Weinheim: Wiley-Vch Verlag GmbH & Co. KGaA, 2005, Preface.

Dubinina et al, "Novel 5,7-disubstituted 6-amino- . . . with antiproliferative activity", European Journal of Medicinal Chemistry, 2006, pp. 727-737, vol. 41.

Eck et al., "Structural and Mechanistic Underpinnings of the . . . of EGFR Mutations in Non-small Cell Lung Cancer", Biochimica et Biophysica Acta, 2010, pp. 559-566.

Finn, "Targeting Src in Breast Cancer", Annals of Oncology, 2008, pp. 1379-1386, vol. 19(8).

Gozgit et al., " the Orally Active Kinase Inhibitor AP24534 . . . In Multiple Cancer Models", American Assoc. for Cancer Research (AACR), 2009, Poster Abstract No. 1739.

Gozgit et al., "Ponatinib (AP24534), . . . Distinct Mechanisms of Activation" American Assoc. for Cancer Research (AACR), 2011, Poster Abstract No. 3560.

Gozgit et al., "Potent Activity of Ponatinib (AP24534) . . . and Other Hematologic Malignancies", Molecular Cancer Theraoeutics, 2011, pp. 1028-1035, vol. 10(6).

Grande et al., "Targeting Oncogenic ALK: A Promising Strategy for Cancer Treatment", Molecular Cancer Therapeutics, 2011, pp. 569-579 + 1529, vol. 10.

Gundla et al., "Discovery of Novel Small-Molecule Inhibitors . . . Receptor-2: Combined Ligand and Target-Based Approach", J. Med. Chem., 2008, pp. 3367-3377, vol. 51.

Hiscox et al, "Src as a therapeutic target in anti-hormone/anti growth factor-resistant breast cancer", Endocrine-Related Cancer, 2006, pp. S53-S59, vol. 13.

Hockova et al, "Regioselective Preparation of N7- and N9-Alkyl Derivatives . . . Acyclic Nucleoside Analogues", Eur. J. Org. Chem.,1999, pp. 2675-2682.

Huang et al, "Facile Synthesis of . . . and aryl halides", Tetrahedron Letters, 2007, pp. 7388-7391, vol. 48, No. 41.

Huang et al., "Discovery of 3[2-(Imidazo[1,2-b]pyridazin-3-yl]-4- . . . Including the T315I Gatekeeper Mutant", J. Med. Chem., 2010, pp. 4701-4719, vol. 53.

Iso et al., "Synthesis and Structure . . . Antagonists; Search for Cocaine Medications", J. Med. Chem., 2006, pp. 1080-1100, vol. 49.

Jordan, "Tamoxifen: A Most Unlikely Pioneering Medicine", Nature Reviews: Drug Discovery, 2003, pp. 205-213, vol. 2.

Joshi et al, "Ynamines Derived from . . . and Biological Activity", J. of the Chem. Soc., Chem Commun., 1992, pp. 513-514, vol. 1992.

Kendall et al., "Vascular Endothelial Growth Factor Receptor . . . Loop Tyrosine Residues", Journal of Biological Chemistry, 1999, pp. 6453-6460, vol. 274, No. 10.

Klutchko et al., "Tyrosine Kinase Inhibitors. 19. 6-Alkynamides . . . of the erbB Family of Tyrosine Kinase Receptors", J. Med. Chem., 2006, pp. 1475-1485, vol. 49.

Koziczak et al., "Blocking of FGFR signaling inhibits breast cancer cell proliferation through downregulatoin of D-type cyclins", Oncogene, 2004, pp. 3501-3508, vol. 23.

McMahon, "VEGF Receptor Signaling in Tumor Angiogenesis", The Oncologist, 2000, pp. 3-10, 5(suppl 1).

Mishani et al., "High-Affinity Epidermal Growth Factor Receptor (EGFR) . . . Agent Candidates of EGFR Overexpessing Tumors", J. Med. Chem., 2005, pp. 5337-5348, vol. 48.

O'Hare et al., "AP24534, a Pan-BRC-ABL Inhibitor for Chronic Myeloid Leukemia, . . . Mutation-Based Resistance", Cancer Cell, 2009, pp. 401-412, vol. 16.

O'Hare et al., "AP24534, a Pan-BRC-ABL Inhibitor for Chronic Myeloid Leukemia, . . . Mutation-Based Resistance", Cancer Cell, 2009, Supplemental Data, vol. 16.

(56) References Cited

OTHER PUBLICATIONS

Okamoto et al., "Identification of c-Src . . . Resistance to c-Src Inhibition", Molecular Cancer Therapeutics, 2010, pp. 1188-1197, vol. 9(5).

Pinedo et al., "Translational Research: The Role of VEGF in Tumor Angiogenesis", 2000, The Oncologist, pp. 1-2, 5 (suppl 1).

Porter et al, "Discovery of 4-azaindoles as novel inhibitors of c-Met kinase", Bioorganic & Medicinal Chemistry Letters, 2009, pp. 2780-2784, vol. 19.

Rivera et al., "Pharmacodynamics (PD) . . . Chronic Myeloid Leukemia (CML) and Hematologic Malignancies" European School of Haematology (ESH), 2010, Poster Abstract No. 42.

Smaill et al., "Tyrosine Kinase Inhibitors. 18. 6-Substituted . . . of the Epidermal Growth Factor Receptor", J. Med. Chem., 2001, pp. 429-440, vol. 44.

Talpaz et al., "Phase 1 Trial of AP24534 . . . (CML) and Hematologic Malignancies", American Society of Clinical Oncology (ASCO), 2010, Poster Abstract No. 6511.

Talpaz et al., "Ponatinib in Patients . . . Phase 1 Study in Hematologic Malignancies", American Society of Clinical Oncology (ASCO), 2011, Poster Abstract No. 6518.

Traxler, "Review: Onocolgic, Endocrine, Metabolic Protein Tyrosine Kinase Inhibitors in Cancer Treatment", Exp.Opin. Ther. Patents, 1997, pp. 571-588, vol. 7(6).

Vippagunta et al., "Crystalline Solids", Advanced Drug Delivery Reviews, 2001, pp. 3-26, vol. 48.

Wang et al., "Inhibitors of Src Tyrosine Kinase . . . of 4-Anilino-3cyanoquinolines and 4-Anilinoquinazolines", Bioorganic & Medicinal Chem. Ltrs, 2000, pp. 2477-2480, vol. 10.

Zhou et al., Tumor Antiogenesis Correlated with bFGF and FGFR-1 in Lung Cancer, Chinese-German Journal of Clinical Oncology, 2005, pp. 93-98, vol. 4.

Zhou et al., "Structural Analysis of DFG-in and DFG-out Dual Src-Abl Inhibitors Sharing a Common Vinyl Purine Template", 2010, Chem. Biol. Drug Des., pp. 18-28, vol. 75.

Zhou et al., "Structural Mechanism . . . Overcoming Kinase Inhibitor Resistance", Chem Biol Drug Des, 2011, pp. 1-11, vol. 77.

Zhu et al., "Structural Analysis . . . T315I Gatekeeper Mutation", American Assoc. for Cancer Research (AACR), 2010, Poster Abstract No. 2671.

EP Suppl. Search Report dated Feb. 10, 2010 for EP Appl. 06845939.5.

EP Suppl. Search Report dated Aug. 16, 2010 for EP Appl. 06813381.8.

EP Suppl. Search Report dated Jan. 21, 2011 for EP Appl. 07756231.2.

EP Suppl. Search Report dated May 31, 2011 for EP Appl. 07756233.8.

Int'l Search Report dated May 18, 2007 for PCT/US06/31382.
Int'l Search Report dated Sep. 28, 2007 for PCT/US06/48758.
Int'l Search Report dated Sep. 24, 2008 for PCT/US07/11134.
Int'l Search Report dated Aug. 5, 2008 for PCT/US07/11136.

\* cited by examiner

PYRAZINOPYRAZINES AND DERIVATIVES AS KINASE INHIBITORS

CROSS-REFERENCE TO RELATED APPLICATIONS

The present application claims benefit under 35 U.S.C. §371 of International Application No. PCT/US2009/006057 (published PCT application no. WO 2010/056311), filed Nov. 12, 2009, which claims priority to 35 U.S.C. §119(e) to U.S. Provisional Patent Application No. 61/198,995, filed Nov. 12, 2008, the entire contents of which are hereby incorporated by reference.

BACKGROUND OF THE INVENTION

The protein kinases represent a large family of proteins which play a central role in the regulation of a wide variety of cellular processes and maintain control over cellular function. A partial, non limiting, list of such kinases includes ALK, abl, Akt, bcr-abl, Blk, Brk, c-kit, c-met, c-src, CDK1, CDK2, CDK3, CDK4, CDK5, CDK6, CDK7, CDK8, CDK9, CDK10, bRaf, cRaf1, CSK, EGFR, ErbB2, ErbB3, ErbB4, Erk, Pak, fes, FGFR1, FGFR2, FGFR3, FGFR4, FGFR5, Fgr, flt-1, flt-3, Fps, Frk, Fyn, Hck, IGF-1R, INS-R, Jak1, Jak2, Jak3, KDR, Lck, Lyn, FAK, MEK, p38, PDGFR, PIK, PKC, PYK2, ros, tie, tie2, Pim-1, Pl3k, TRK and Zap70. Abnormal protein kinase activity has been related to several disorders, ranging from non-life threatening diseases such as psoriasis to extremely serious diseases such as cancers.

In view of this large number of protein kinases and the multitude of protein kinase-related diseases, there is an ever-existing need to provide new classes of compounds with increased selectivity that are useful as protein kinase inhibitors and therefore useful in the treatment of protein tyrosine-kinase related diseases.

This invention concerns a new family of pyrazinopyrazine compounds and their use in treating cancers and other diseases.

DESCRIPTION OF THE INVENTION

1. General Description of Compounds of the Invention

The compounds of this invention have a broad range of useful biological and pharmacological activities, permitting their use in pharmaceutical compositions and methods for treating cancer (including lymphoma, solid tumors and leukemia among other cancers), including, also among others, advanced cases and cases which are resistant or refractory to one or more other treatments.

Included are compounds of Formula I, and tautomers and pharmaceutically acceptable salts and solvate thereof:

A compound of Formula I, a tautomer, a pharmaceutically acceptable salt and a solvate thereof:

Formula I

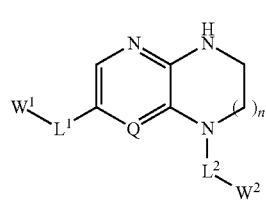

wherein $W^1$ represents an aryl, a 3- to 8-membered carbocyclyl, a 5-, 6- or 7-membered heterocyclic or heteroaryl ring comprising carbon atoms and 1-4 heteroatoms independently selected from O, N, P(O) and S(O)$_r$ and $W^1$ is optionally substituted with 1-5 $R^a$ groups;

$W^2$ represents an aryl or a 5- or 6-membered heteroaryl ring comprising carbon atoms and 1-3 heteroatoms independently selected from O, N, P(O) and S(O)$_r$ and $W^2$ is optionally substituted with 1-5 $R^b$ groups;

Q is N or CR$^c$;

$L^1$ and $L^2$ are independently selected from the group consisting of a bond, $C_{1-6}$-alkyl, O—$C_{0-6}$-alkyl, NR$^1$—$C_{0-6}$-alkyl, C(O)NR$^1$—$C_{0-6}$-alkyl, NR$^1$C(O)—$C_{0-6}$-alkyl, $C_{2-6}$-alkenyl, $C_{2-6}$-alkynyl, $C_{0-6}$alkyl-S(O)$_r$, $C_{0-6}$alkyl-S(O)$_2$NR$^1$, $C_{0-6}$alkyl-NR$^1$S(O)$_2$, C(O)—$C_{0-6}$alkyl, OC(O)NR$^1$—$C_{0-6}$-alkyl, NR$^1$C(O)O—$C_{0-6}$-alkyl, NR$^1$C(O)NR$^1$—$C_{0-6}$-alkyl; and the linkers $L^1$ and $L^2$ can be included in either direction;

$R^a$ and $R^b$ are independently selected from the group consisting of halo, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, C(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, YP(=O)(YR$^3$)(YR$^3$), —Si(R$^3$)$_3$, —NR$^1$SO$_2$R$^2$, —S(O)$_r$R$^2$, —SO$_2$NR$^1$R$^2$ and —NR$^1$SO$_2$NR$^1$R$^2$; alternatively two adjacent $R^a$ or two adjacent $R^b$ can form with the atoms to which they are attached, a 5-, 6- or 7-membered saturated, partially saturated or unsaturated ring, which can be optionally substituted and which contains 0-3 heteroatoms selected from N, O, P(O) and S(O)$_r$;

$R^c$ is selected from the group consisting of halo, —R$^3$, —OR$^2$ and —SR$^2$;

wherein each Y is independently a bond, —O—, —S— or —NR$^1$—;

r is 0, 1 or 2;

n is 1 or 2;

each occurrence of $R^1$ and $R^2$ is independently selected from H, alkyl, alkenyl, alkynyl, cycloalkyl, cycloalkenyl, cycloalkynyl, aryl, heterocyclic and heteroaryl;

each occurrence of $R^3$ is independently selected from alkyl, alkenyl, alkynyl, cycloalkyl, cycloalkenyl, cycloalkynyl, aryl, heterocyclic and heteroaryl;

alternatively, each NR$^1$R$^2$ moiety may be a 5-, 6- or 7-membered saturated, partially saturated or unsaturated ring, which can be optionally substituted and which contains 0-2 additional heteroatoms selected from N, O, P(O) and S(O)$_r$; and each of the foregoing alkyl, alkenyl, alkynyl, cycloalkyl, cycloalkenyl, cycloalkynyl, aryl, heteroaryl and heterocyclic moiety is optionally substituted.

The foregoing definitions are further elaborated upon and exemplified below and apply to all subsequent occurrences except to the extent otherwise specified.

2. Featured Classes of Compounds and their Use, Generally

One class of compounds which is of special interest for use in this invention are compounds of Formula I, as described above in Part 1, in which Q is N. This class is illustrated by compounds of formula IA:

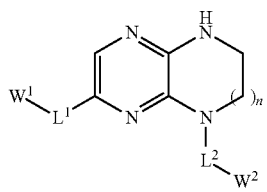

Formula IA

A subclass of interest include compound of formula IA in which n is 1.

Another subclass of interest includes compounds of formula IA in which n is 2.

Another subclass of interest includes compounds of Formula IA in which $W^1$ is an aryl.

Another subclass of interest includes compounds of Formula IA in which $W^1$ is a 5- or 6-membered heteroaryl.

Another subclass of interest includes compounds of Formula IA in which $W^1$ is a 5-, 6-, or 7-membered heterocyclyl.

Another subclass of interest includes compounds of Formula IA in which $W^1$ is a 3- to 8-membered carbocyclyl.

Another class of compounds which is of special interest for use in this invention are compounds of Formula I, as described above, in which Q is $CR^c$.

This class is illustrated by compounds of Formula IB:

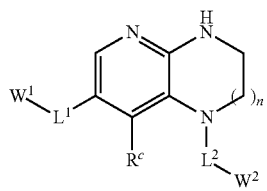

Formula IB

A subclass of interest include compound of formula IB in which n is 1.

Another subclass of interest includes compounds of formula IB in which n is 2.

Another subclass of interest includes compounds of Formula IB in which $W^1$ is an aryl.

Another subclass of interest includes compounds of Formula IB in which $W^1$ is a 5- or 6-membered heteroaryl.

Another subclass of interest includes compounds of Formula IB in which $W^1$ is a 5-, 6-, or 7-membered heterocyclyl.

Another subclass of interest includes compounds of Formula IB in which $W^1$ is a 3- to 8-membered carbocyclyl.

Another subclass of interest includes compound of Formula IB and all previous subclasses in which $R^c$ is halo or lower alkyl (i.e. Methyl, Ethyl).

For the previously described classes and subclasses of compounds described above $R^a$, $R^b$, $L^2$, $L^1$, $W^2$ are defined above in part 1.

One class of compounds of special interest are compounds of Formula IA or IB in which $L^1$ is $NR^1C_{0-6}$-alkyl.

Illustrative examples of this class are compounds of the following types in which n is 1:

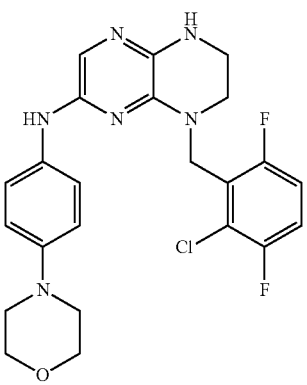

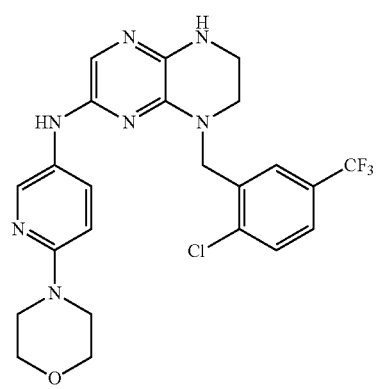

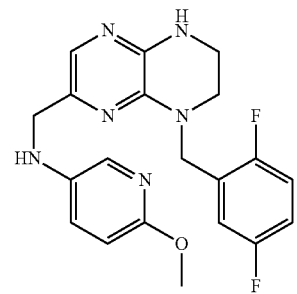

Other illustrative examples of this class are compounds of the following types in which n is 2:

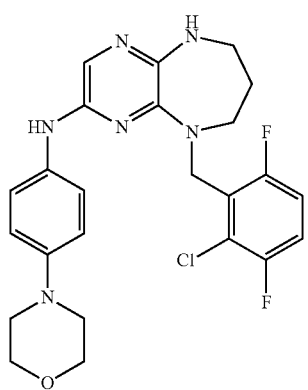

-continued

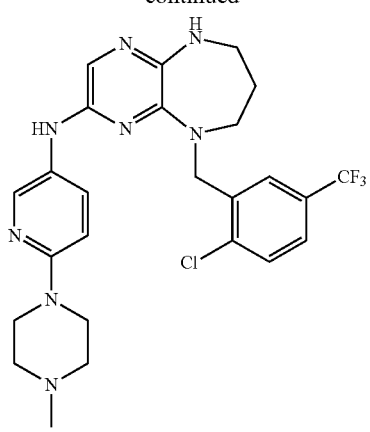

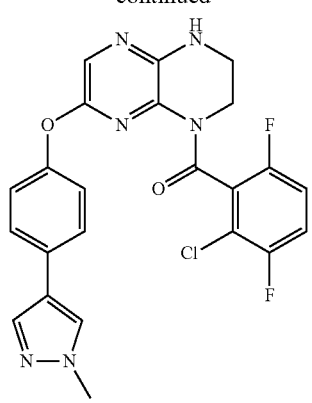

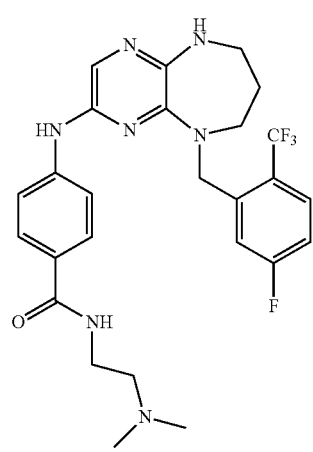

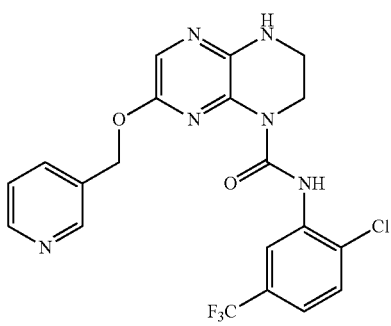

Other illustrative examples of this class are compounds of the following types in which n is 2:

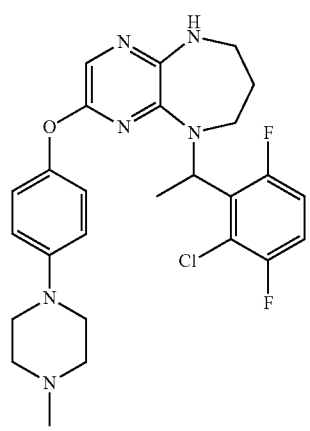

In another embodiment, this invention relates to compounds of Formula IA or LB as described above, in which $L^1$ is O—$C_{0-6}$-alkyl. Of special interest are compounds of this class in which $W^1$ and $W^2$ are aryl or heteroaryl.

Illustrative examples of this class are compounds of the following types in which n is 1:

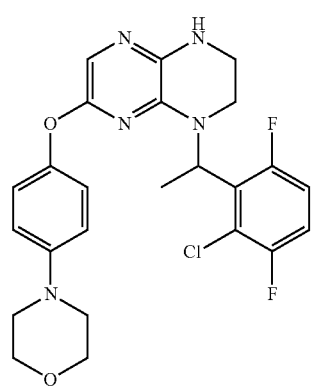

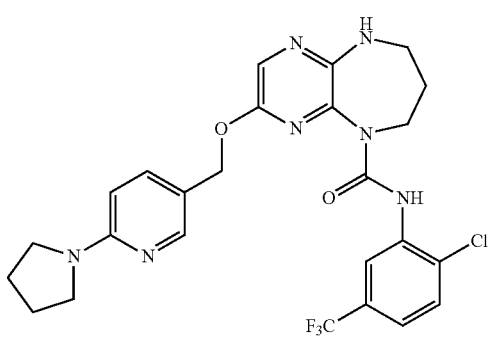

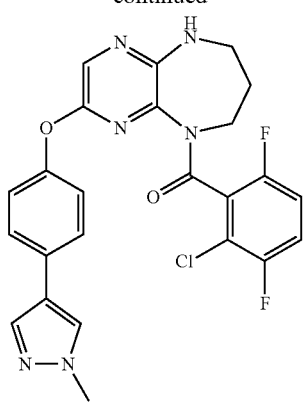

In another embodiment, this invention relates to compounds of Formula IA or IB as described above, in which $L^1$ is S—$C_{0-6}$-alkyl.

Illustrative examples of this class are compounds of the following types in which n is 1:

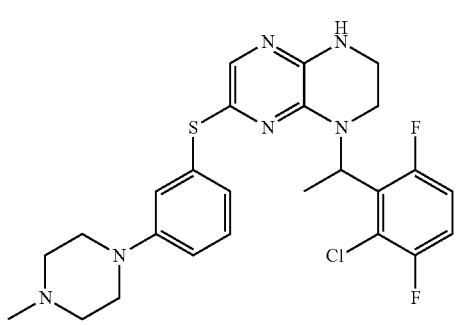

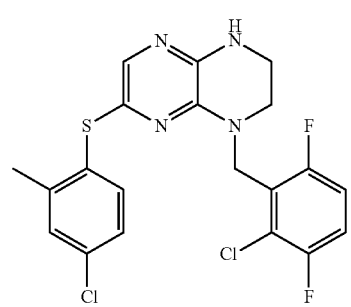

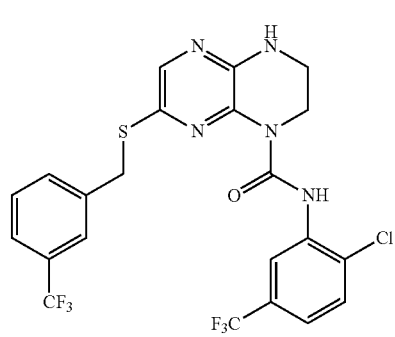

Other illustrative examples of this class are compounds of the following types in which n is 2:

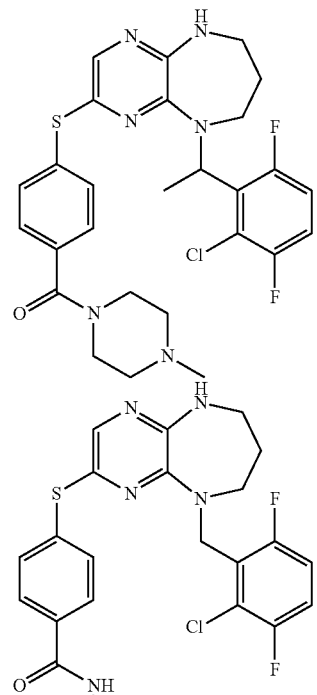

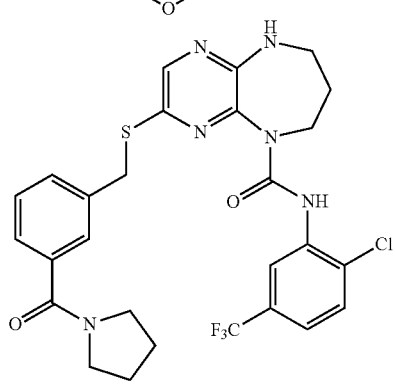

In another embodiment, this invention relates to compounds of Formula IA or IB as described above, in which $L^1$ is a bond. This is illustrated by compound of the following formula IC:

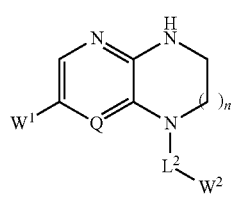

Formula IC

Of further interest are compounds of formula IC in which Q is N.

Of other interest are compounds of formula IC in which Q is $CR^c$, in which for example $R^c$ is lower alkyl or halo.

In one aspect of the above embodiment are compounds of Formula IC in which n is 1. In another aspect of this embodiment are compounds of formula IC in which n is 2.

Of special interest are compounds of formula IC in which $L^2$ is $C_{0-6}$alkyl. Of further interest are compounds of this class in which $L^2$ is $CHCH_3$ or $CH_2$. Of further interest are compounds of this class and subclass in which $W^1$ and $W^2$ are independently chosen from aryl and heteroaryl.

Illustrative examples of this class are compounds of formula IC of the following types in which n is 1:

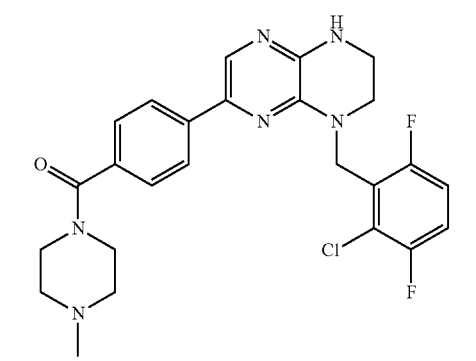

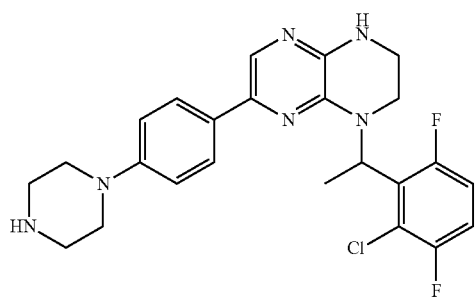

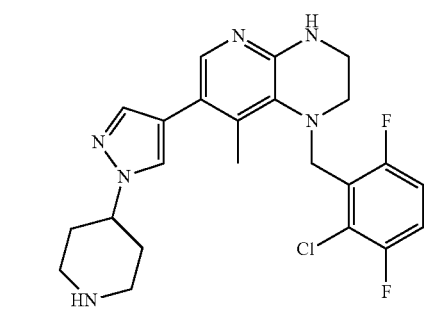

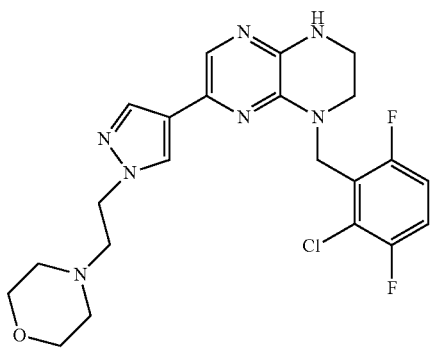

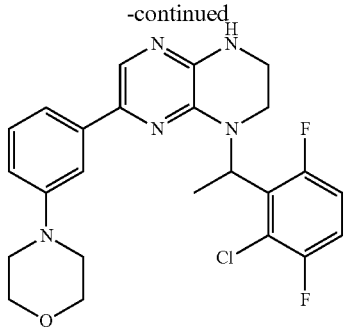

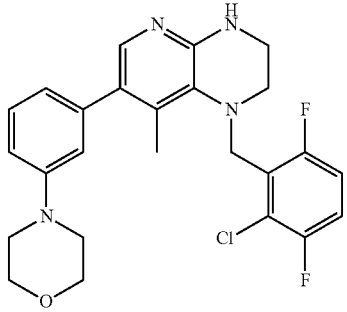

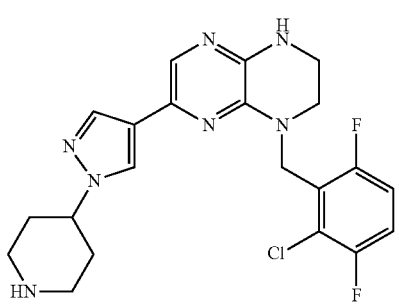

Other illustrative examples of this class are compounds of formula IC of the following types in which n is 2:

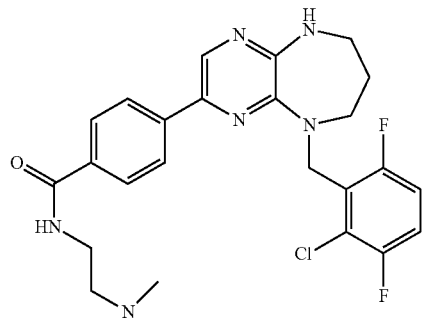

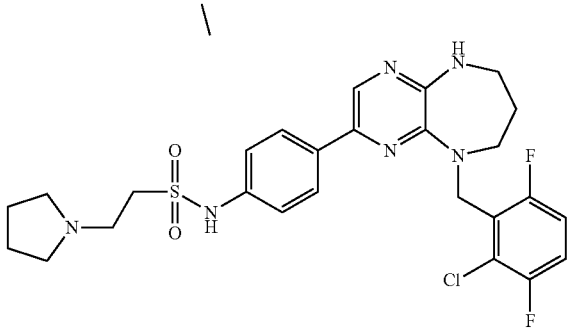

-continued

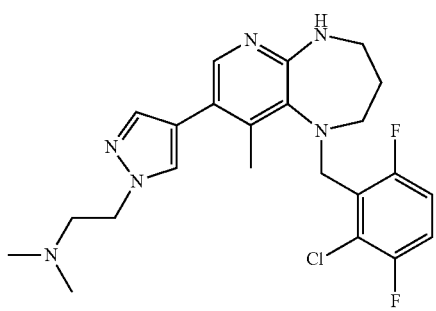

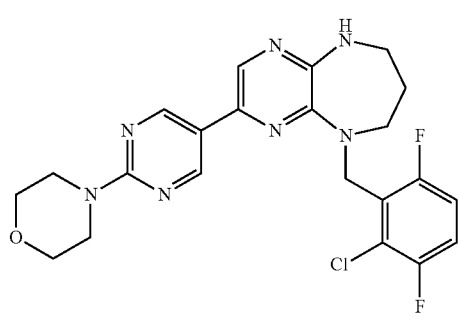

In some embodiment, this invention relates to compounds of Formulae IA or IB as described above, in which $L^1$ is $C(O)C_{0-6}$alkyl. Of further interest are compounds of this class in which $W^1$ is a 5- to 7-membered heterocyclyl. Illustrative examples of this class are compounds of the following types:

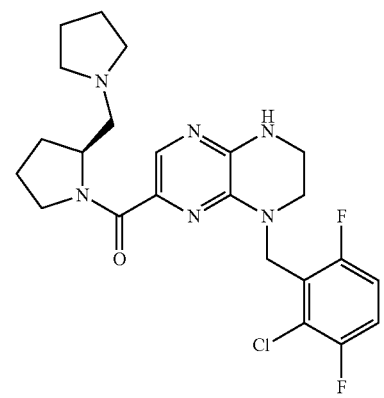

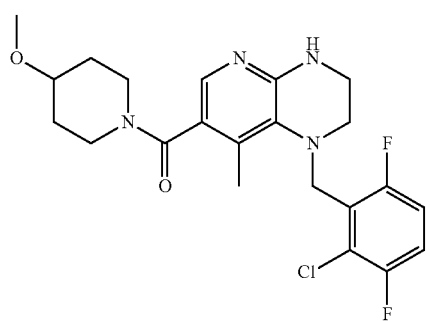

-continued

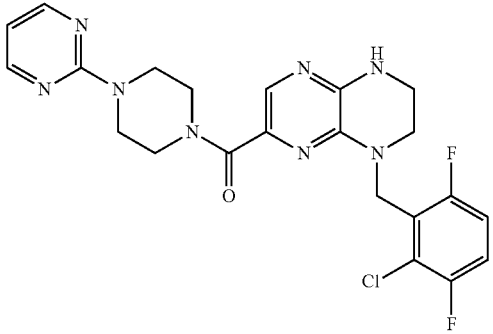

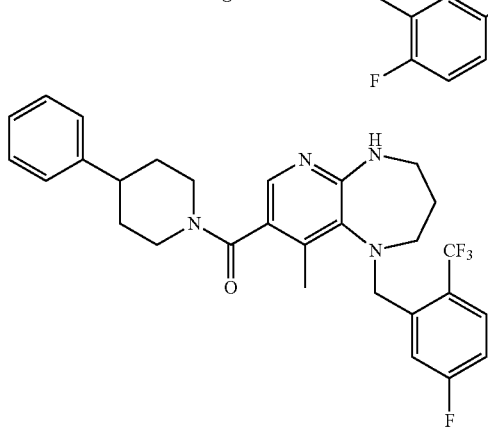

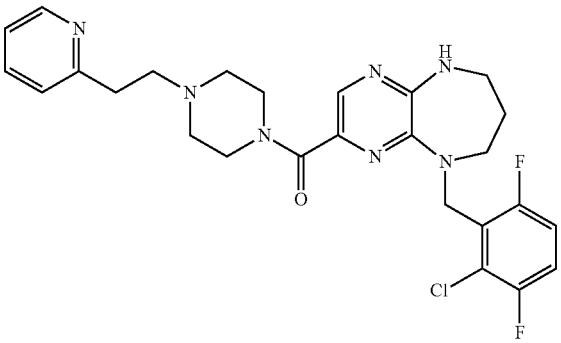 [SMILES: O=C(c1cnc2c(n1)N(Cc1c(F)ccc(F)c1Cl)CCCN2)N1CCN(CCc2ccccn2)CC1]

In some embodiment, this invention relates to compounds of Formulae IA or IB as described above, in which $L^1$ is $C(O)NHC_{0-6}$alkyl. Illustrative examples of this class are compounds of the following types:

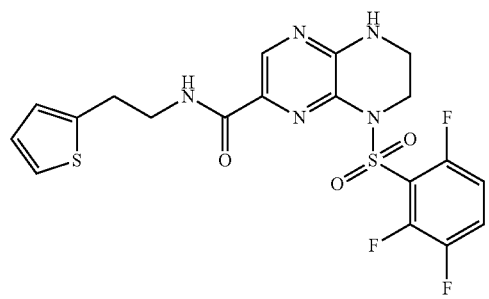

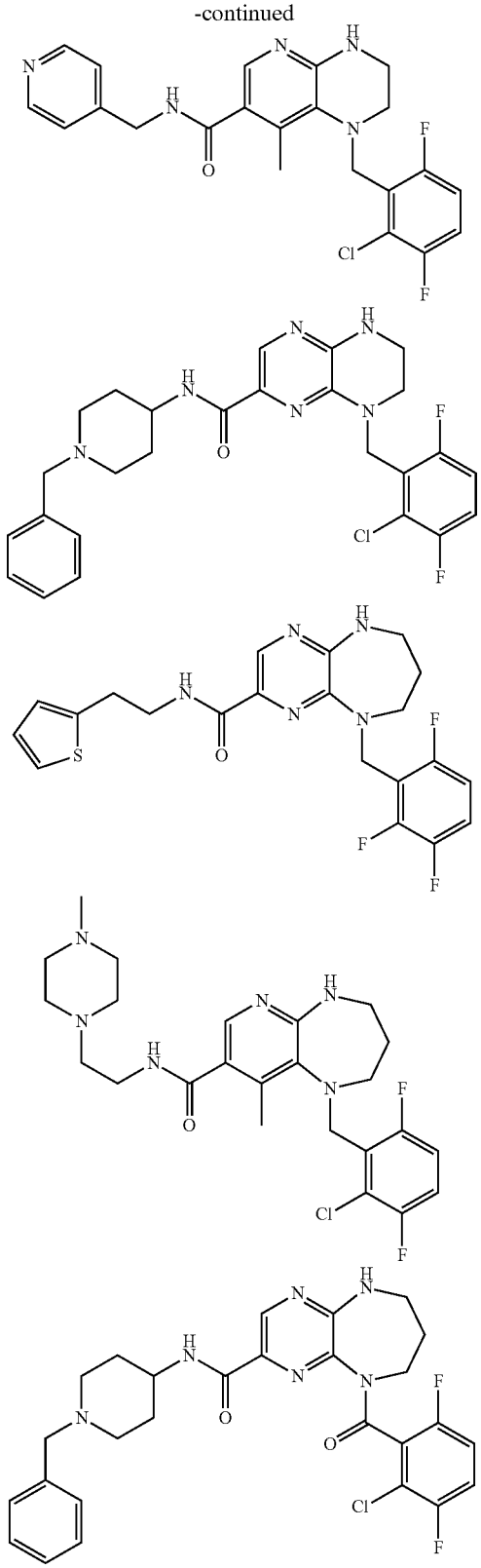

In some embodiment, this invention relates to compounds of Formula IA or IB as described above, in which L¹ is C₂alkynyl.

Non limiting examples of this embodiment include the following compounds:

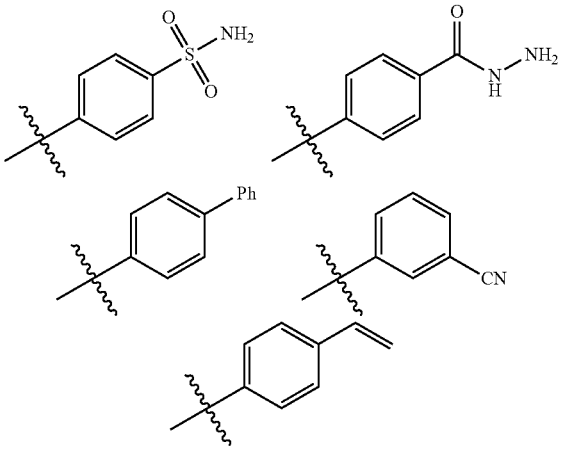

In one embodiment are compounds of Formulae IA, IB, IC or other classes and subclasses of this invention, in which W¹ is an aryl optionally substituted with 1-5 R$^a$, (i.e optionally substituted phenyl).

Illustrative examples of Phenyl moieties substituted with R$^a$ are:

-continued
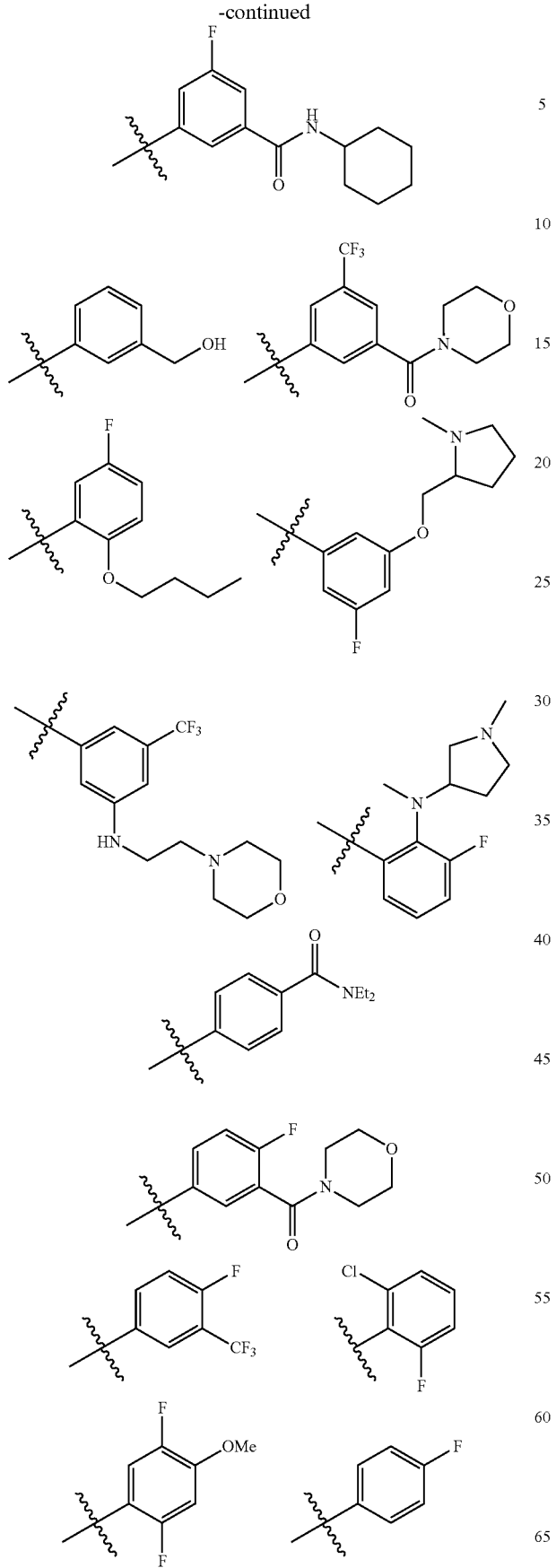
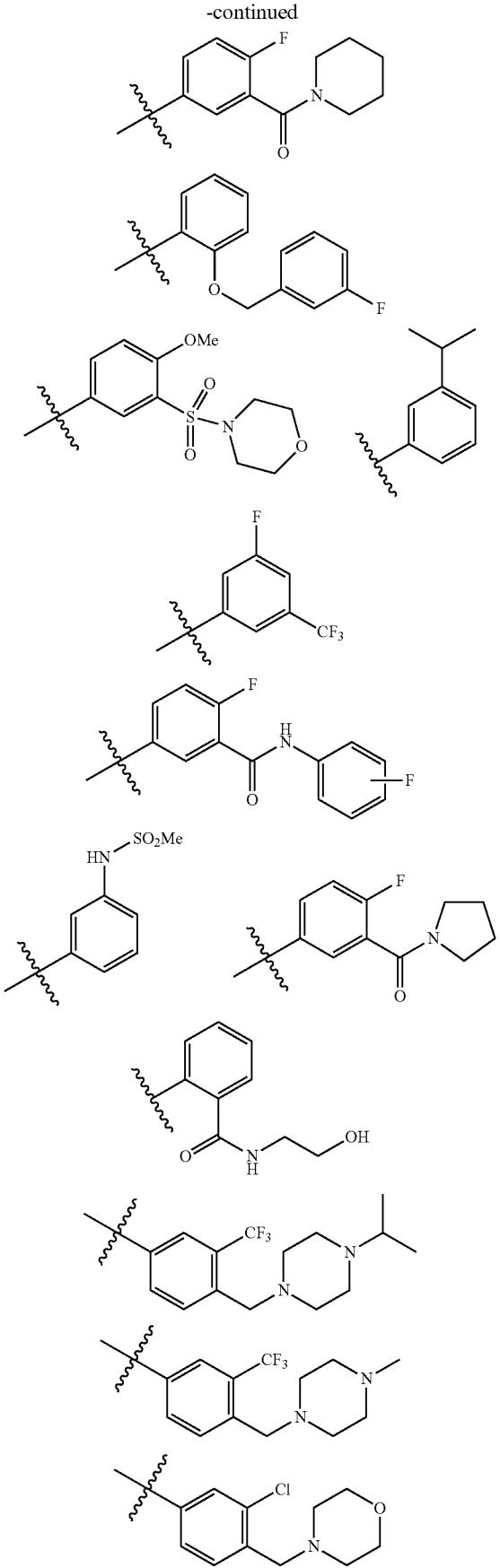

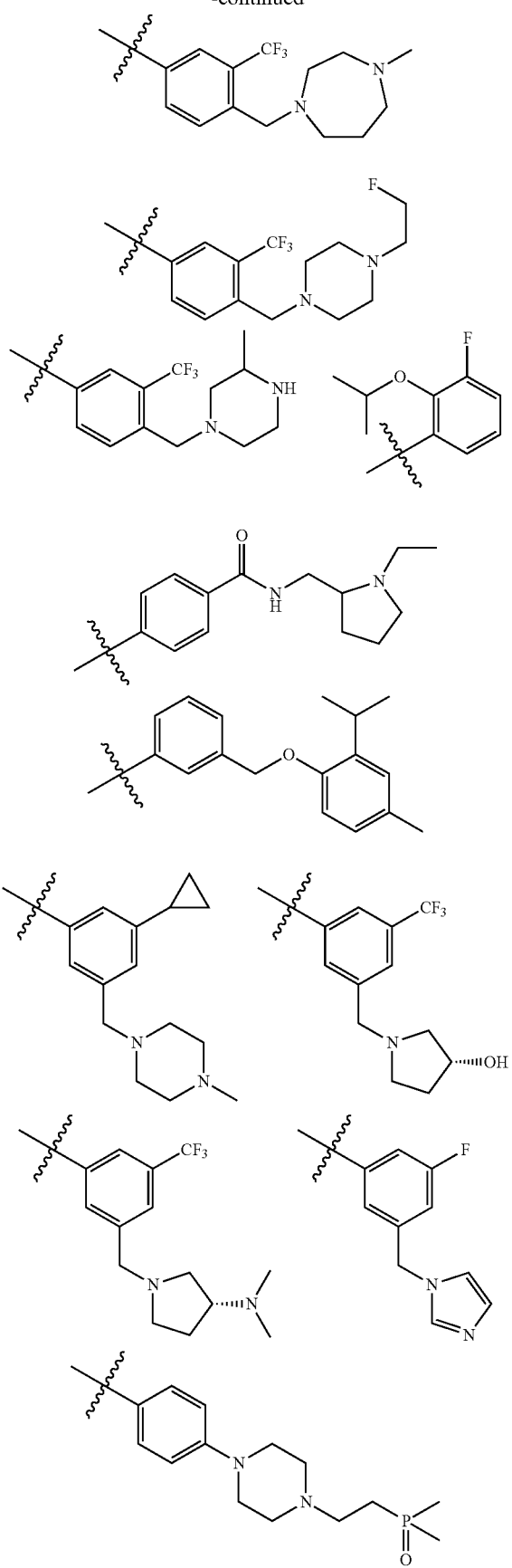
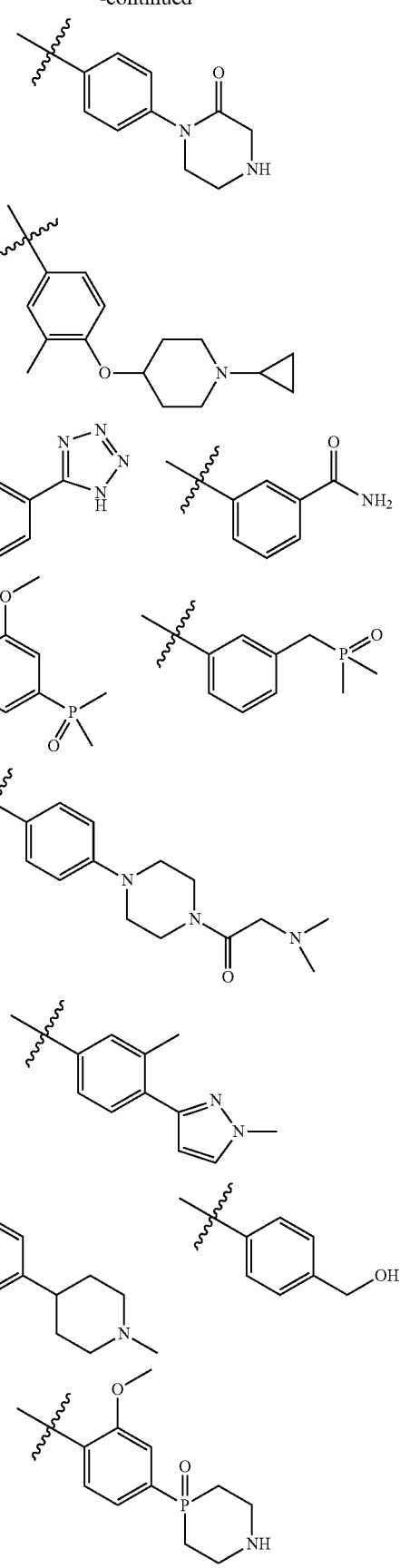

-continued

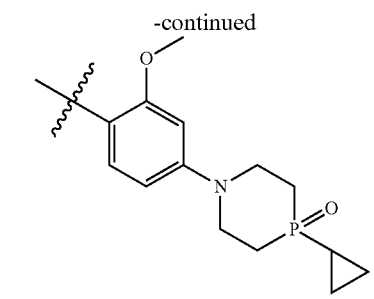

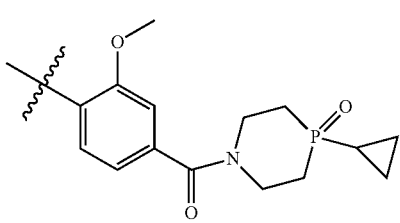

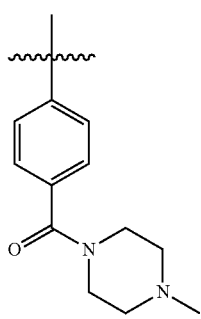 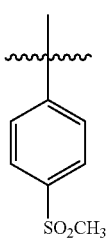 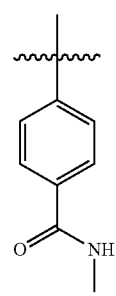

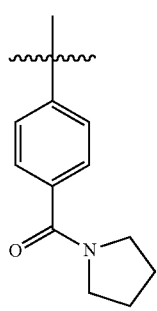 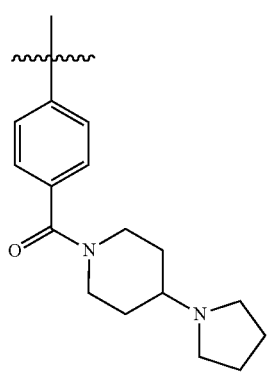

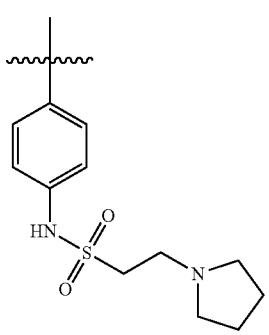

-continued

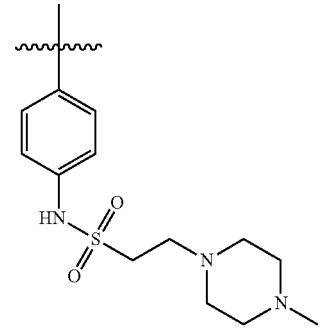

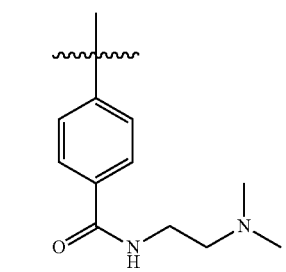

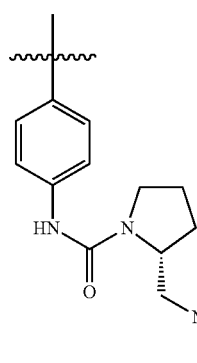 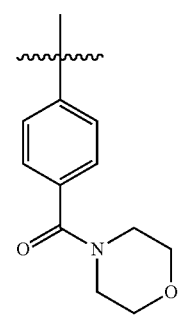

In another aspect of the previous embodiment are compounds of Formulae IA, IB, IC or other classes and subclasses of this invention in which $W^1$ is a 5-, 6- or 7-membered heterocyclyl ring comprising carbon atoms and 1-4 heteroatoms independently selected from O, N, P(O) and S(O)$_r$, and $W^1$ is substituted on carbon or on the heteroatom(s) with 1-5 $R^a$ groups. It is understood that the total number of substituents $R^a$ does not exceed the normal available valencies.

Non-limiting examples of this class are compounds of formula IA or LB in which $W^1$ is of the following types:

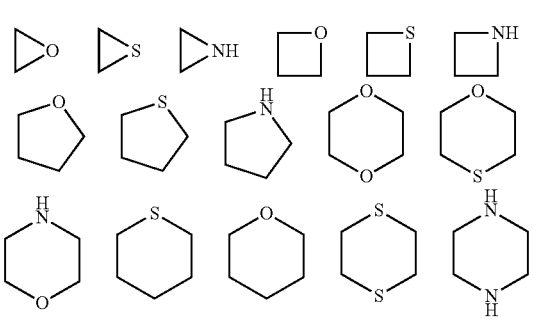

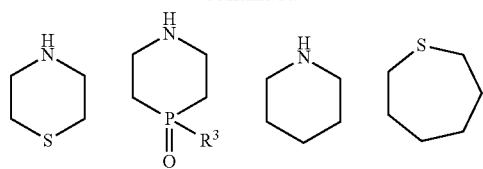
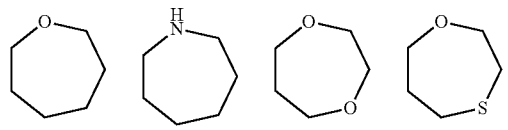
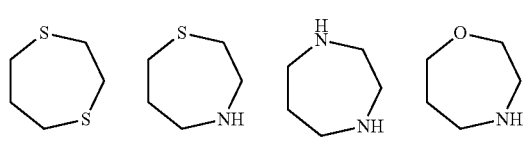
Non-limiting illustrative examples are compounds of the following formulae:
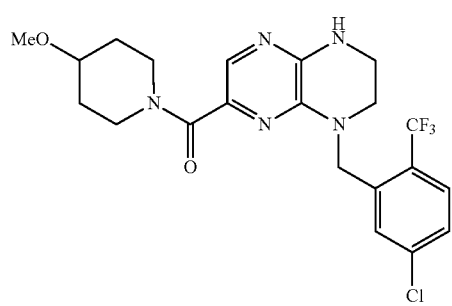
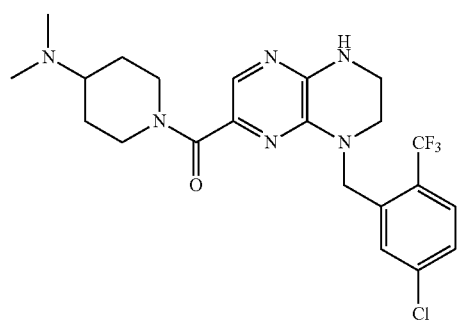
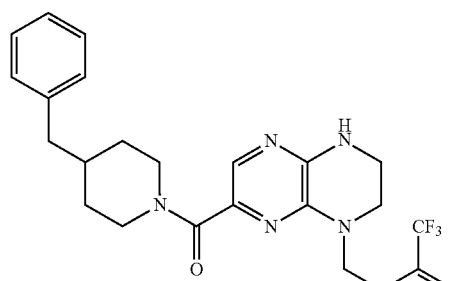
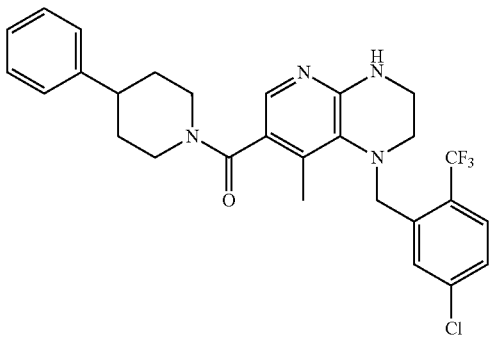
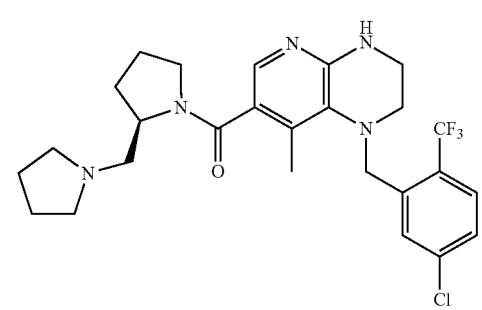
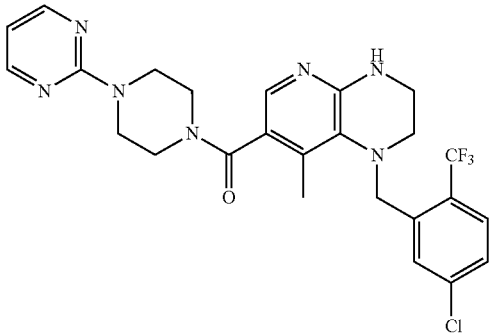
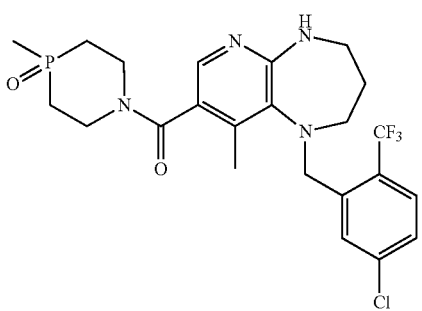
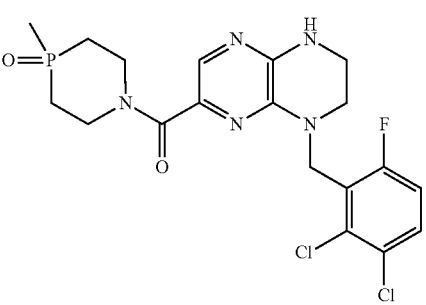

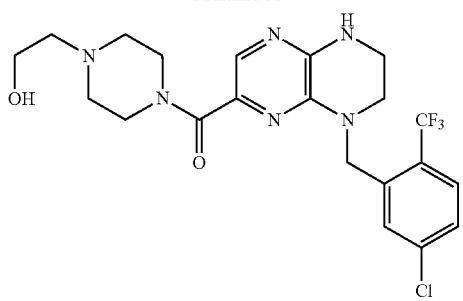

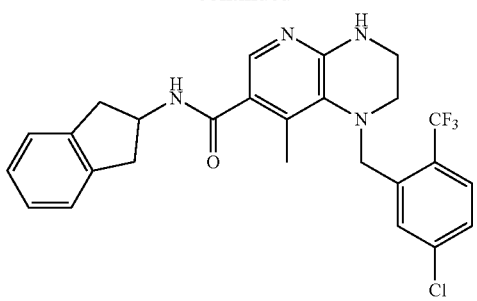

In another aspect of the previous embodiment are compounds of Formulae IA, IB or IC in which $W^1$ is a 3- to 8-membered carbocyclyl and $W^1$ is substituted with 1-5 $R^a$ groups. Non-limiting examples of this class are compounds of the following types:

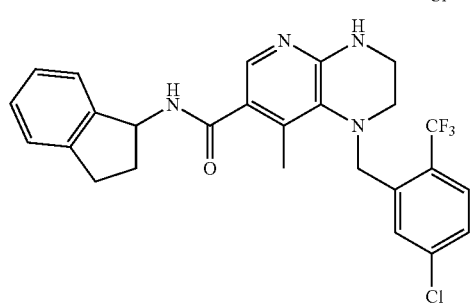

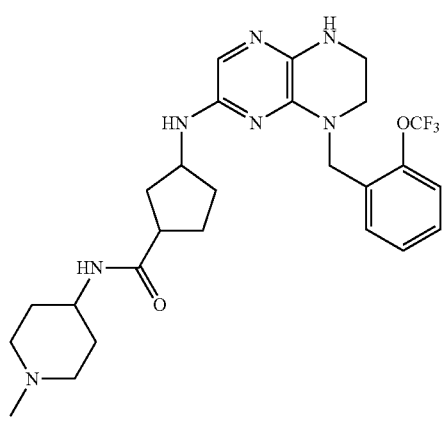

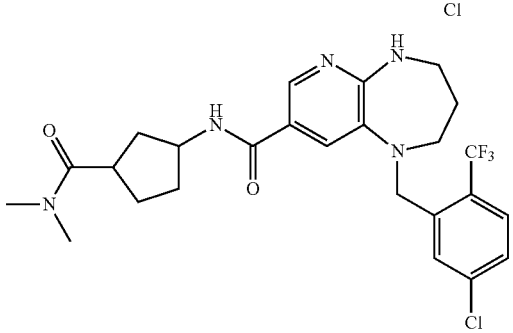

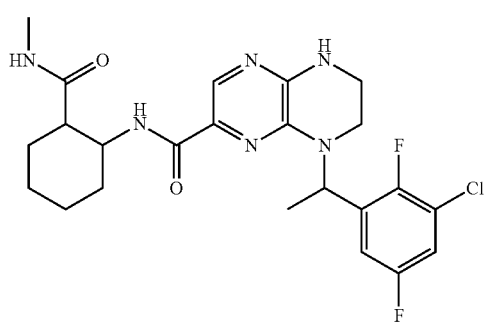

In another embodiment are compounds of Formulae IA, IB or IC in which $W^1$ is a 5-, 6-membered heteroaryl ring comprising carbon atoms and 1-4 heteroatoms independently selected from O, N and $S(O)_r$, and $W^1$ is optionally substituted on carbon or on the heteroatom(s) with 1-5 $R^a$ groups. It is understood that the total number of substituents $R^a$ does not exceed the normal available valencies.

In one aspect of the previous embodiment are compounds of Formulae IA, IB, IC or other subclasses in which $W^1$ is a 5-membered ring heteroaryl comprising carbon atoms and 1-3 Nitrogen atoms. Non-limiting examples of this class are compounds in which $W^1$ is of the following types:

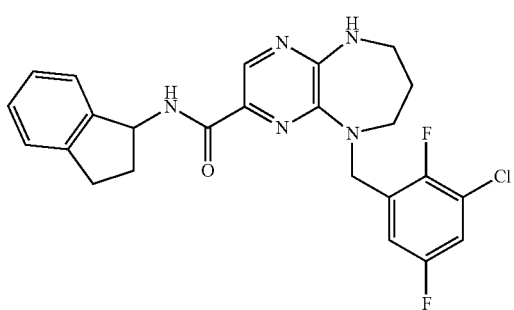

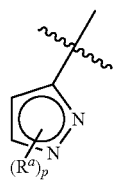 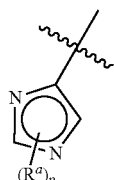 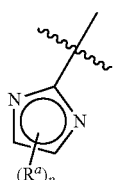

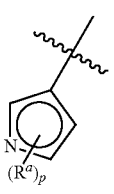 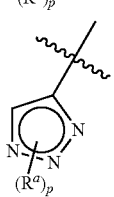 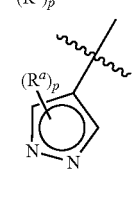

-continued

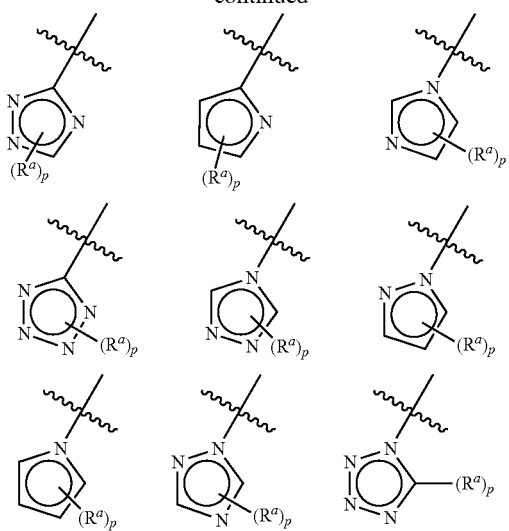

in which $R^a$ is as previously defined and p is 0, 1 2, 3 or 4. It is understood that the total number of substituents $R^a$ does not exceed the normal available valencies.

In a particular aspect of this embodiment, $W^1$ has the following formulae:

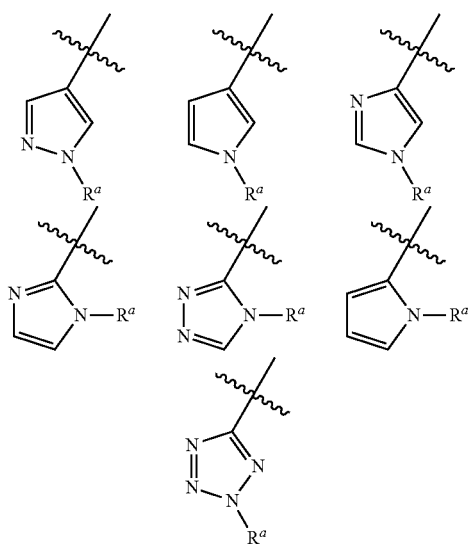

$R^a$ is as defined previously in part 1. Of additional interest is a class of compounds as described above in which $R^a$ is selected from the group consisting of —$R^1$ and —C(O)Y$R^2$. In another subclass of interest, are compounds of the above embodiment in which $R^a$ is H, an aryl, heteroaryl, substituted alkyl or heterocyclyl. Non limiting examples of substituted alkyl are H, —(CH$_2$)$_y$C(=O)N$R^1R^2$, —(CH$_2$)$_z$NHC(=O)$R^2$, —(CH$_2$)$_z$N$R^1R^2$, —(CH$_2$)$_y$C(=O)O$R^1$, —(CH$_2$)$_y$heterocyclyl, —(CH$_2$)$_y$aryl, —(CH$_2$)$_y$heteroaryl in which y is 0, 1, 2, 3 or 4, z is 1, 2, 3 or 4 and alkyl include straight (i.e. unbranched or acyclic), branched and cyclic alkyl groups and alkyl, aryl, heteroaryl, heterocyclyl groups are optionally substituted.

Illustrative examples of such compounds include those in which substituent $R^a$ is without limitation:

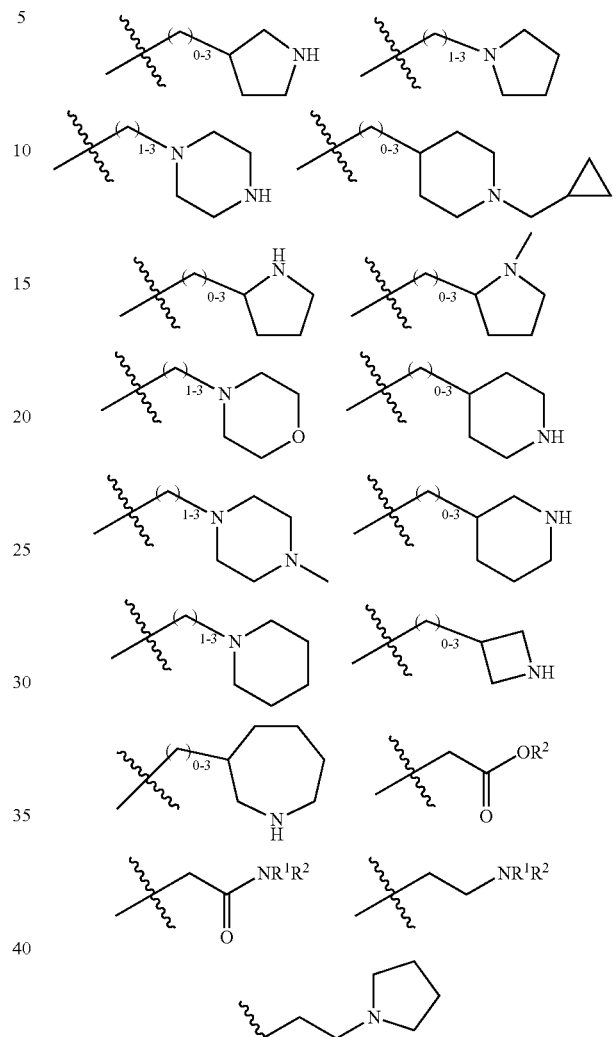

Other illustrative examples of this class include compounds in which $W^1$ is of the following types:

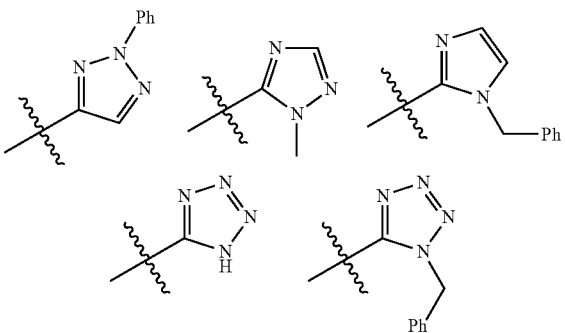

Non-limiting Illustrative examples of this class are compounds of the following formulae:

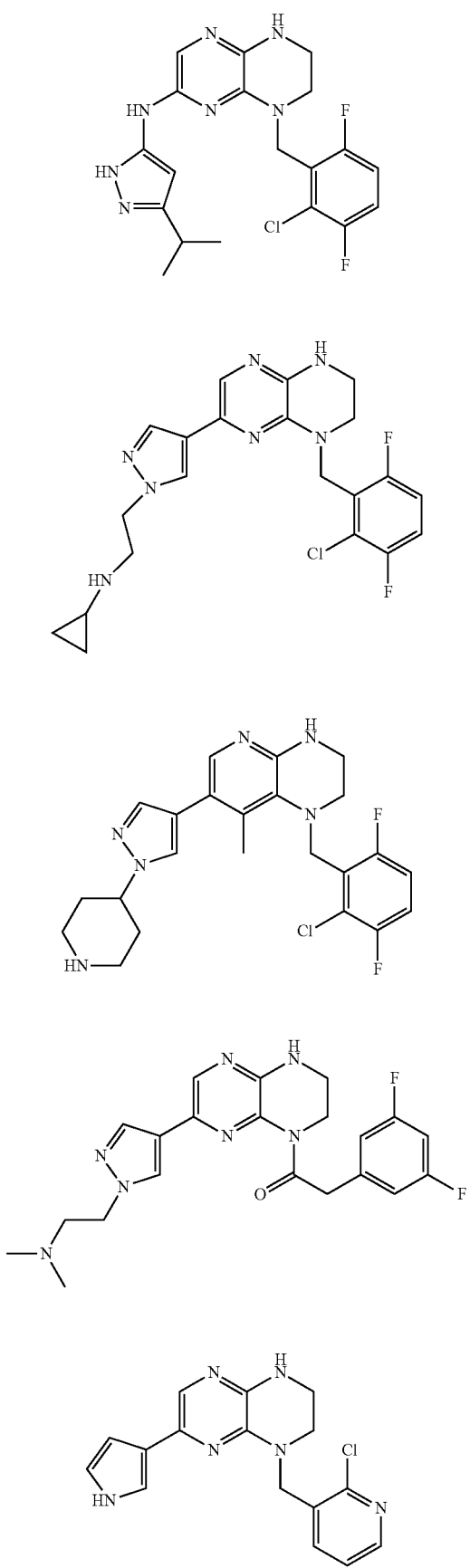 [SMILES: CC(C)c1cc(Nc2cnc3c(n2)N(Cc2c(F)ccc(F)c2Cl)CCN3)[nH]n1 ; Fc1ccc(F)c(CN2CCNc3ncc(-c4cnn(CCNC5CC5)c4)nc32)c1Cl ; Cc1c(-c2cnn(C3CCNCC3)c2)cnc2c1N(Cc1c(F)ccc(F)c1Cl)CCN2 ; CN(C)CCn1cc(-c2cnc3c(n2)N(C(=O)Cc2cc(F)cc(F)c2)CCN3)cn1 ; Clc1ncccc1CN1CCNc2ncc(-c3cc[nH]c3)nc21]
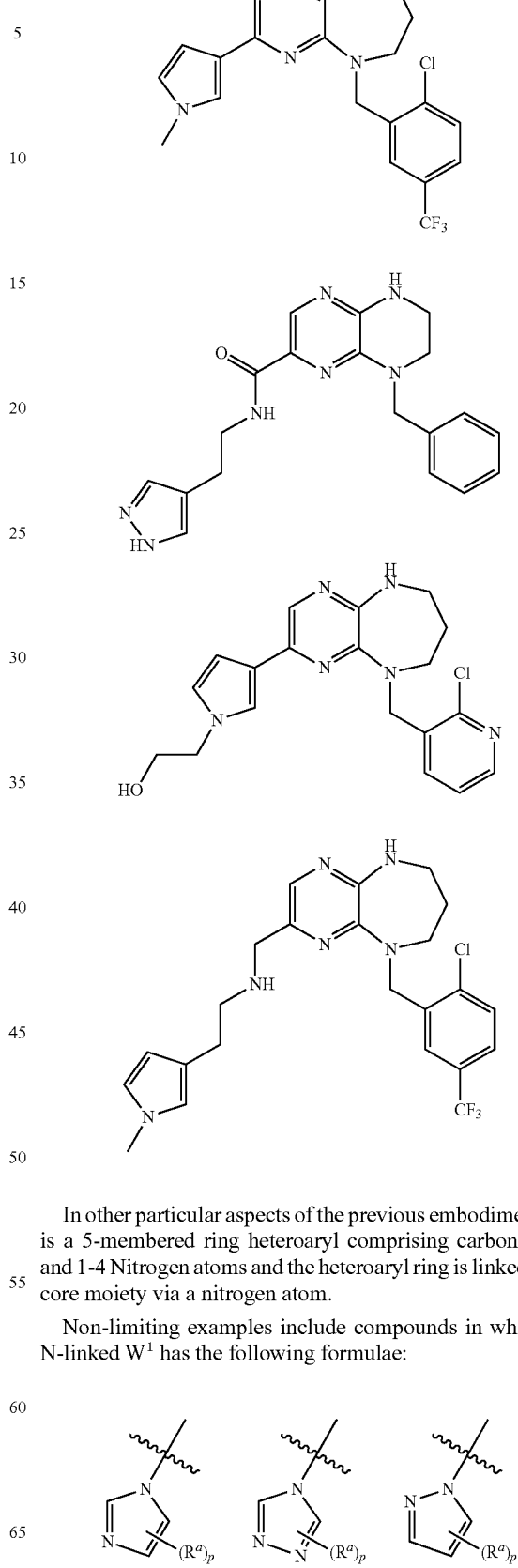
In other particular aspects of the previous embodiment, $W^1$ is a 5-membered ring heteroaryl comprising carbon atoms and 1-4 Nitrogen atoms and the heteroaryl ring is linked to the core moiety via a nitrogen atom.
Non-limiting examples include compounds in which the N-linked $W^1$ has the following formulae:
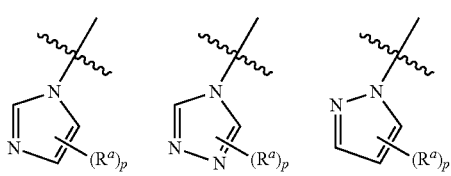

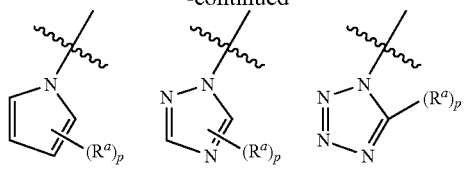

in which $R^a$ and p are as previously defined. It is understood that the total number of substituents $R^a$ does not exceed the normal available valencies. Thus, for example, when $W^1$ is an N-linked pyrolle ring, it can be substituted with 1 to 4 substituents (i.e. p is 1, 2, 3 or 4), whereas when $W^1$ is an N-linked pyrazole or an N-linked imidazole, it can only be substituted with a maximum of 3 substituents (i.e. p is 1, 2 or 3).

$R^a$ is as defined previously in part 1. Of additional interest is a class of compounds as described above in which $R^a$ is selected from the group consisting of —$R^1$, —$OR^2$, —P(=O)($R^3$)$_2$—$NR^1R^2$, —C(O)$YR^2$, —$NR^1$C(O)$YR^2$, —$NR^1SO_2R^2$, —S(O)$_rR^2$, —$SO_2NR^1R^2$ and —$NR^1SO_2NR^1R^2$. In another subclass of interest, are compounds of the above embodiment in which $R^a$ is an aryl, heteroaryl, substituted alkyl or heterocyclyl. Non limiting examples of $R^a$ are —(CH$_2$)$_y$C(=O)$NR^1R^2$, —(CH$_2$)$_y$NHC(=O)$R^2$, —(CH$_2$)$_y$$NR^1R^2$, —(CH$_2$)$_y$heterocyclyl, —(CH$_2$)$_y$aryl, —(CH$_2$)$_y$heteroaryl, NH-aryl, NH-heteroaryl and NH-heterocyclyl; in which y is 0, 1, 2, 3 or 4 and alkyl include straight (i.e. unbranched or acyclic), branched and cyclic alkyl groups and alkyl, aryl, heteroaryl, heterocyclyl groups are optionally substituted.

Illustrative non limiting examples of such compounds include compounds of Formula IA or IB in which $W^1$ is a triazole of the following formulae:

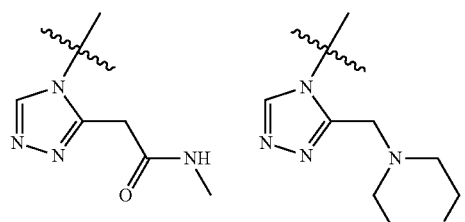

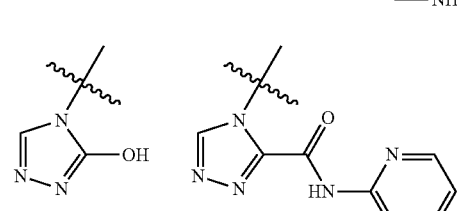

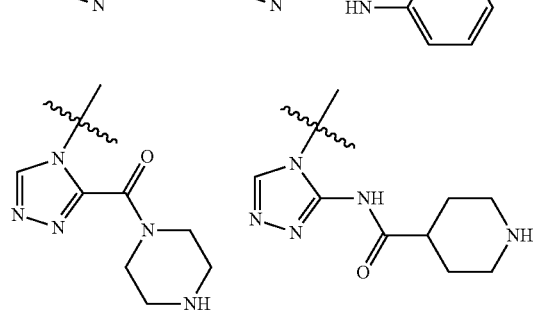

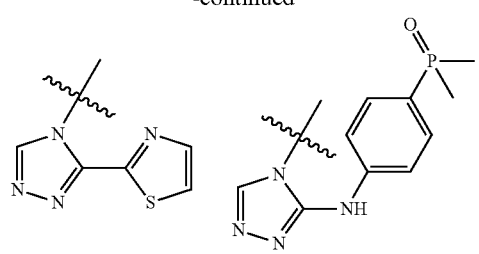

In another aspect of the previous embodiment, $W^1$ is a pyrazole of the following formulae:

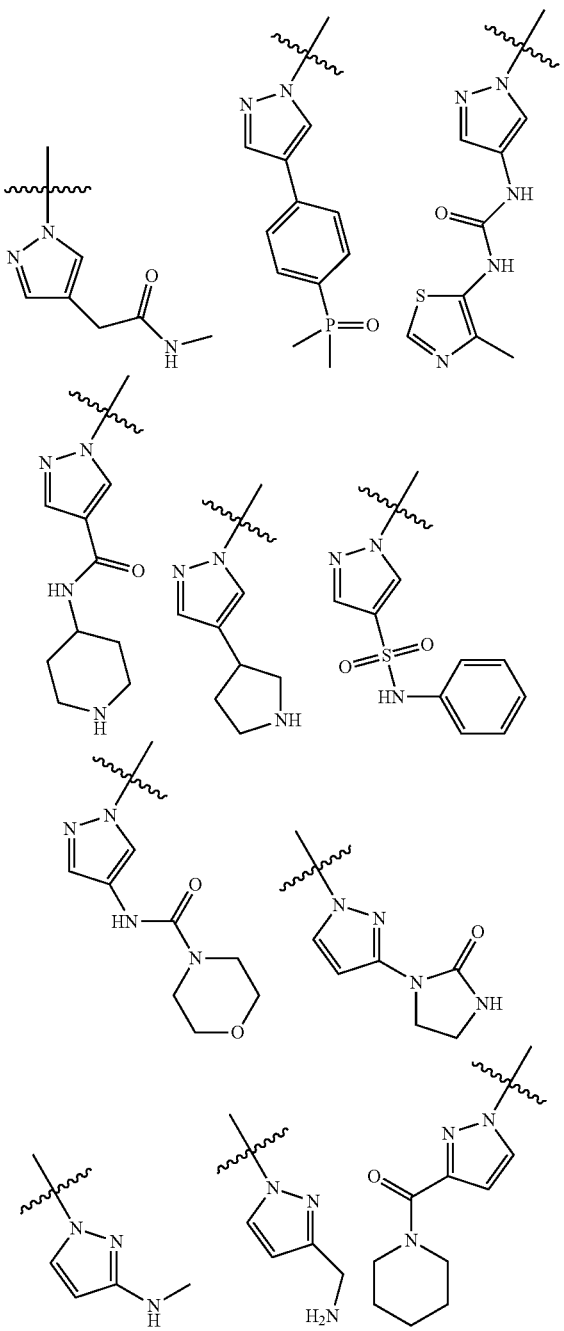

-continued
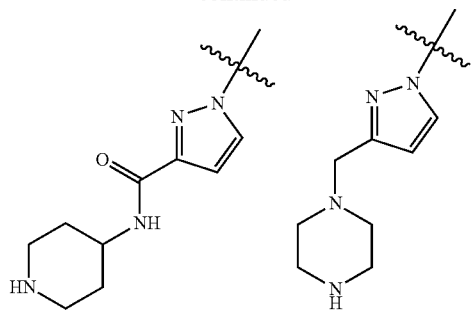
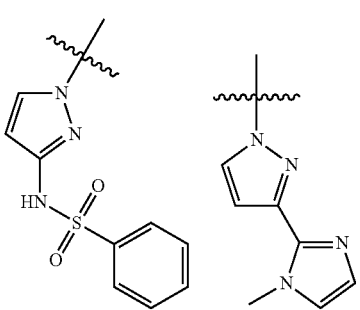 [SMILES: *n1ccc(NS(=O)(=O)c2ccccc2)n1 ; *n1ccc(-c2nccn2C)n1]
In another aspect of the previous embodiment, $W^1$ is a tetrazole of the following formulae:
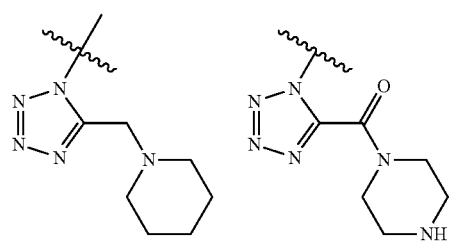
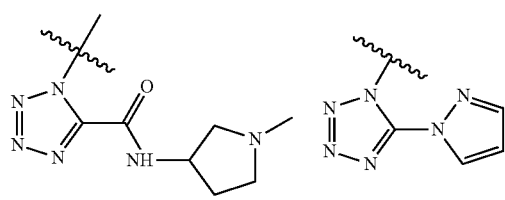
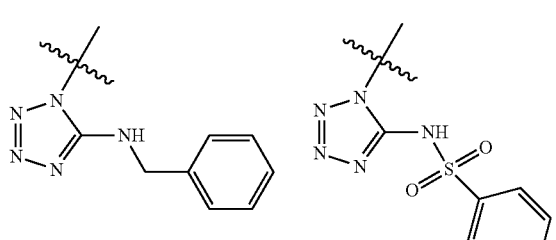
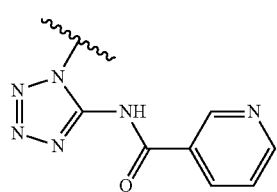
-continued
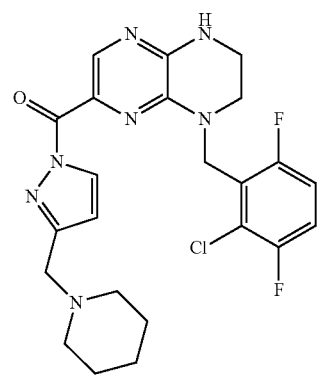
Non-limiting Illustrative examples of this class are compounds of the following formulae:
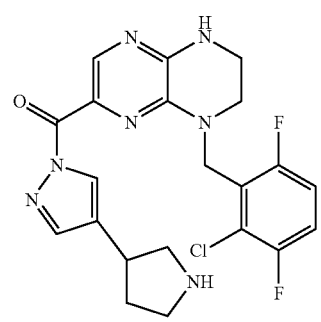
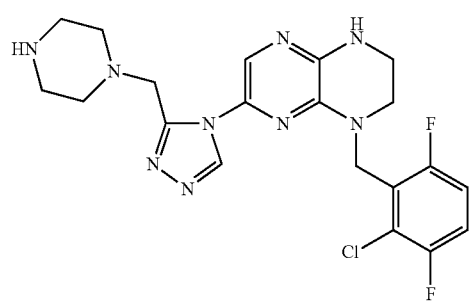
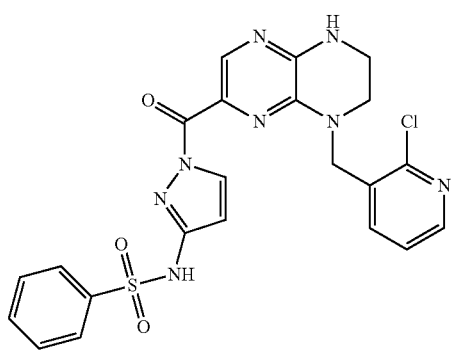

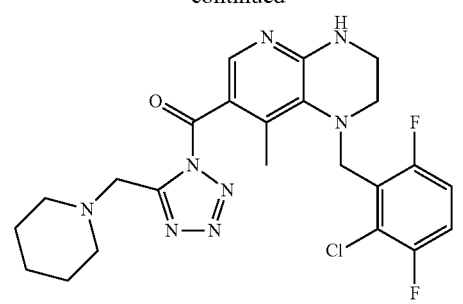

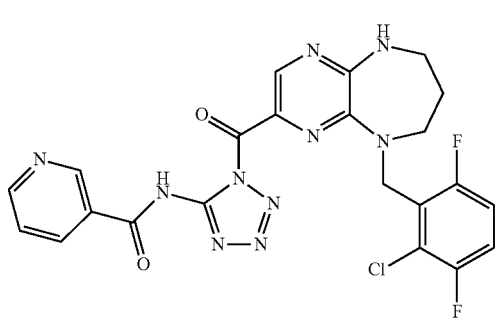 [SMILES: O=C(Nc1nnnn1C(=O)c1cnc2c(n1)N(Cc1c(F)ccc(F)c1Cl)CCCN2)c1cccnc1]

In another aspect of the previous embodiment, W¹ is a 5-membered ring heteroaryl comprising carbon atoms and 1-4 heteroatoms selected from N and O. Non limiting examples are compounds of formula IA, IB or IC in which W¹ is of the following type:

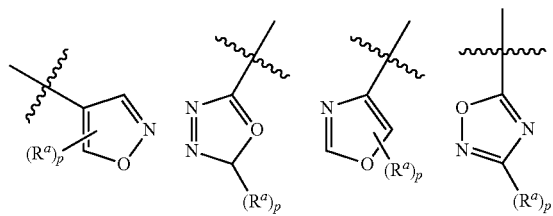

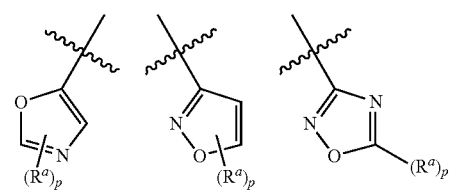

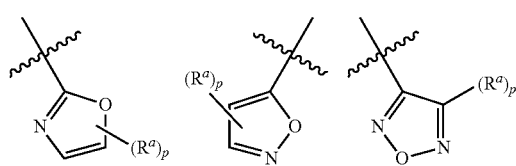

in which p is defined previously and the total number of substituents $R^a$ does not exceed the normal available valencies.

In a particular aspect of this embodiment, W¹ has the following formulae:

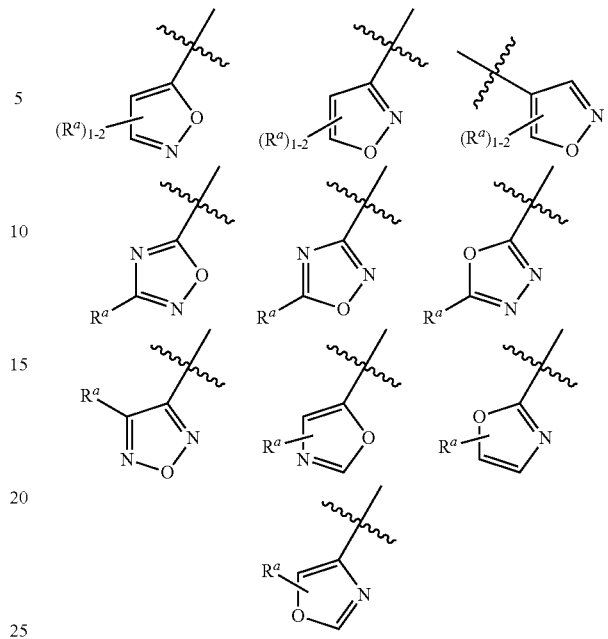

in which W¹ is substituted with one or two $R^a$ substituents.

$R^a$ is as defined previously in part 1. Of additional interest is a class of compounds as described above in which $R^a$ is selected from the group consisting of —$R^1$, —P(=O)($R^3$)₂, —$OR^2$, —C(O)Y$R^2$, —$NR^1$C(O)Y$R^2$, —$NR^1SO_2R^2$, —S(O)$_rR^2$, —SO₂$NR^1R^2$ and —$NR^1SO_2NR^1R^2$.

In another subclass of interest, are compounds of the above embodiment in which $R^a$ is NHC(O)$R^1$, NHC(O)$NR^1R^2$, C(O)NH$R^1$, C(O)$NR^1R^2$, $NR^1R^2$, an aryl, heteroaryl, substituted alkyl or heterocyclyl. Non limiting examples of $R^a$ are —(CH₂)$_y$C(=O)$NR^1R^2$, —(CH₂)$_y$NHC(=O)$R^2$, —(CH₂)$_y$$NR^1R^2$, —(CH₂)$_y$$OR^2$, —(CH₂)$_y$heterocyclyl, —(CH₂)$_y$aryl, —(CH₂)$_y$heteroaryl, NH-aryl, NH-heteroaryl and NH-heterocyclyl, —(CH₂)$_m$P(=O)(alkyl)₂; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class include compounds of formulae IA, IB or IC in which W¹ is:

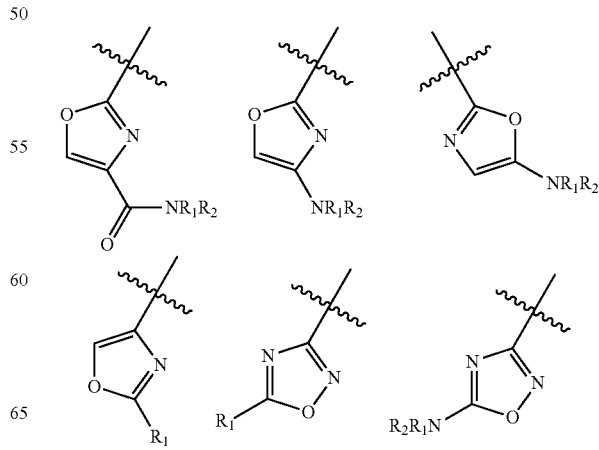

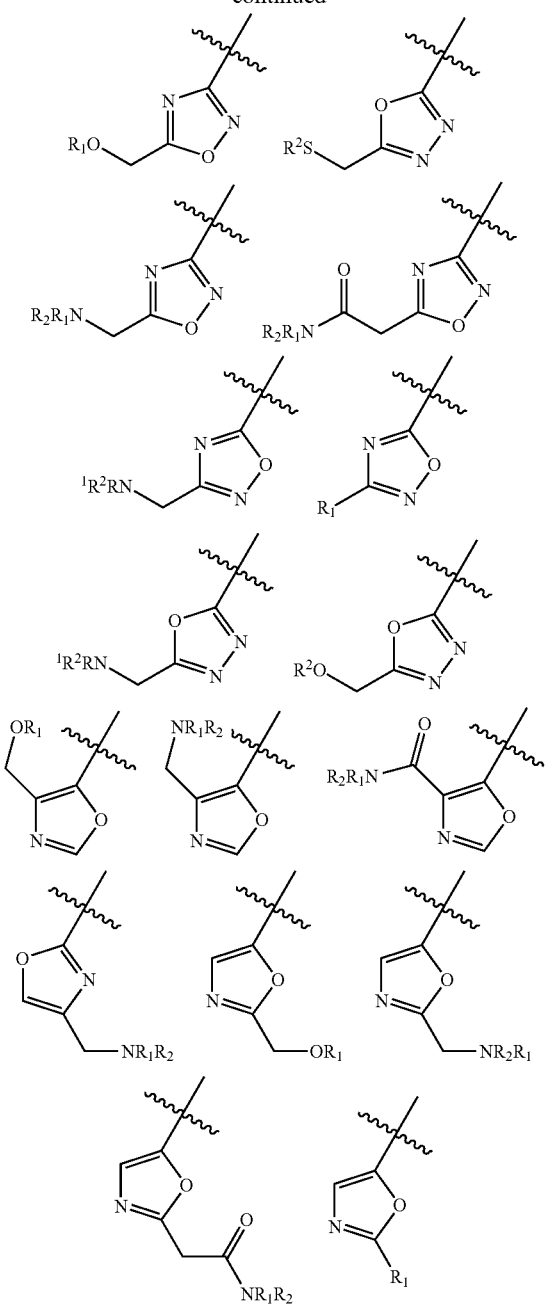
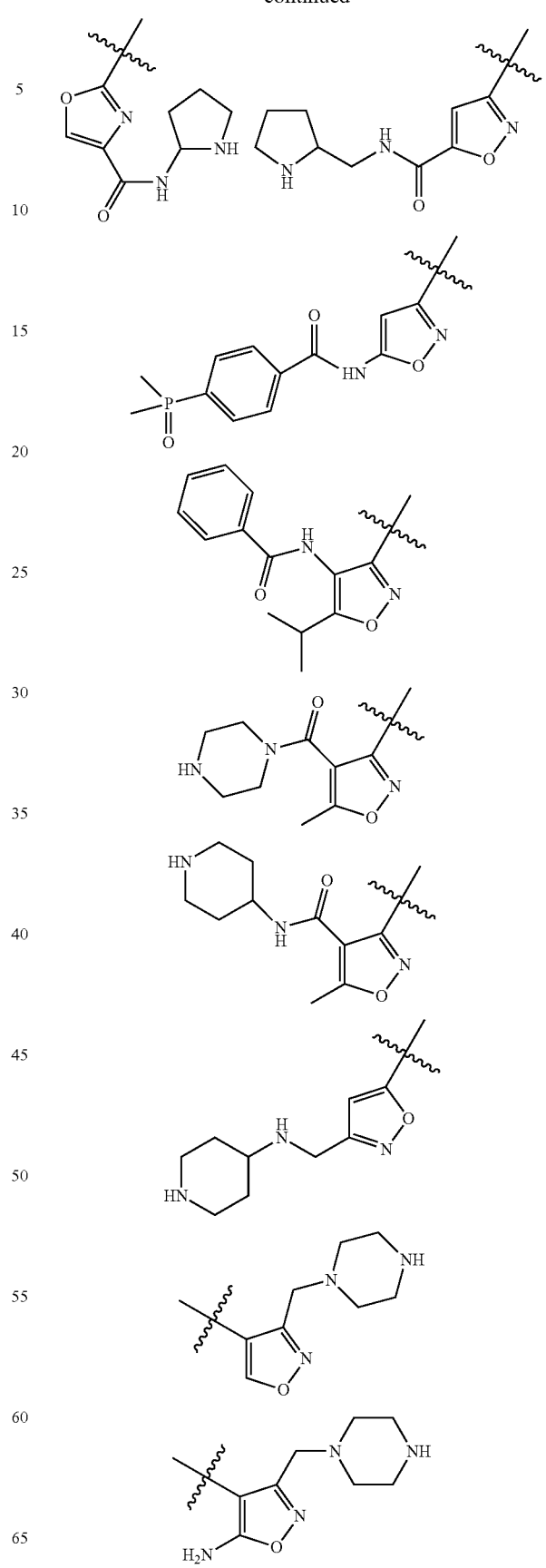
Specific, non-limiting illustrative examples of this class include compounds of formula IA, IB or IC in which substituted $W^1$ is of the following formulae:
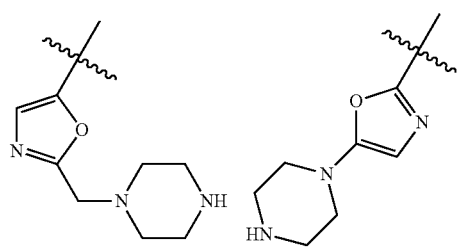

-continued
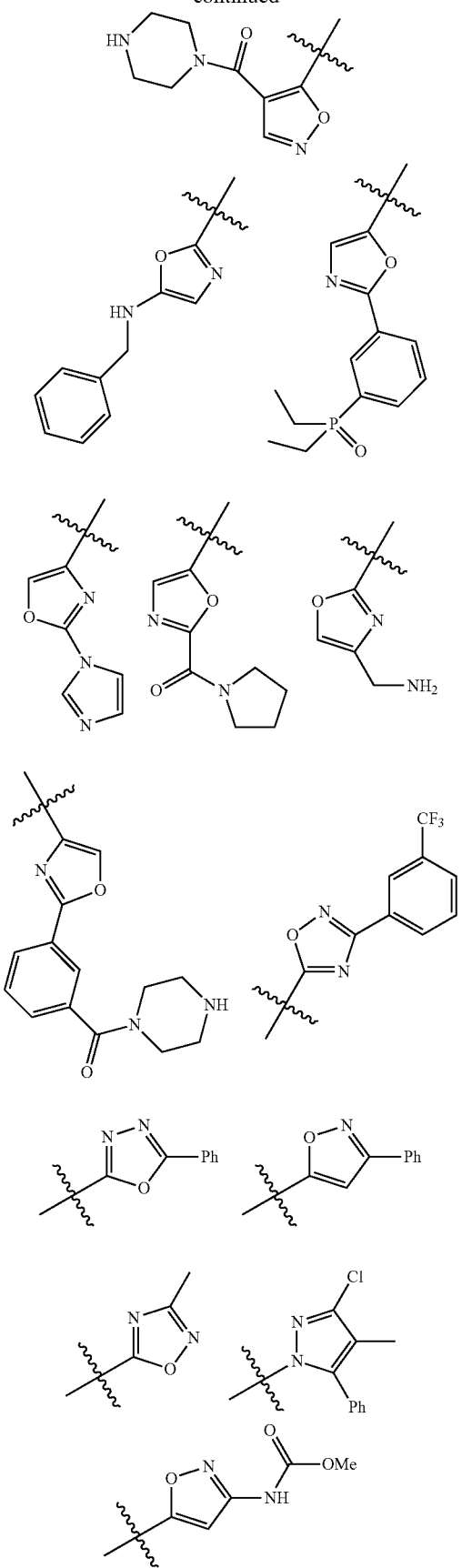
-continued
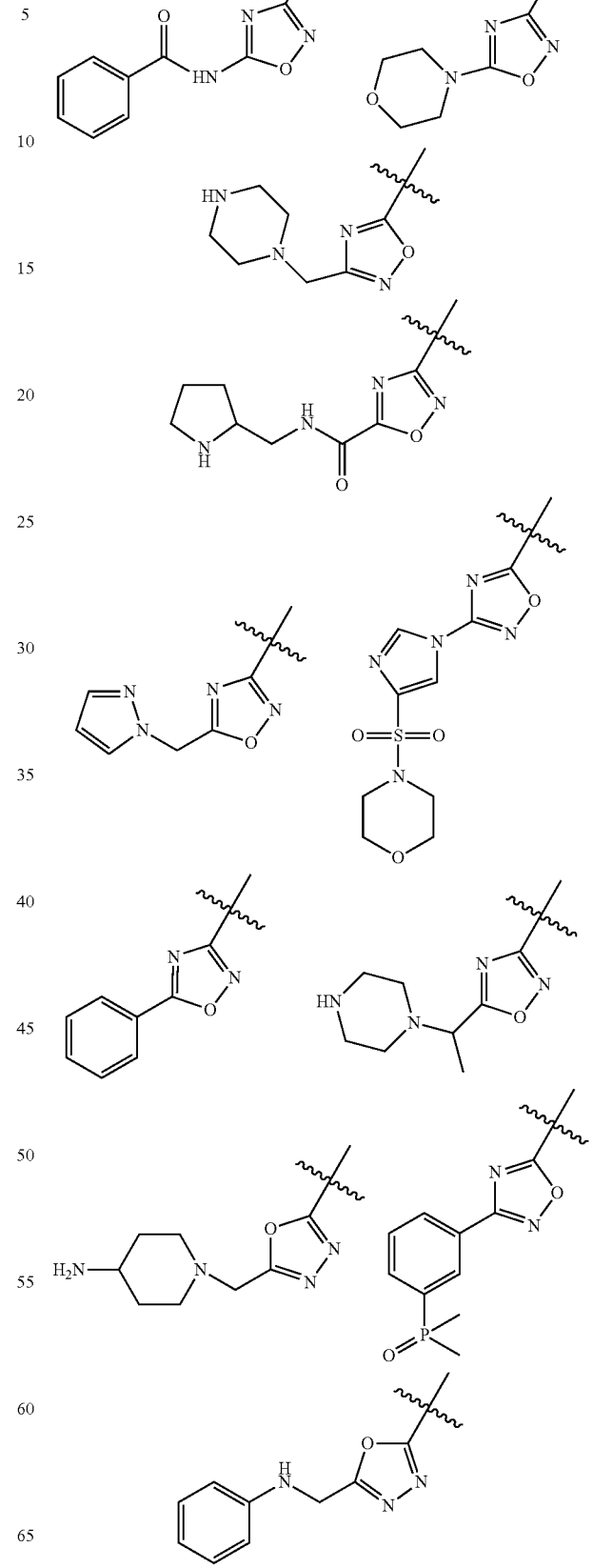

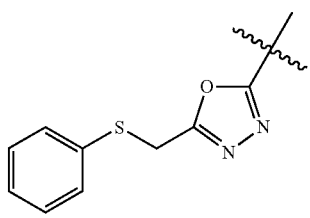
Non-limiting Illustrative examples of this class are compounds of the following formulae:
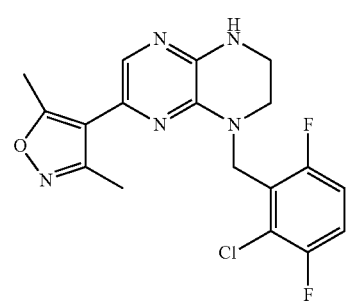
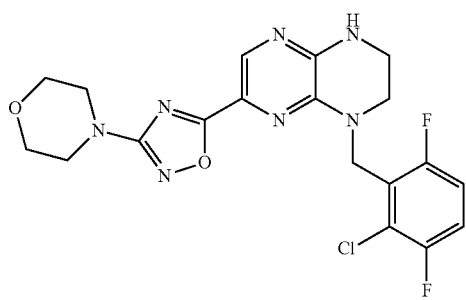
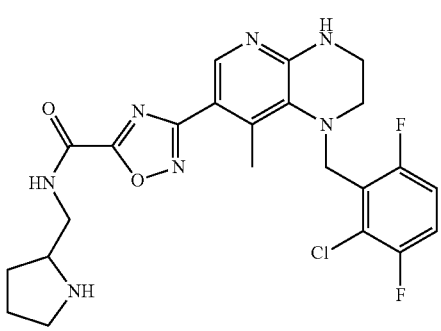
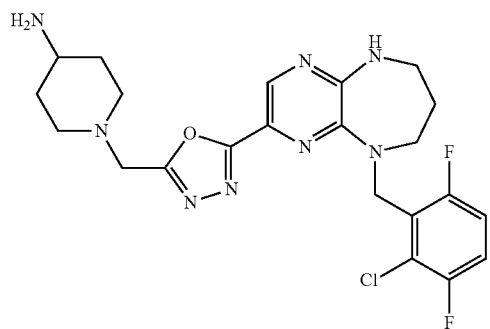
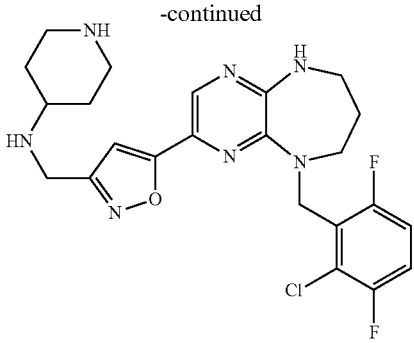
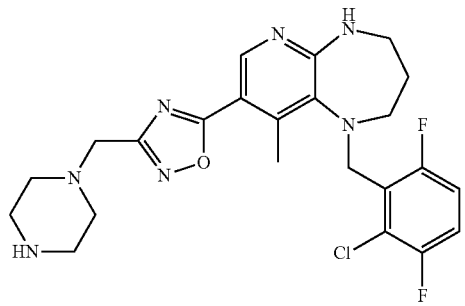
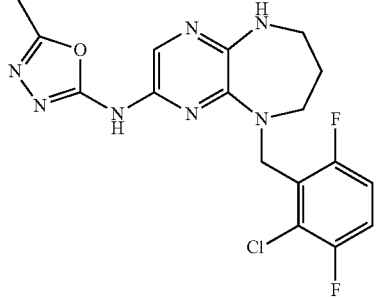
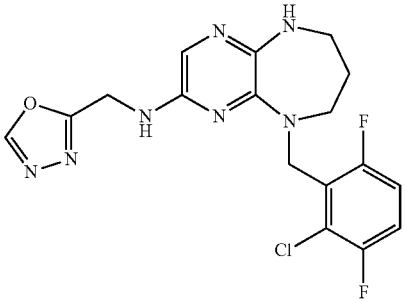
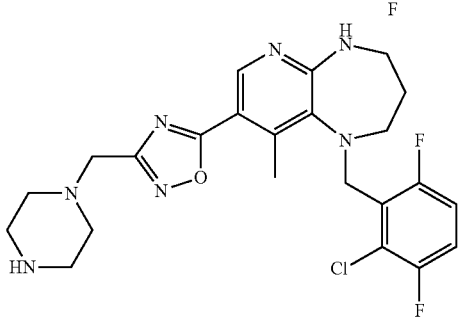

In another specific embodiment, W¹ is a 5-membered heteroaryl comprising carbon atoms and 1-4 heteroatoms selected from N and S.

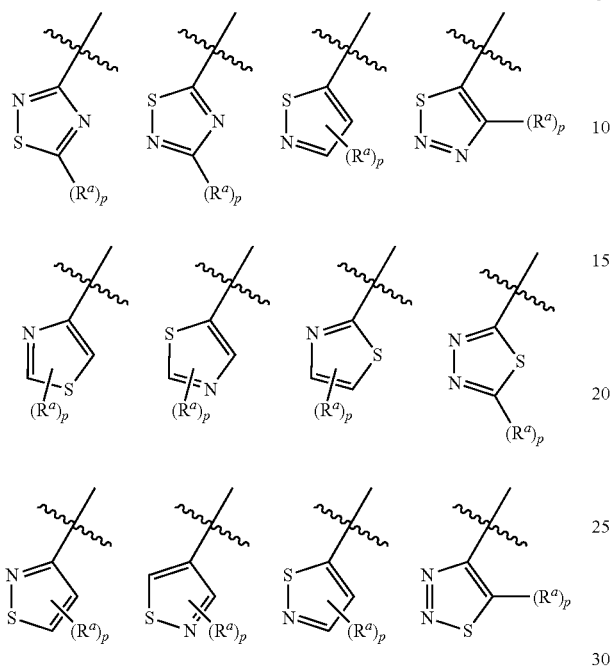

in which p is defined previously and the total number of substituents R$^a$ does not exceed the normal available valencies.

Of particular interest is a class of compounds as described above in which R$^a$ is selected from the group consisting of —R¹, —P(═O)(R³)$_2$, —OR², —NR¹R², —C(O)YR², —NR¹C(O)YR², —NR¹SO$_2$R², —S(O)$_r$R², —SO$_2$NR¹R² and —NR¹SO$_2$NR¹R². In another subclass of interest, are compounds of the above embodiment in which R$^a$ is NHC(O)R¹, C(O)NHR¹, C(O)NR¹R², NHC(O)NHR¹, NR¹R², an aryl, heteroaryl, substituted alkyl or heterocyclyl. Non limiting examples of R$^a$ are —(CH$_2$)$_y$C(═O)NR¹R², —(CH$_2$)$_y$NHC(═O)R², —(CH$_2$)$_y$NR¹R², —(CH$_2$)$_y$OR², —SO$_2$NR¹R², —(CH$_2$)$_y$SR², —(CH$_2$)$_y$heterocyclyl, —(CH$_2$)$_y$aryl, —(CH$_2$)$_y$heteroaryl, NH-aryl, NH-heteroaryl, NH-heterocyclyl and —(CH$_2$)$_m$P(═O)(alkyl)$_2$; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class include compounds of formula IA, IB or IC in which W¹ is:

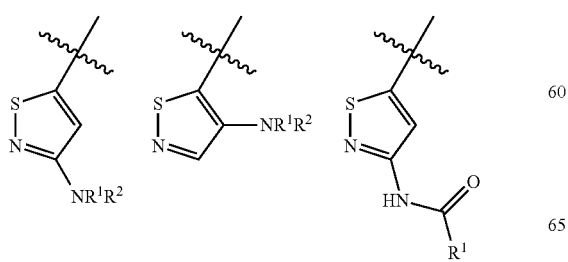

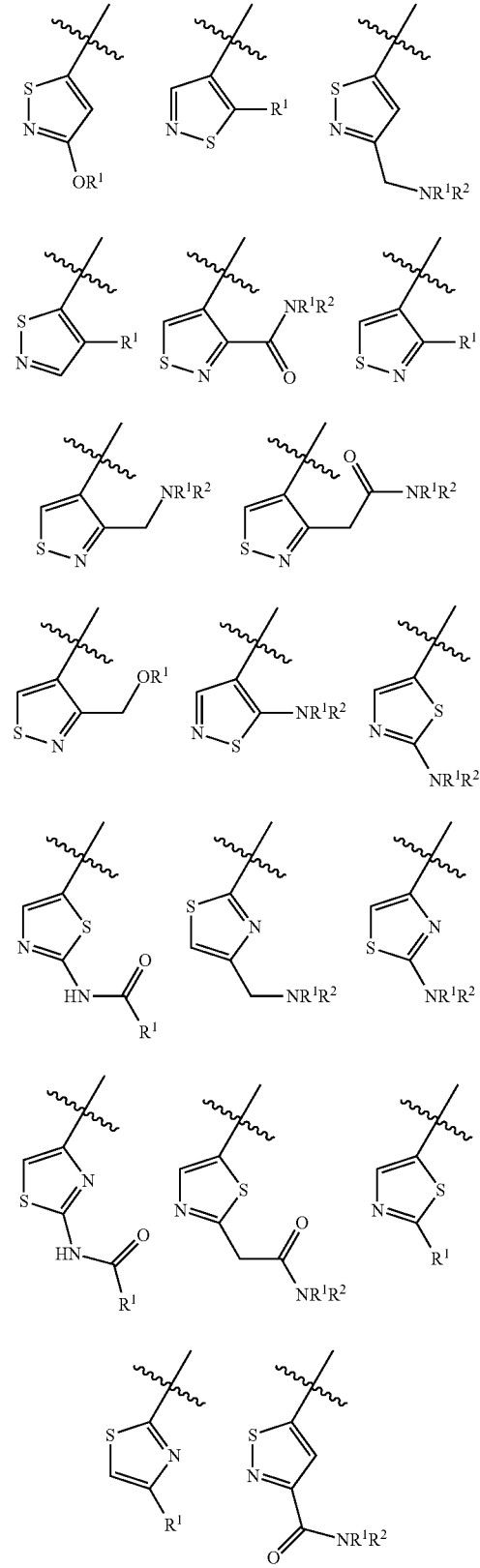

Specific, non-limiting illustrative examples of this class include compounds of formula IA, IB or IC in which substituted W¹ is of the following formulae:

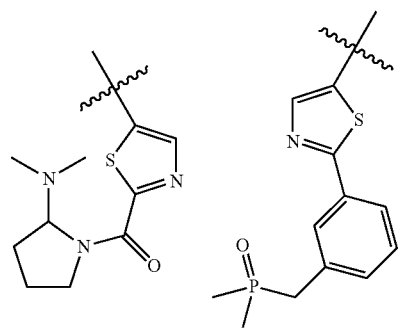
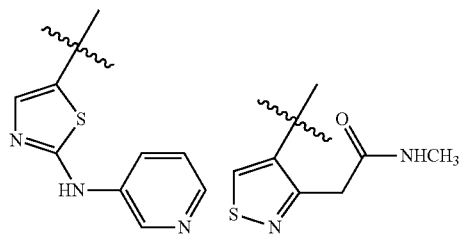
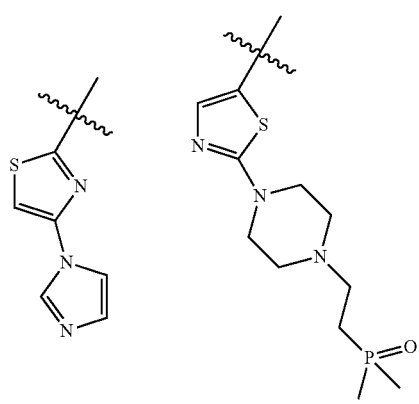
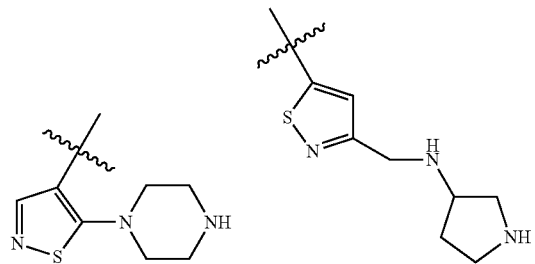
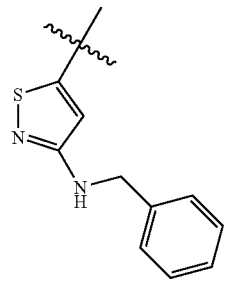
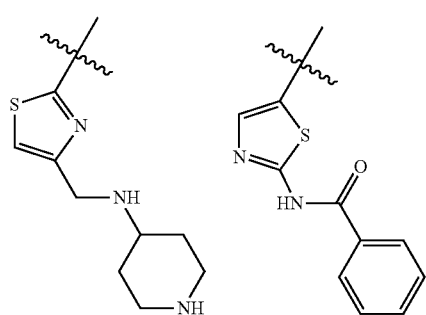
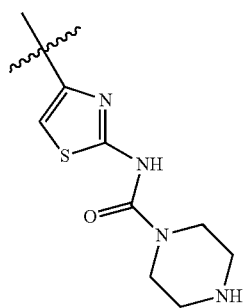
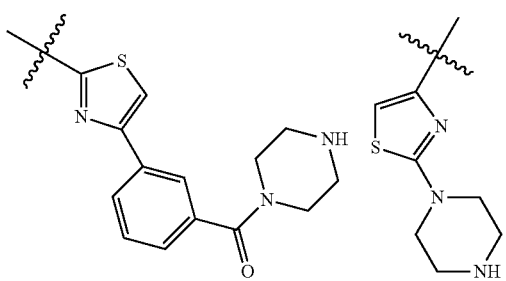
Non-limiting Illustrative examples of this class are compounds of the following formulae:
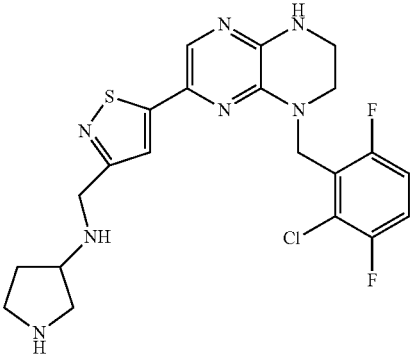
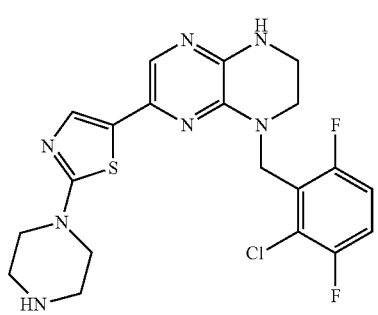

-continued

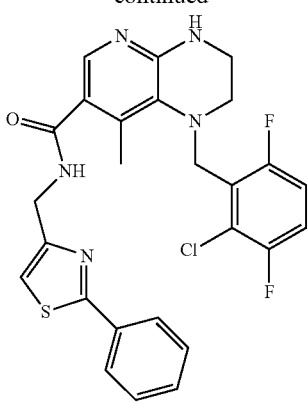

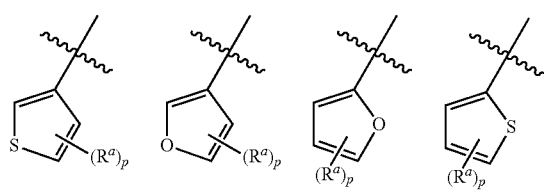

Other non-limiting examples include compounds of formula IA, IB or IC in which W¹ is furan or thiofuran:

in which p is defined previously and the total number of substituents $R^a$ does not exceed the normal available valencies.

Specific, non-limiting illustrative examples of this class include compounds of formula IA, IB or IC in which substituted W¹ is of the following formulae:

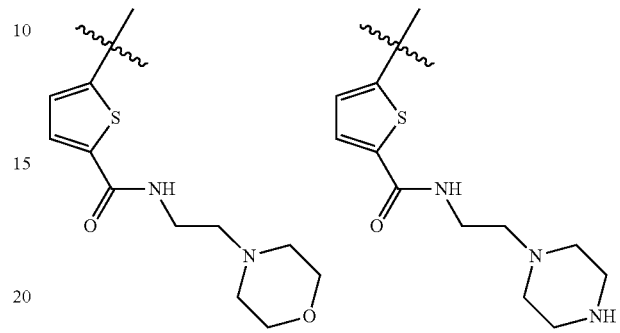

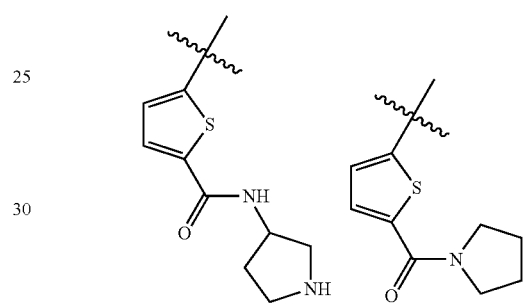

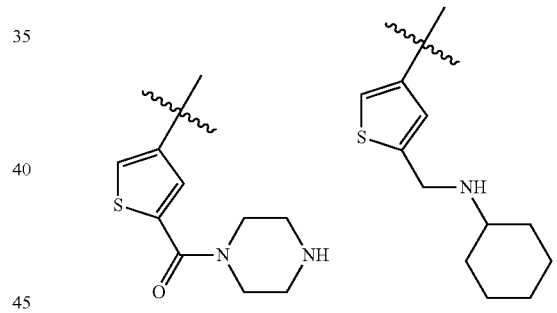

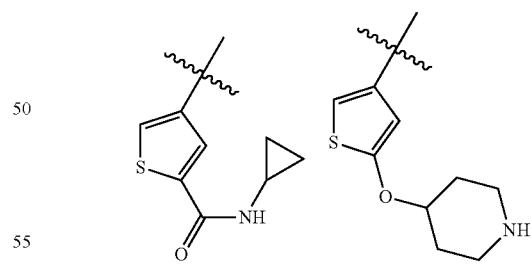

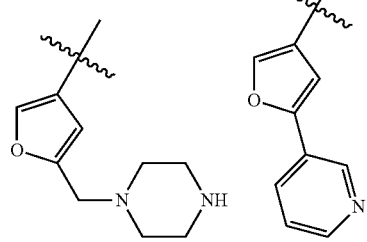

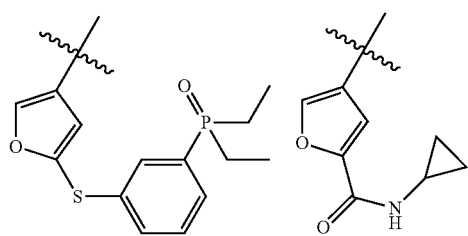

Non-limiting Illustrative examples of this class are compounds of the following formulae:

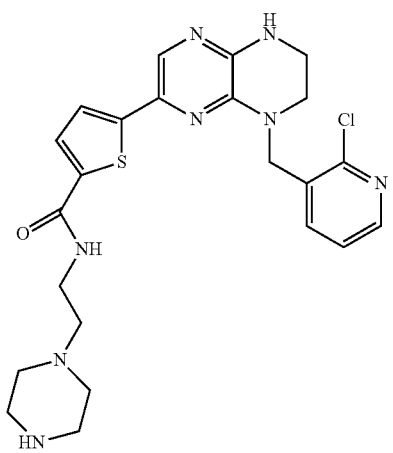

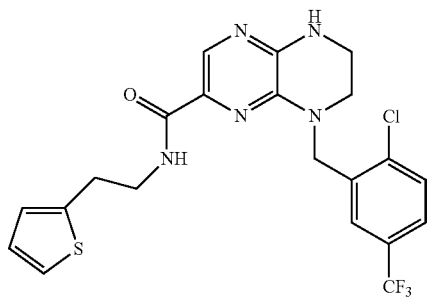

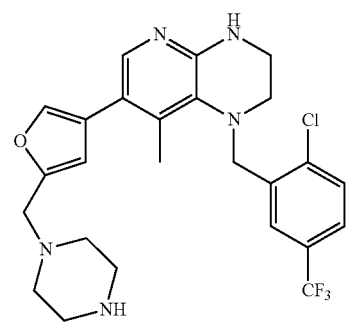

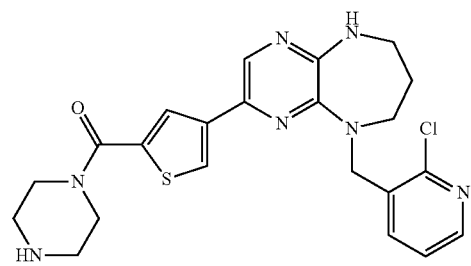

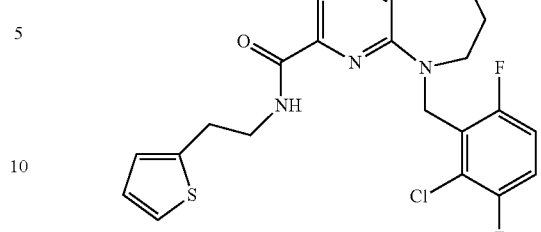

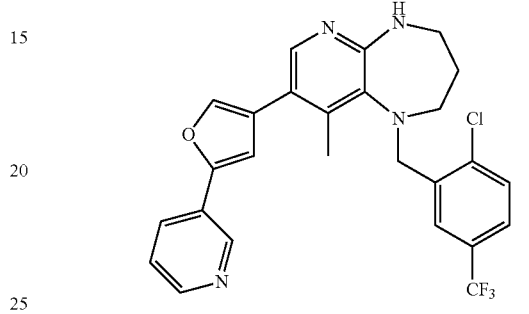

In another embodiment, $W^1$ is a 6-membered heteroaryl ring.

In one aspect of this embodiment, $W^1$ is a pyrimidine of the following types:

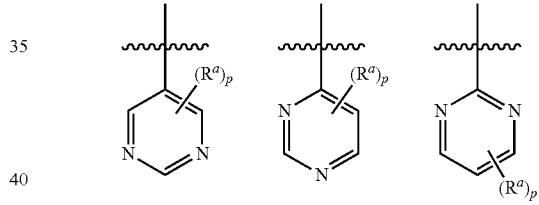

in which p is as previously described and the total number of substituents $R^a$ does not exceed the normal available valencies.

Of particular interest is a class of compounds as described above in which $R^a$ is selected from the group consisting of —$R^1$, —$P(=O)(R^3)_2$, —$OR^2$, —$NR^1R^2$, —$C(O)YR^2$, —$NR^1C(O)YR^2$, —$NR^1SO_2R^2$, —$S(O)_rR^2$, —$SO_2NR^1R^2$ and —$NR^1SO_2NR^1R^2$. In another subclass of interest, are compounds of the above embodiment in which $R^a$ is NHC(O)$R^1$, NHC(O)NHR$^1$, C(O)NHR$^1$, C(O)NR$^1R^2$, NR$^1R^2$, an aryl, heteroaryl, substituted alkyl or heterocyclyl. Non limiting examples of $R^a$ are —$OCH_2CH_2NR^1R^2$, —$OCH_2C(O)NR^1R^2$, —$NR^1C(O)NR^1R^2$, —$(CH_2)_yC(=O)NR^1R^2$, —$(CH_2)_yNHC(=O)R^2$, —$(CH_2)_yNR^1R^2$, —$(CH_2)_yOR^2$, —$SO_2NR^1R^2$, —$(CH_2)_ySR^2$, —$(CH_2)_y$heterocyclyl, —$(CH_2)_y$aryl, —$(CH_2)_y$heteroaryl, NH-aryl, NH-heteroaryl, NH-heterocyclyl and —$(CH_2)_mP(=O)(alkyl)_2$; in which y and m are independently selected from 0, 1, 2, 3 and 4 and alkyl include straight (i.e. unbranched or acyclic), branched and cyclic alkyl groups and alkyl, aryl, heteroaryl, heterocyclyl groups are optionally substituted.

Non-limiting examples of this class are compounds of formula IA, IB or IC in which $W^1$ is:

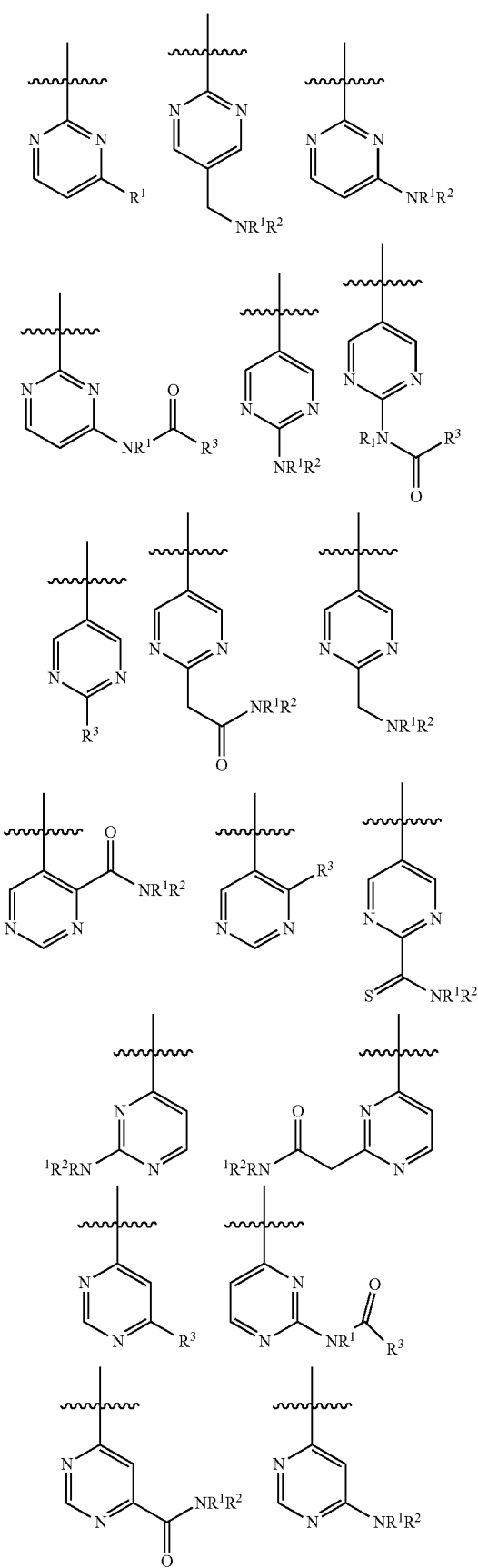
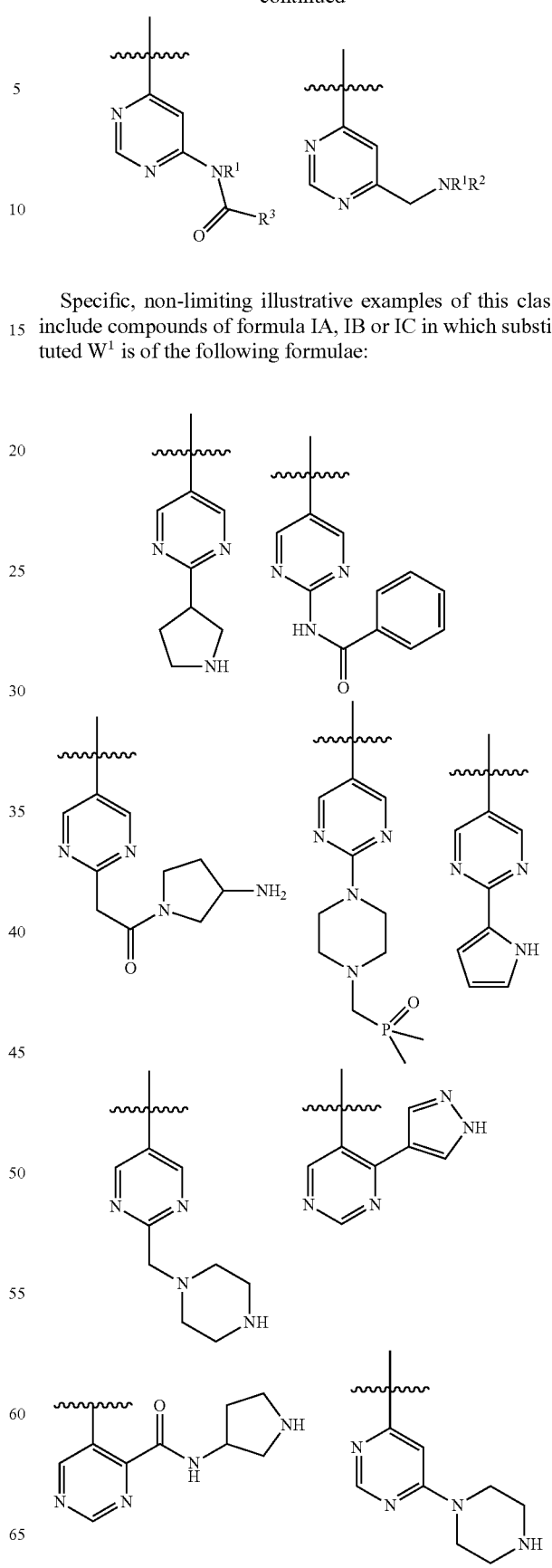
Specific, non-limiting illustrative examples of this class include compounds of formula IA, IB or IC in which substituted $W^1$ is of the following formulae:

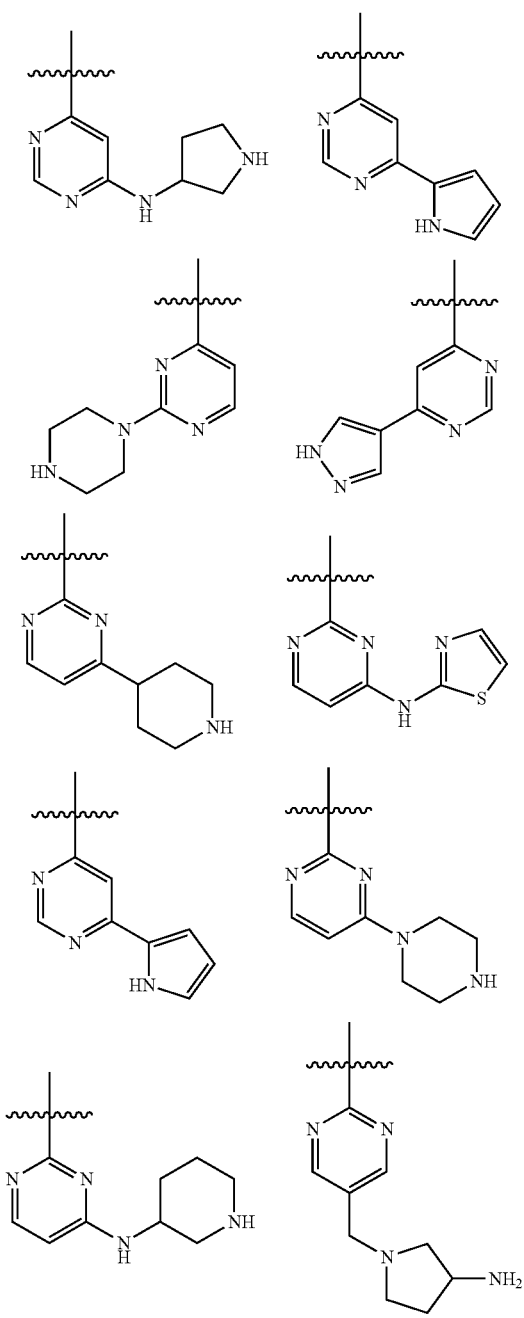
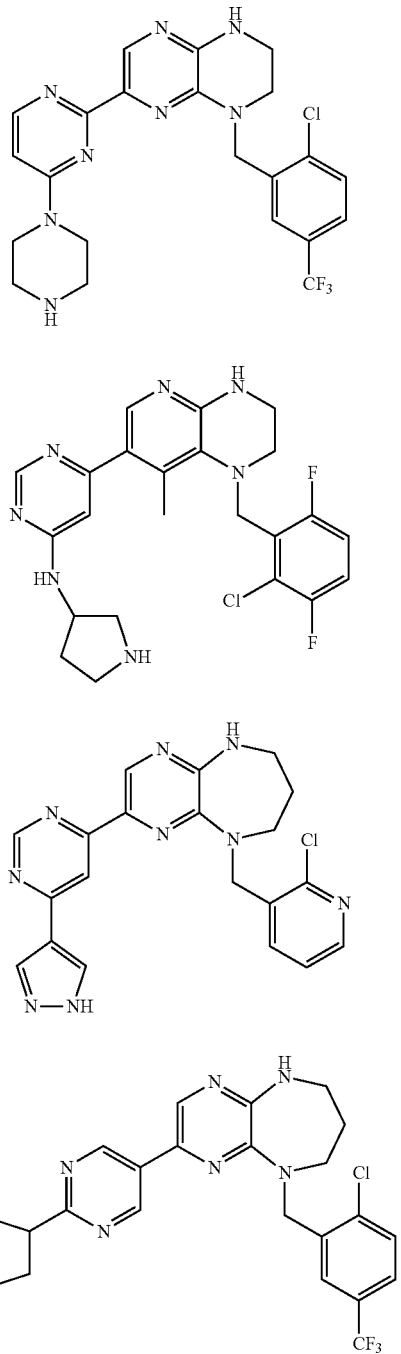
Non-limiting Illustrative examples of this class are compounds of the following formulae:
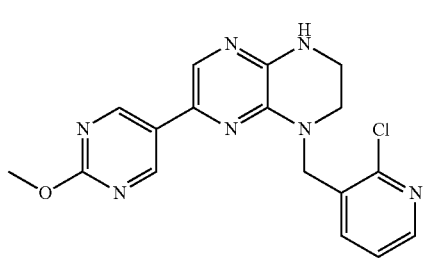
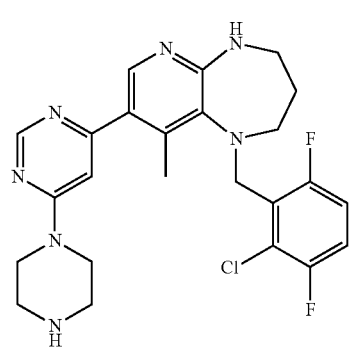

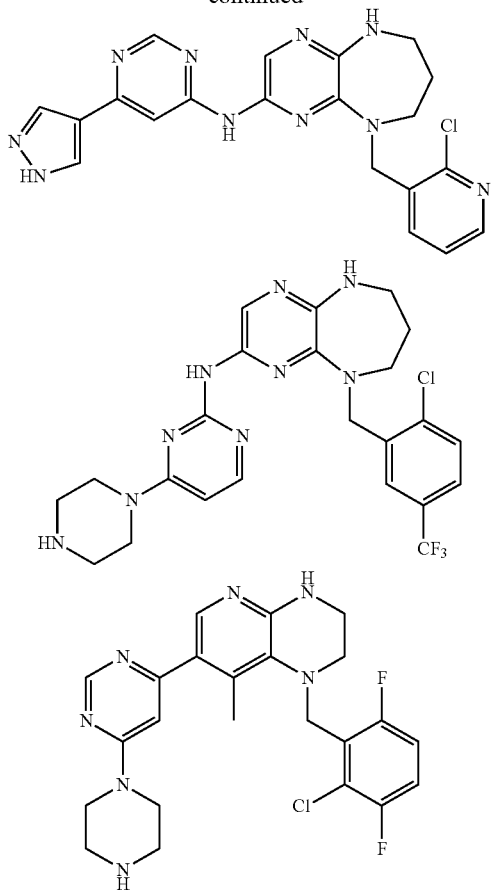

In another embodiment, $W^1$ is a pyridine substituted with 1-4 $R^a$. Of particular interest is a class of compounds as described above in which $R^a$ is selected from the group consisting of —$R^1$, —P(=O)($R^3$)$_2$, —$OR^2$, —$NR^1R^2$, —$NR^1C(O)R^2$, —$NR^1SO_2R^2$. In another subclass of interest, are compounds of the above embodiment in which $R^a$ is H, NHC(O)$R^2$, $NR^1R^4$, an aryl, heteroaryl, substituted alkyl or heterocyclyl. Non limiting examples of $R^a$ are H, —(CH$_2$)$_y$C(=O)$NR^1R^2$, —(CH$_2$)$_y$C(=O)aryl, —(CH$_2$)$_y$C(=O)heteroaryl, —(CH$_2$)$_y$C(=O)heterocyclyl, —(CH$_2$)$_y$NHC(=O)$R^2$, —(CH$_2$)$_y$$NR^1R^2$, —(CH$_2$)$_y$$OR^2$, —(CH$_2$)$_y$$SR^2$, —(CH$_2$)$_y$heterocyclyl, —(CH$_2$)$_y$aryl, —(CH$_2$)$_y$heteroaryl, NH-aryl, NH-heteroaryl, NH-heterocyclyl and —(CH$_2$)$_m$P(=O)(alkyl)$_2$, in which y and m are independently selected from 0, 1, 2, 3 and 4; and alkyl include straight (i.e. unbranched or acyclic), branched and cyclic alkyl groups and alkyl, aryl, heteroaryl, heterocyclyl groups are optionally substituted.

Non-limiting examples of this class are compounds of formula IA, IB or IC in which $W^1$ is:

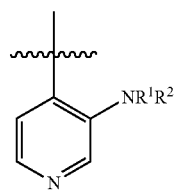

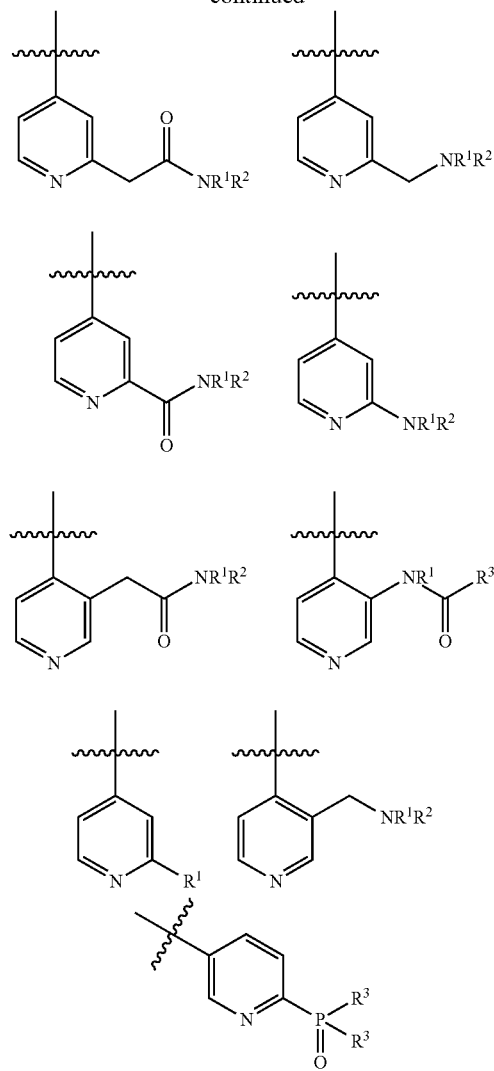

Specific, non-limiting illustrative examples of this class include compounds of formula IA, LB or IC in which substituted $W^1$ is of the following formulae:

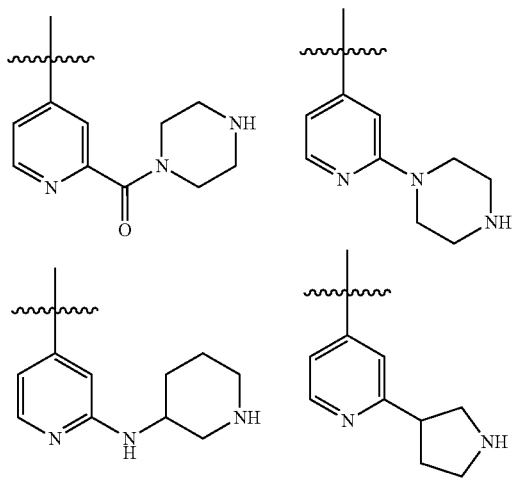

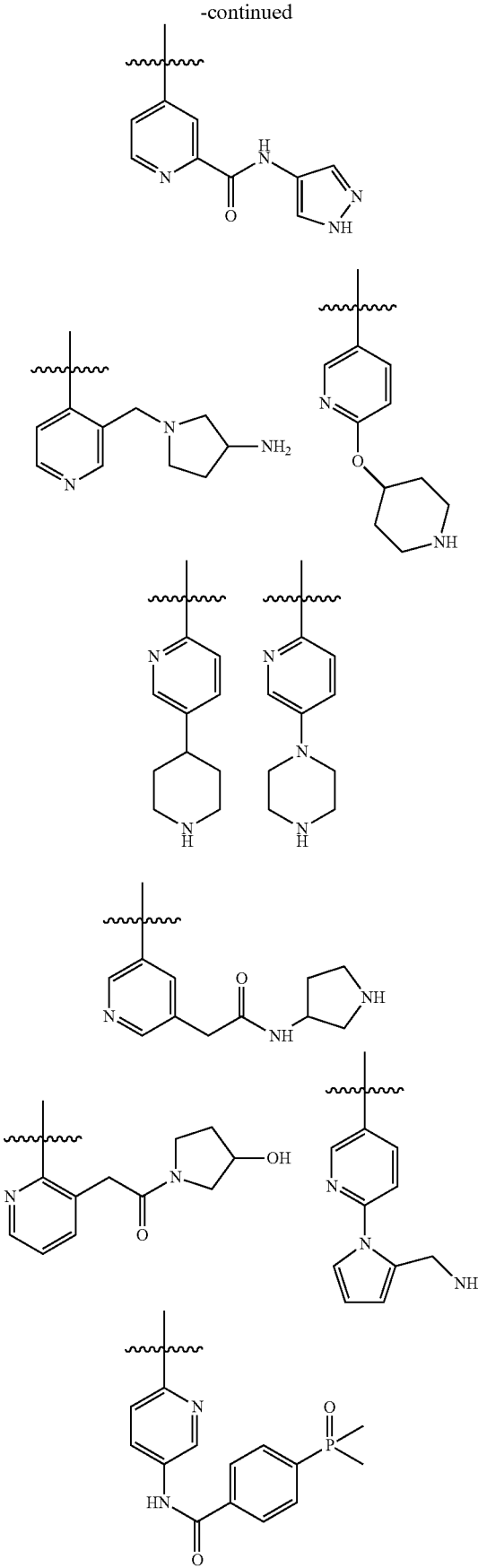
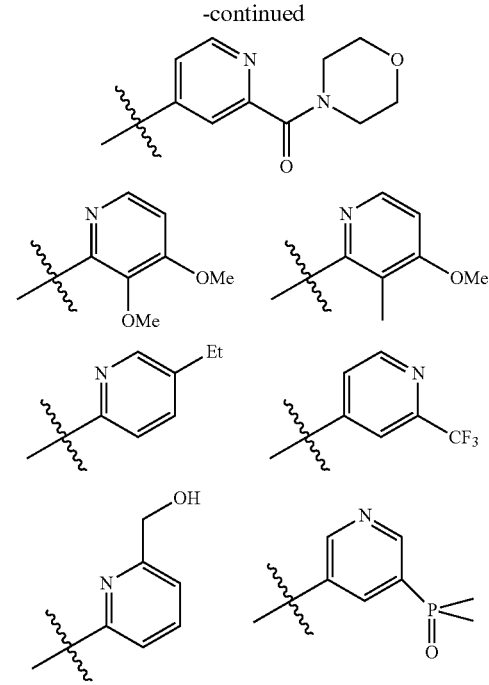
Non-limiting Illustrative examples of this class are compounds of the following formulae:
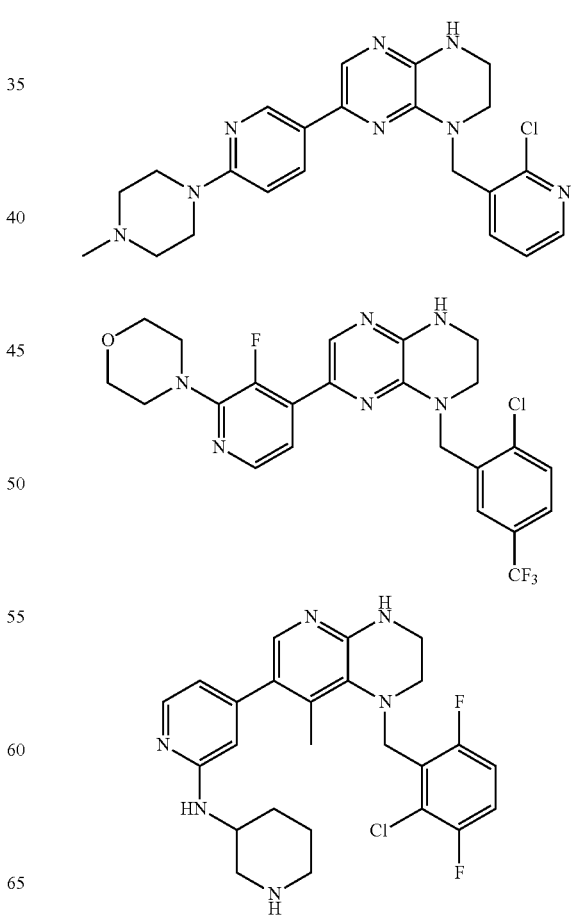

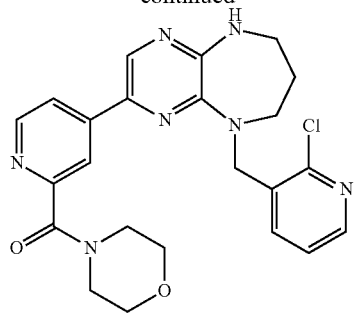
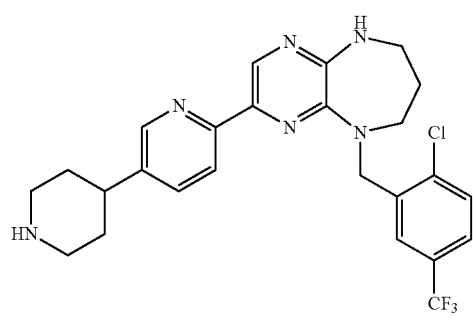
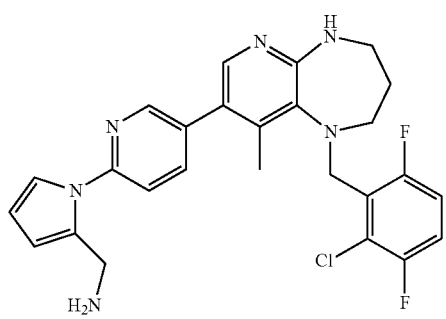
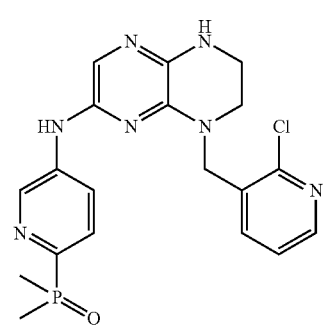
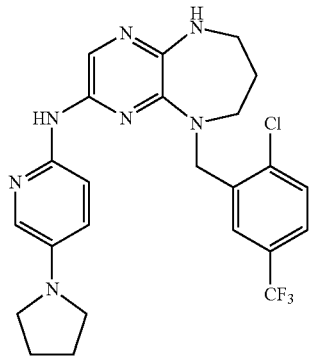
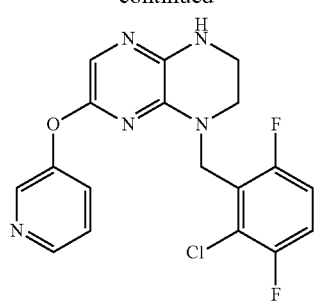
In another embodiment, $W^1$ is a pyrazine substituted with 1-3 $R^a$: Non-limiting examples of this class of compounds in which $W^1$ is:
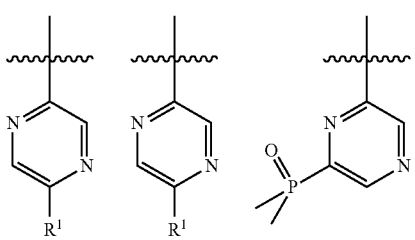
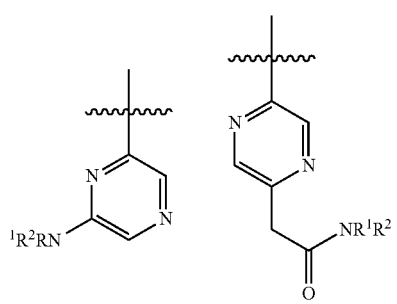
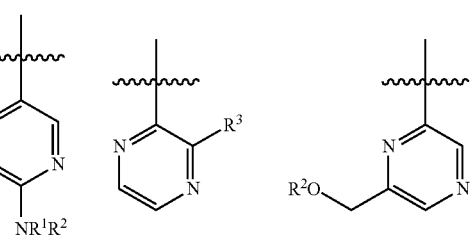
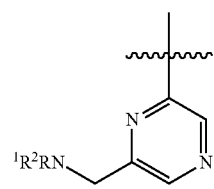
Specific, non-limiting illustrative examples of this class include compounds of formula IA, IB or IC in which substituted $W^1$ is of the following formulae:

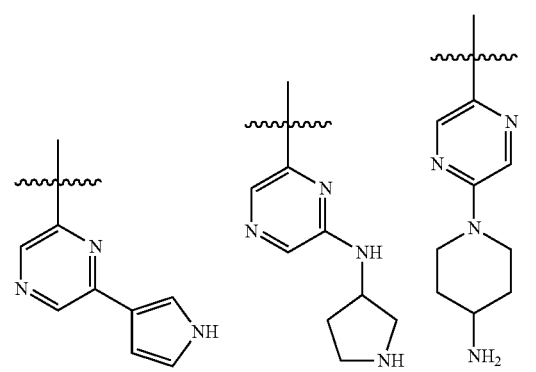
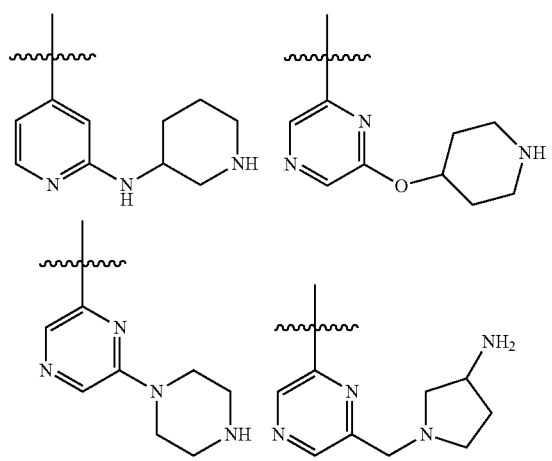
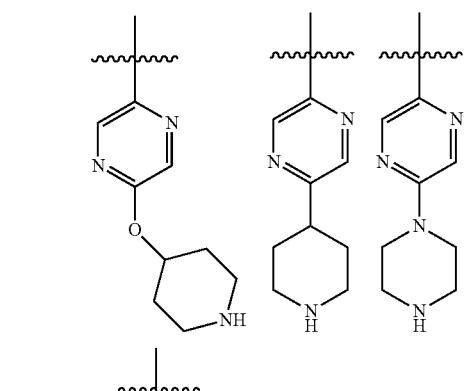
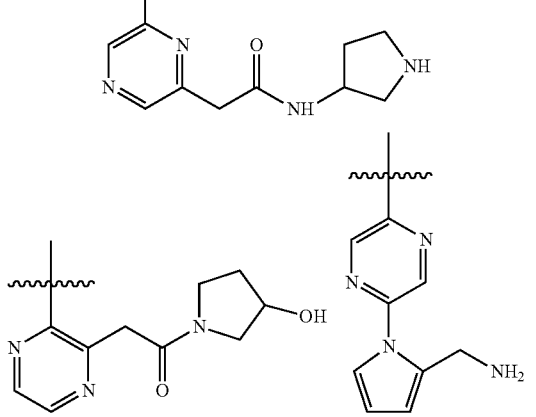
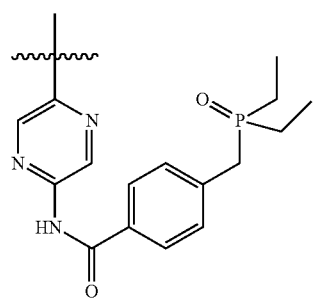 [SMILES: *c1cnc(NC(=O)c2ccc(CP(=O)(CC)CC)cc2)cn1]

In another embodiment, $W^1$ is a triazine substituted with 1 to 2 $R^a$ groups. Examples include compounds in which $W^1$ has the following formulae:

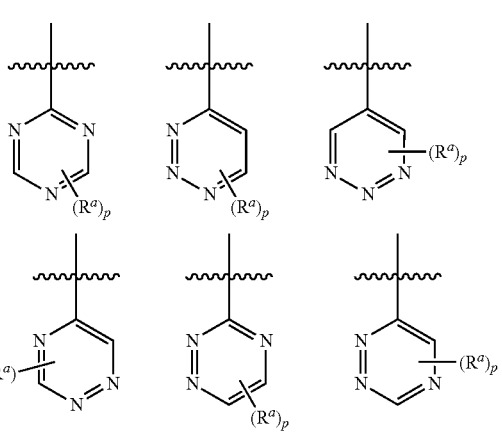

in which p is defined previously and the number of substituents $R^a$ does not exceed the maximum available valencies, which in the triazine case p is 0, 1 or 2.

In one embodiment, two $R^a$ groups form with the atoms to which they are attached, a 5- or 6- or 7-membered saturated, partially saturated or unsaturated ring, which contains 0-3 heteroatoms selected from N, O, P(O) and S(O)$_r$; and the resulting fused ring system is optionally substituted. Non-Limiting examples include compounds of Formula IA or IB or any of the classes and subclasses of this invention in which $W^1$ has the following formulae:

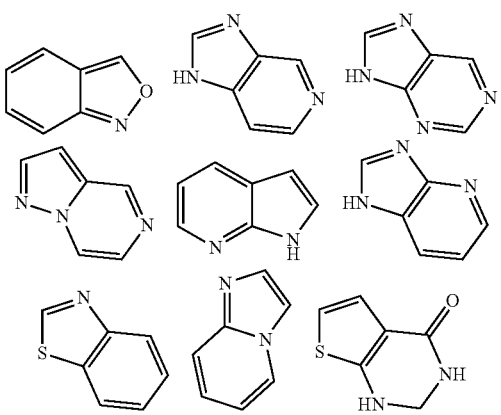

-continued

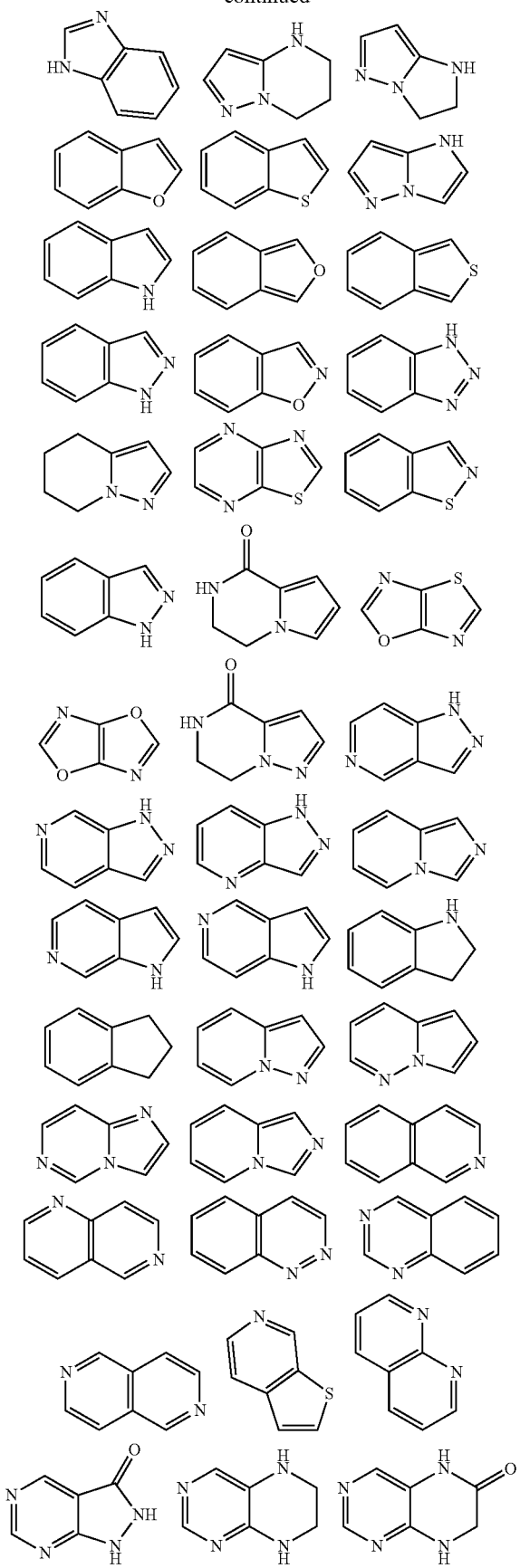

-continued

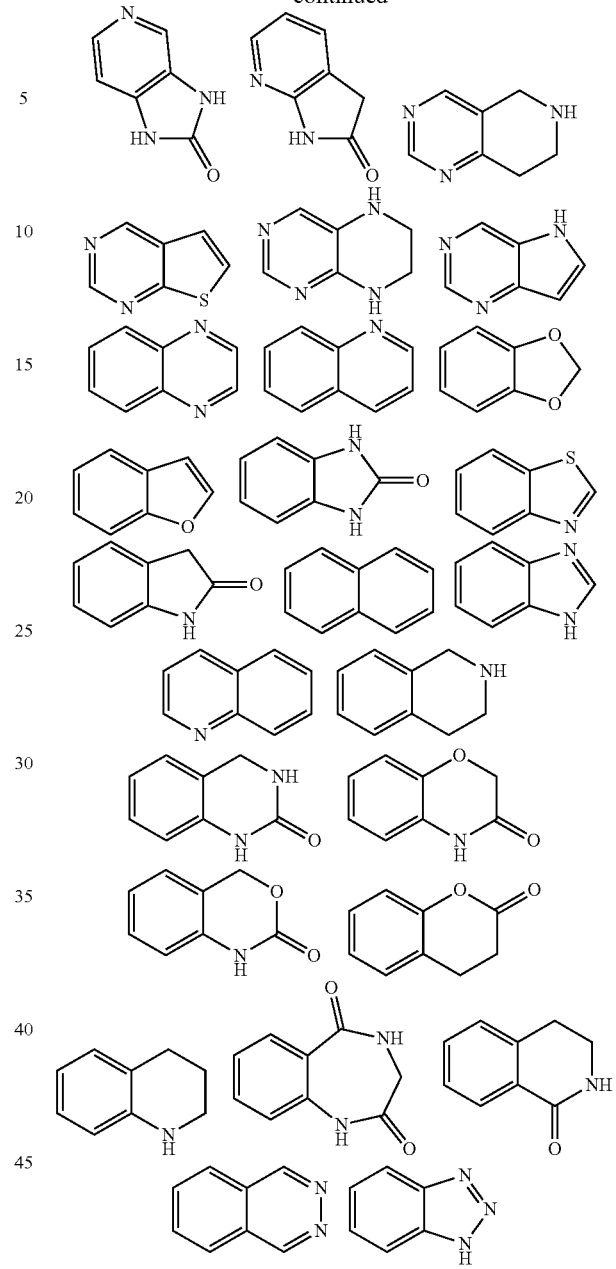

and the depicted fused ring systems are optionally substituted with $R^d$, which is selected from the group consisting of halo, $=O$, $=S$, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C($=$S)$YR^2$, —OC($=$S)$YR^2$, —C($=$S)$YR^2$, —YC($=NR^1$)$YR^2$, —YC($=$N—$OR^1$)$YR^2$, —YC($=$N—$NR^1R^2$)$YR^2$, —YP($=$O)($YR^3$)($YR^3$), —Si($R^3$)$_3$, —$NR^1SO_2R^2$, —S(O)$_rR^2$, —$SO_2NR^1R^2$ and —$NR^1SO_2NR^1R^2$, in which $R^1$, $R^2$, $R^3$, Y and r are previously defined.

Additionally the depicted hydrogen can also be replaced by an $R^d$ group; or the nitrogen bearing the depicted hydrogen can be the point of attachment to the core molecule (i.e the nitrogen is attached to $L^1$ and the depicted hydrogen is therefore absent).

Specific, non-limiting illustrative examples of this class include compounds of formula IA, D3 or IC or other classes and subclasses of this invention, in which substituted $W^1$ is of the following formulae:
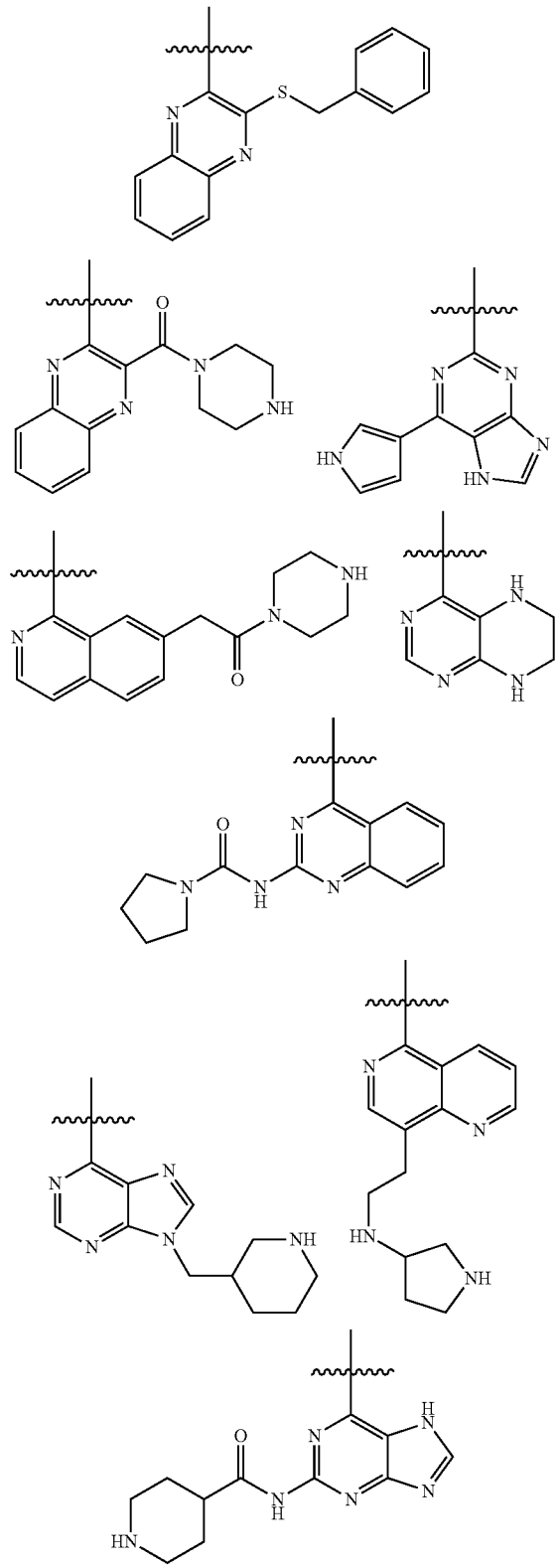
-continued
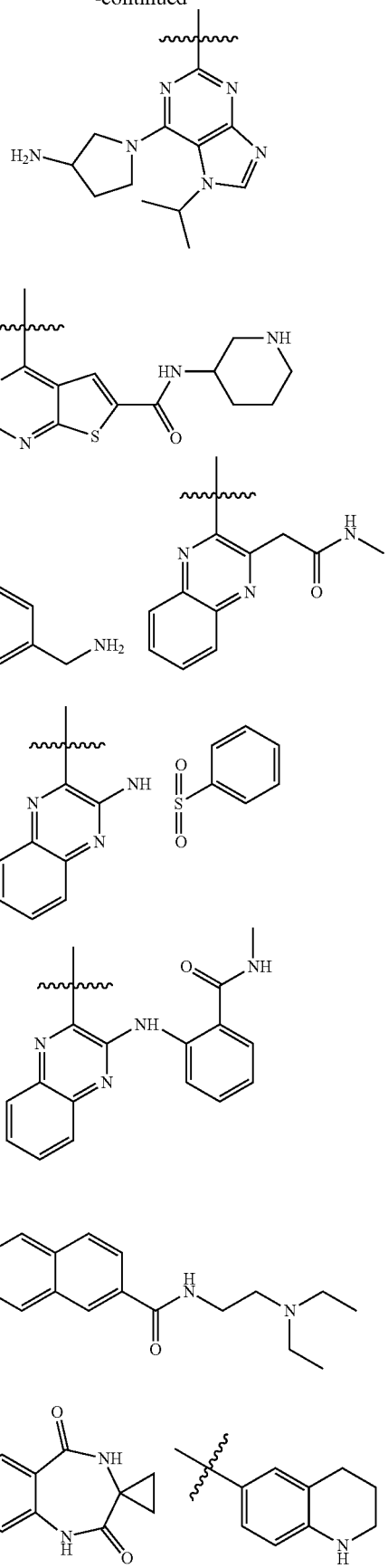

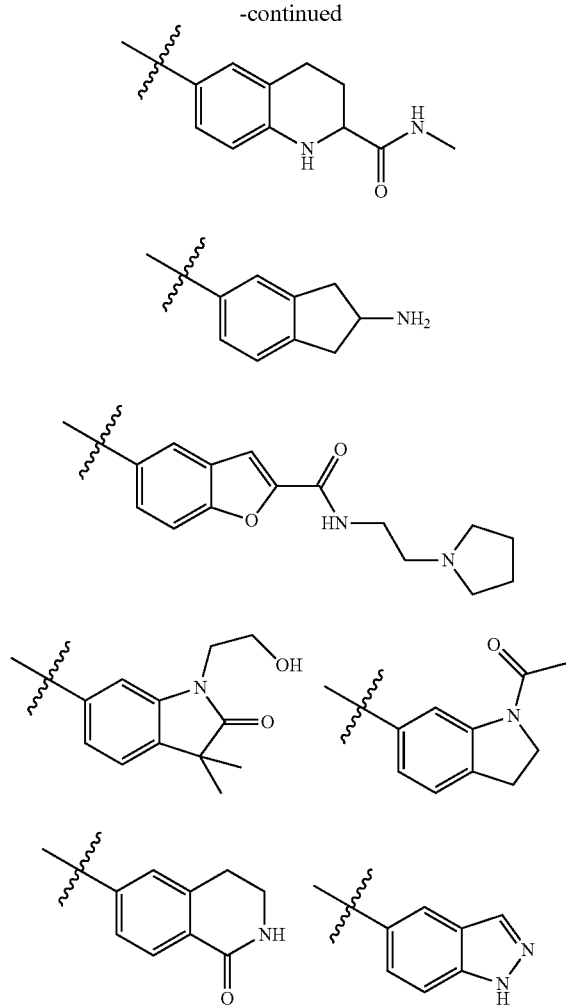

For the previously described classes and subclasses of compounds, as in all compounds of the invention, Q, $L^2$ and $W^2$ are defined as in part 1.

In one embodiment of this invention are compounds of Formulae I, IA, IB or IC in which $L^2$ is $C(O)C_{0-6}$alkyl. Of further interest are compounds of this class in which $L^2$ is $C(O)CH_2$ or $C(O)$.

In another embodiment of this invention are compounds of Formulae I, IA, IB or IC in which $L^2$ is $C_{0-6}$alkyl. Of further interest are compounds of this class in which $L^2$ is $CH_2$ or $CH(CH_3)$.

In some embodiment of this invention are compounds of Formulae I, IA, IB, IC or ID or any other classes or subclasses of this invention in which $W^2$ is a phenyl substituted with 1-5 $R^b$.

In some other embodiment are compounds of formulae IA, IB, IC or ID in which $W^2$ is a 6-membered ring heteroaryl. Examples of this class are compounds of the above classes and subclasses in which $W^2$ is a pyridine, pyrazine, pyridazine, pyrimidine or triazine optionally substituted with 1-4 $R^b$.

In other embodiment are compounds of formulae IA, IB, IC or ID in which $W^2$ is a 5-membered ring heteroaryl. Examples of this class are compounds of the above classes and subclasses in which $W^2$ is imidazole, pyrazole, tetrazole, oxazole, thiazole, isoxazole, pyrolle, or the like and $W^2$ is optionally substituted with 1-3 $R^b$.

Of particular interest is a class of compounds as described above in which $R^b$ is selected from the group consisting of halo, —$R^1$, —$OR^2$, —$NR^1R^2$, —$NR^1C(O)R^2$, —$NR^1C(O)NR^2$, $C(O)NR^1R^2$, $C(O)OR^1$, —$SO_2NR^1R^2$, —$SO_2R^1$, —$NR^1SO_2R^2$ or $P=O(R^3)_2$. In another subclass of interest, are compounds of the above embodiment in which $R^b$ is alkyl, alkynyl, halo, aryl, heteroaryl, heterocyclyl, O-alkyl (i.e: OMe and the like), —CN, —C(O)NH-alkyl, —C(O)NH-aryl, C(O)NH-heterocyclyl, OH, —$NR^1R^2$, NHS(O)$_2$-alkyl, NHS(O)$_2$-aryl or P(=O)(alkyl)$_2$. Non limiting examples of $R^b$ are is H, F, Cl, Br, $CF_3$, $OCF_3$, —$(CH_2)_yC(=O)NR^1R^2$, —$(CH_2)_yC(=O)$aryl, —$SO_2NR^1R^2$, $NHSO_2R^1$, lower alkyl, —$(CH_2)_yC(=O)$heteroaryl, —$(CH_2)_yC(=O)$heterocyclyl, —$(CH_2)_yNHC(=O)R^2$, —$(CH_2)_yNR^1R^2$, —$(CH_2)_yOR^2$, —$(CH_2)_ySR^2$, —$(CH_2)_y$heterocyclyl, —$(CH_2)_y$aryl, —$(CH_2)_y$heteroaryl, NH-aryl, NH-heteroaryl, NH-heterocyclyl and —$(CH_2)_mP(=O)(Me)_2$, —$(CH_2)_mP(=O)(Et)_2$, in which y and m are independently selected from 0, 1, 2, 3 and 4; and alkyl include straight (i.e. unbranched or acyclic), branched and cyclic alkyl groups and alkyl, aryl, heteroaryl, heterocyclyl groups are optionally substituted.

Of current special interest is a class of compounds of formulae IA, IB, IC or ID and other classes and subclasses of this invention in which $R^b$ is selected from H, halo, lower alkyl (i.e: methyl, ethyl, cyclopropyl and the like), —$CF_3$, —$OCF_3$, —CN, —NH(alkyl), alkenyl and alkynyl (i.e: acetylene). Of other current interest are compounds of this class in which $R^b$ is H, halo, lower alkyl or $CF_3$.

In a particular embodiment of the previous classes and subclasses, one of $R^a$ is or $R^b$ contains YP(O)(YR$^3$)$_2$ group and more preferably a P(O)(R$^3$)$_2$ group. Examples of $R^a$ or $R^b$ containing P(O)(R$^3$)$_2$ groups are without limitation —$(CH_2)_m$—P(=O)(R$^3$)$_2$, —$(CH_2)_m$—NR$^1$—P(=O)(R$^3$)$_2$, —$(CH_2)_m$—O—P(=O)(R$^3$)$_2$, —$(CH_2)_m$—NR$^1$—$(CH_2)_m$—P(=O)(R$^3$)$_2$, —$(CH_2)_m$—NR$^1$C(O)O—$(CH_2)_m$—P(=O)(R$^3$)$_2$, —$(CH_2)_m$—C(O)—$(CH_2)_m$—P(=O)(R$^3$)$_2$, —$(CH_2)_m$—C(O)NR$^1$—$(CH_2)_m$—(P=O)(R$^3$)$_2$ in which m is 0, 1, 2, 3 or 4.

Illustrative examples of this class are compounds of Formula IA, IB, IC or ID of the following types:

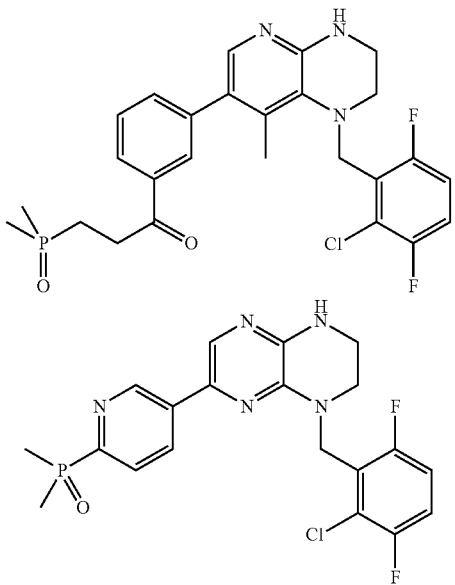

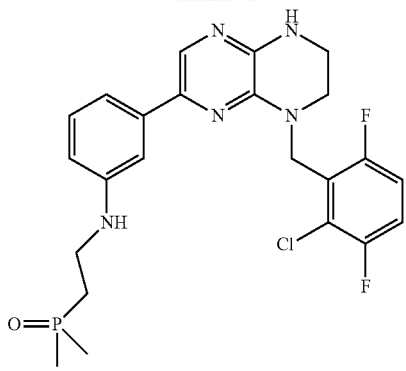

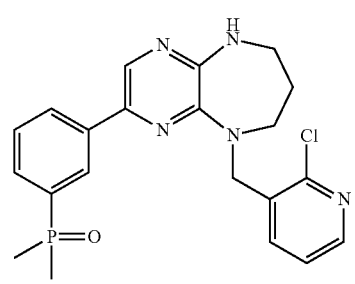

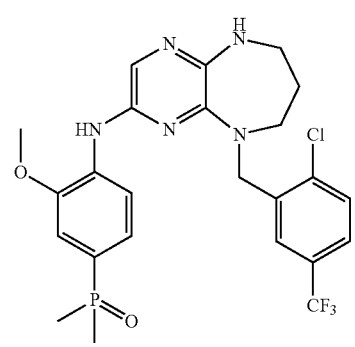

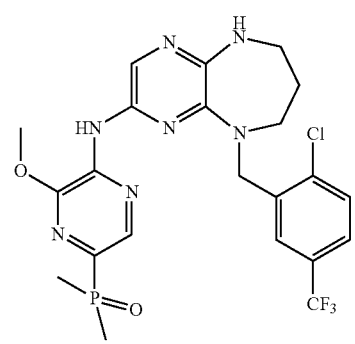 [SMILES: COc1nc(P(C)(C)=O)cnc1Nc1cnc2c(n1)N(Cc1cc(C(F)(F)F)ccc1Cl)CCCN2]

In some embodiment, a $R^a$ or $R^b$ containing $P(O)(R^3)_2$ substituent can be of cyclic structure.

In some non-limiting cases, two $R^3$ groups can form with the phosphine atom to which they are attached a 5-, 6- or 7-membered saturated ring, optionally substituted; and which can optionally contain one heteroatom selected from N, O and $S(O)_r$.

Non limiting examples of this embodiment include compounds in which $R^a$ or $R^b$ containing $P(O)(R^3)_2$ group is of the following formula:

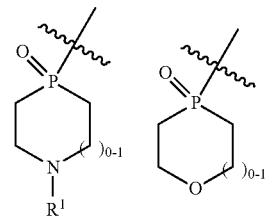

Illustrative examples of this class are compounds of Formula IA or IB of the following types:

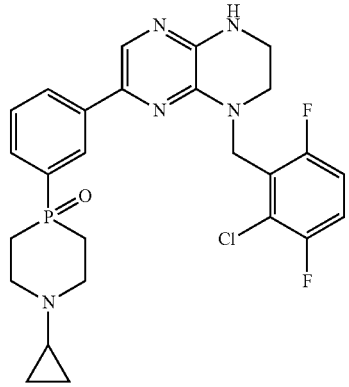

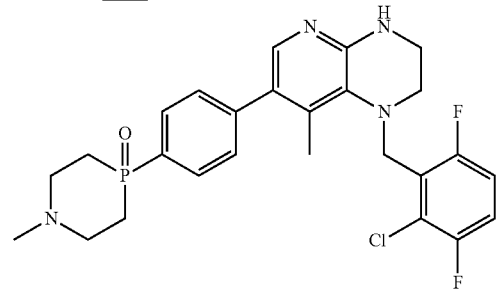

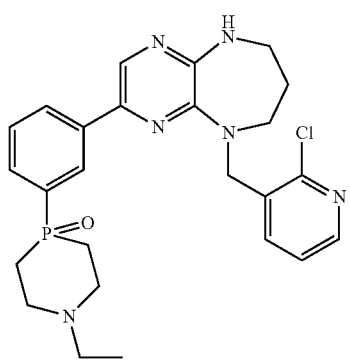

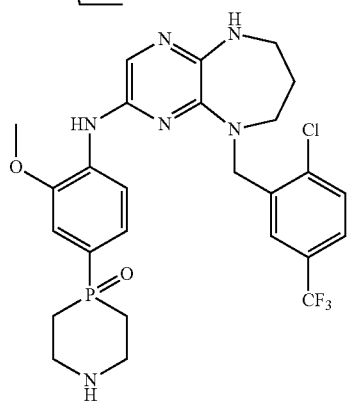

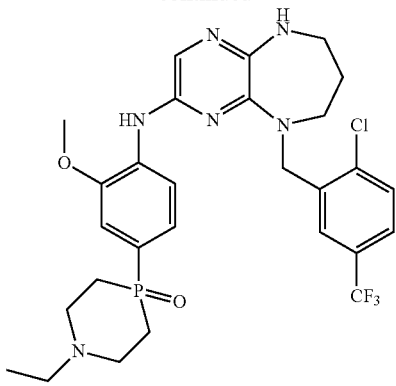

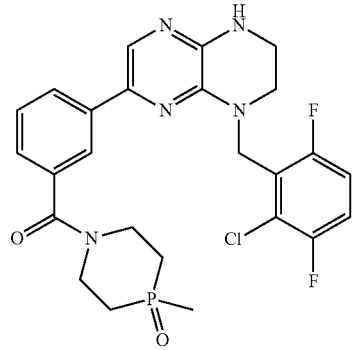

In other cases, $R^a$ or $R^b$ group can be a 5-, 6- or 7-membered saturated ring, optionally substituted; which contains a phosphorous atom and can optionally contains 1 heteroatom selected from N, O and $S(O)_r$. Non limiting examples of this embodiment include compounds in which $R^a$- or $R^b$-containing $P(O)(R^3)_2$ group is of the following formulae:

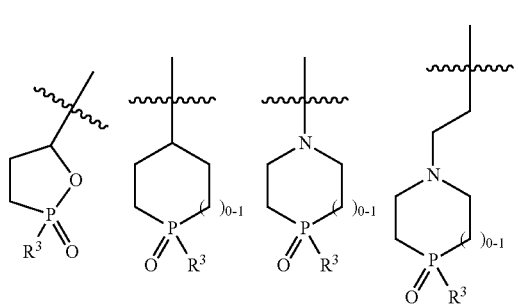

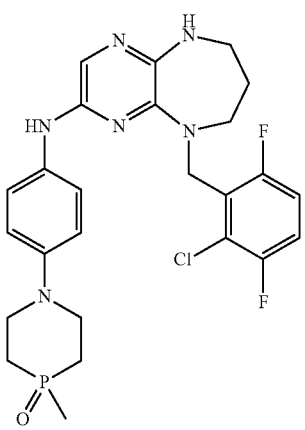

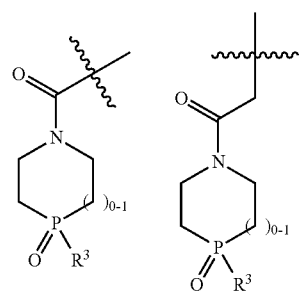

Illustrative examples of this class are compounds of Formula IA, IC or ID of the following types:

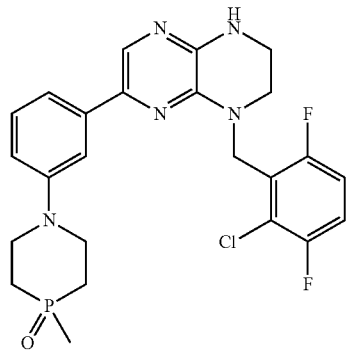

Of special interest for use in this invention are compounds of formula IA or IB in which $L^2$ is $CH_2$ or $CH(CH_3)$. Of further interest are compounds of this class in which $L^1$ is a bond NH, C(O), C(O)NH, $C(O)NHC_{1-6}$alkyl, $CH_2NH$, O or S. Illustrative, non-limiting examples of this subclass are compounds of the following formulae:

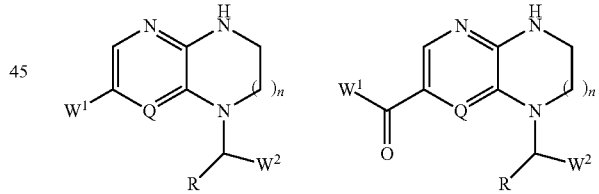

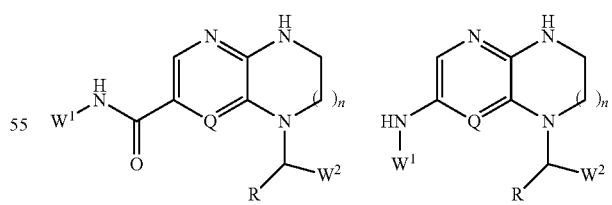

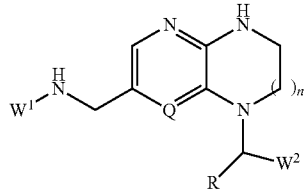

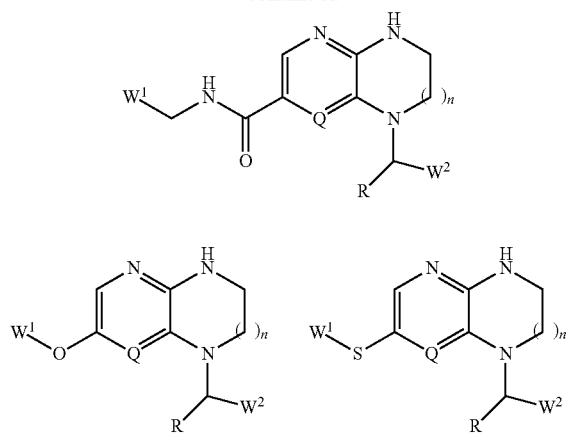

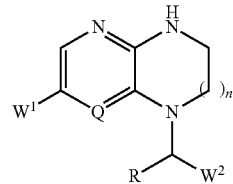

Formula ID in which R is H or CH$_3$; and W$^1$, W$^2$, Q and n are as previously defined in part 1.

In one particular aspect of this embodiment, are compounds of formula ID in which Q is N.

In another aspect of this embodiment are compounds of formula ID in which Q is CR$^c$, in which R$^c$ is for example lower alkyl or halo.

in which R is H or CH$_3$; and Q, W$^1$ and W$^2$ are previously defined. Of further interest are compounds of these formulae in which n is 1. Of other interest are compounds of these formulae in which n is 2.

In another aspect of this embodiment are compounds of formula ID in which n is 0.

In another aspect of this embodiment are compounds of formula ID in which n is 1.

Of particular current interest are compounds of Formula IA, IB, IC or ID in which L$^2$ is CH$_2$ or CH(CH$_3$); W$^1$ and W$^2$ are phenyls: non limiting examples of this subclass are compounds of the following formulae:

Of particular current interest are compounds of the above classes and subclasses in which L$^2$ is CH$_2$ or CH(CH$_3$); W$^2$ is phenyl and W$^1$ is a 5-, 6- or 7-membered heterocyclyl. Illustrative, non-limiting examples of this subclass are compounds of the following formulae:

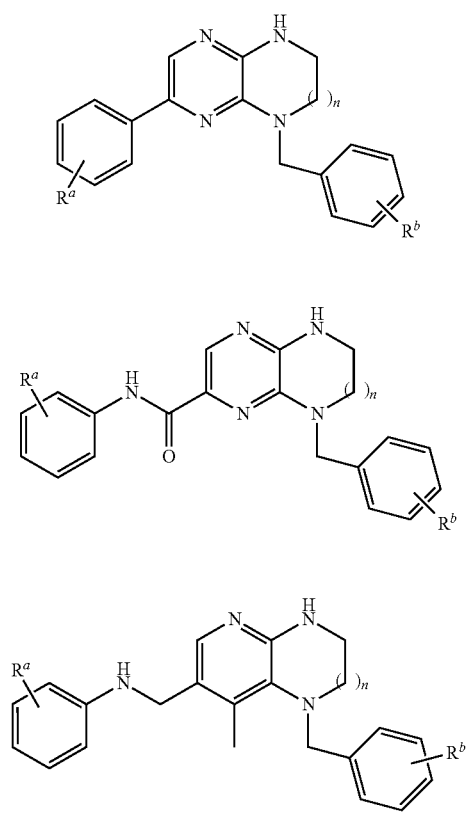

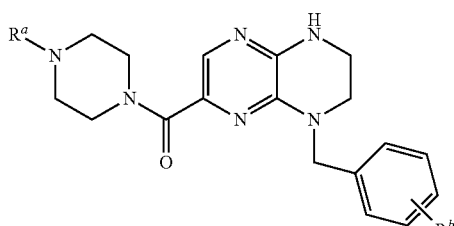

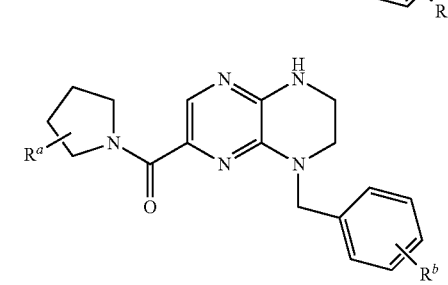

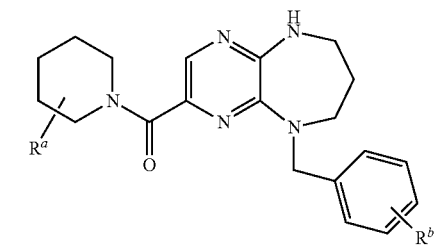

Of particular interest of the previous embodiment are compounds of Formulae IC in which L$^2$ is C$_{0-6}$alkyl. Of further interest are compounds of this class in which L$^2$ is CH$_2$ or CH(CH$_3$). This class is represented by compound of Formula ID:

Of particular current interest are compounds of the above classes and subclasses in which L$^2$ is CH$_2$ or CH(CH$_3$); W$^2$ is a phenyl and W$^1$ is a 5- or 6-membered ring heteroaryl. Illustrative, non-limiting examples of this subclass are compounds of the following formulae:

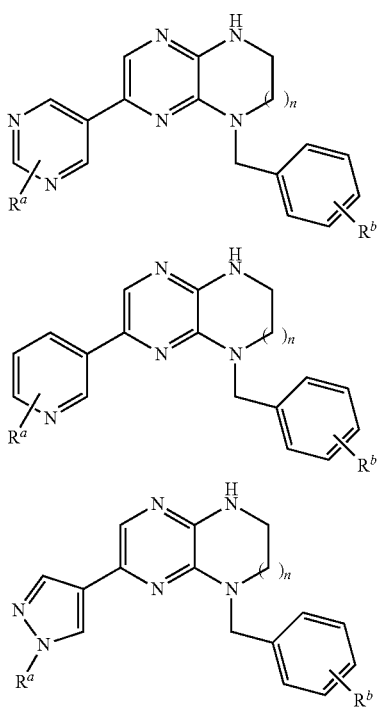

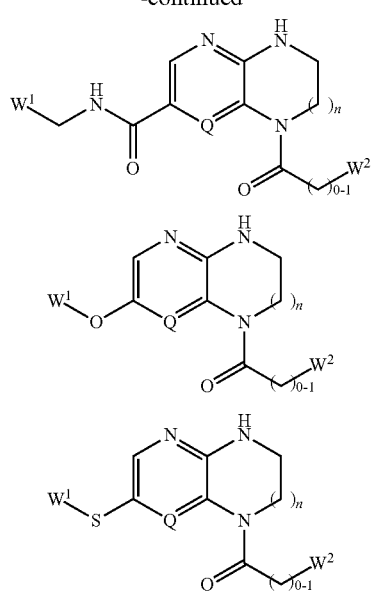

Of further interest are compounds of these formulae in which n is 1. Of other interest are compounds of these formulae in which n is 2.

Of special interest for use in this invention are compounds of formula IA or IB in which $L^2$ is $C(O)$ or $C(O)CH_2$. Of further interest are compounds of this class in which $L^1$ is a bond NH, C(O), C(O)NH, C(O)NHC$_{1-6}$alkyl, CH$_2$NH, O or S. Illustrative, non-limiting examples of this subclass are compounds of the following formulae:

Of special interest for use in this invention are compounds of formula IA or IB in which $L^2$ is $SO_2$. Of further interest are compounds of this class in which $L^1$ is a bond NH, C(O), C(O)NH, C(O)NHC$_{1-6}$alkyl, CH$_2$NH, O or S. Illustrative, non-limiting examples of this subclass are compounds of the following formulae:

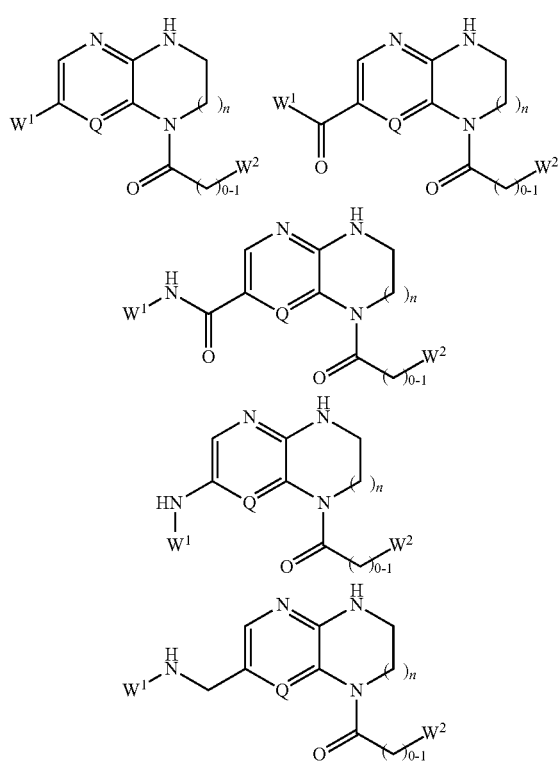

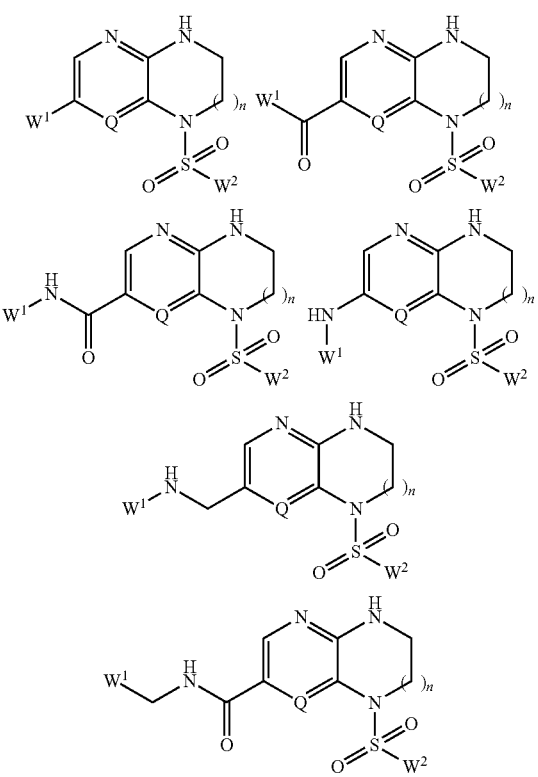

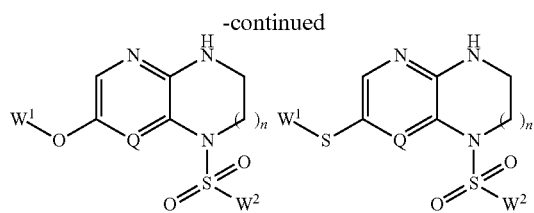

Of further interest are compounds of these formulae in which n is 1. Of other interest are compounds of these formulae in which n is 2.

In one embodiment of this invention are compounds of formula IA, IB, IC and ID and of all previously described classes and subclasses, in which Q is N.

In another embodiment of this invention are compounds of formula IA, IB, IC and ID and of all previously described classes and subclasses, in which Q is $CR^c$. Of further interest are compound of this class in which $R^c$ is selected from small alkyl (i.e: methyl, ethyl and the like) and halo.

Compounds of this invention of particular interest include those with on or more of the following characteristics:
- a molecular weight of less than 1000, preferably less than 750 and more preferably less than 600 mass units (not including the weight of any solvating or co-crystallizing species, of any counter-ion in the case of a salt); or
- inhibitory activity against a wild type or mutant (especially a clinically relevant mutant) kinase, especially a kinase such as Alk, Met, Jak2, bRaf, EGFR, Tie-2, FLT3 or another kinase of interest with an $IC_{50}$ value of 1 μM or less (as determined using any scientifically acceptable kinase inhibition assay), preferably with an $IC_{50}$ of 500 nM or better, and optimally with an $IC_{50}$ value of 250 nM or better; or
- inhibitory activity against a given kinase with an IC50 value at least 100-fold lower than their $IC_{50}$ values for other kinases of interest; or
- inhibitory activity for Alk, Met, Jak2 or B-Raf with a 1 μM or better $IC_{50}$ value against each; or
- a cytotoxic or growth inhibitory effect on cancer cell lines maintained in vitro, or in animal studies using a scientifically acceptable cancer cell xenograft model, (especially preferred are compounds of the invention which inhibit proliferation of Ba/F3 NMP-ALK, Ba/F3 EML4-ALK, Karpas 299 and/or SU-DHL-1 cells with a potency at least as great as the potency of known alk inhibitors such as NVP-TAE684 and PF2341066 among others, preferably with a potency at least twice that of known alk inhibitors, and more preferably with a potency at least 10 times that of known alk inhibitors as determined by comparative studies.

Also provided is a composition comprising at least one compound of the invention or a salt, hydrate or other solvate thereof, and at least one pharmaceutically acceptable excipient or additive. Such compositions can be administered to a subject in need thereof to inhibit the growth, development and/or metastasis of cancers, including solid tumors (e.g., prostate cancer, colon cancer, pancreatic and ovarian cancers, breast cancer, non small cell lung cancer (NSCLS), neural tumors such as glioblastomas and neuroblastomas; esophageal carcinomas, soft tissue cancers such as rhabdomyosarcomas; among others); various forms of lymphoma such as a non-Hodgkin's lymphoma (NHL) known as anaplastic large-cell lymphoma (ALCL), various forms of leukemia; and including cancers which are resistant to other treatment, including those which are resistant to treatment with another kinase inhibitor, and generally for the treatment and prophylaxis of diseases or undesirable conditions mediated by one or more kinases which are inhibited by a compound of this invention.

The cancer treatment method of this invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue (MW>300) thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of this invention with enhanced aqueous solubility or active transport through the gut membrane, relative to the parent compound.

One important aspect of this invention is a method for treating cancer in a subject in need thereof, which comprises administering to the subject a treatment effective amount of a composition containing a compound of this invention. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of this invention.

Such other drugs include but not limited to one or more of the following: an anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 6-Mercaptopurine, 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide and Megestrol); mTOR inhibitor (e.g., Sirolimus (rapamycin), Temsirolimus (CCI779), Everolimus (RAD001), AP23573 or other compounds disclosed in U.S. Pat. No. 7,091,213); proteasome inhibitor (such as Velcade, another proteasome inhibitor (see e.g., WO 02/096933) or another NF-kB inhibitor, including, e.g., an IkK inhibitor); other kinase inhibitors (e.g., an inhibitor of Src, BRC/Abl, kdr, flt3, aurora-2, glycogen synthase kinase 3 ("GSK-3"), EGF-R kinase (e.g., Iressa, Tarceva, etc.), VEGF-R kinase, PDGF-R kinase, etc); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference. Examples of other therapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or another bisphosphonate.

This invention further comprises the preparation of a compound of any of Formulae I, IA, IB, IC, ID or of any other classes and subclasses of compounds of this invention.

The invention also comprises the use of a compound of the invention, or a pharmaceutically acceptable derivative thereof, in the manufacture of a medicament for the treatment either acutely or chronically of cancer (including lymphoma and solid tumors, primary or metastatic, including cancers such as noted elsewhere herein and including cancers which are resistant or refractory to one or more other therapies). The compounds of this invention are useful in the manufacture of an anti-cancer medicament. The compounds of the present invention are also useful in the manufacture of a medicament to attenuate or prevent disorders through inhibition of one or more kinases such as ALK, jak2, b-raf, met, Tie-2, EGFR, FLT3, FAK, Pim-1, Pl3k, etc.

This invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of this invention are also useful as standards and reagents for characterizing various kinases, especially but not limited to ALK, Met, Jak2, b-Raf, Tie-2, EGFR, FLT3 among others as well as for studying the role of such kinases in biological and pathological phenomena; for studying intracellular signal transduction pathways mediated by such kinases, for the comparative evaluation of new kinase inhibitors; and for studying various cancers in cell lines and animal models.

3. Definitions

In reading this document, the following information and definitions apply unless otherwise indicated.

The term "Alkyl" is intended to include linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_{1-6}$ alkyl is intended to include $C_1$, $C_2$, $C_3$, $C_4$, $C_5$, and $C_6$ alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "Alkoxy" represents a subset of alkyl in which an alkyl group as defined above with the indicated number of carbons attached through an oxygen bridge. For example, "alkoxy" refers to groups —O-alkyl, wherein the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

"Haloalkyl" is intended to include both branched and linear chain saturated hydrocarbon having one or more carbon substituted with a Halogen. Examples of haloalkyl, include, but are not limited to, trifluoromethyl, trichloromethyl, pentafluoroethyl and the like.

The term "alkenyl" is intended to include hydrocarbon chains of linear, branched, or cyclic configuration having one or more unsaturated Carbon-carbon bonds that may occur in any stable point along the chain or cycle. Unless otherwise specified, "alkenyl" refers to groups usually having two to eight, often two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. Furthermore, alkenyl groups may be substituted or unsubstituted.

The term "alkynyl" is intended to include hydrocarbon chains of either linear or branched configuration, having one or more carbon-carbon triple bond that may occur in any stable point along the chain. Unless otherwise specified, "alkynyl" groups refer refers to groups having two to eight, preferably two to six carbons. Examples of "alkynyl" include, but are not limited to prop-2-ynyl, but-2-ynyl, but-3-ynyl, pent-2-ynyl, 3-methylpent-4-ynyl, hex-2-ynyl, hex-5-ynyl, etc. Furthermore, alkynyl groups may be substituted or unsubstituted.

Cycloalkyl is a subset of alkyl and includes any stable cyclic or polycyclic hydrocarbon groups of from 3 to 13 carbon atoms, any of which is saturated. Examples of such cycloalkyl include, but are not limited to cyclopropyl, norbornyl, [2.2.2]bicyclooctane, [4.4.0]bicyclodecane, and the like, which, as in the case of other alkyl moieties, may optionally be substituted. The term "cycloalkyl" may be used interchangeably with the term "carbocycle".

Cycloalkenyl is a subset of alkenyl and includes any stable cyclic or polycyclic hydrocarbon groups of from 3 to 13 carbon atoms, preferably from 5 to 8 carbon atoms, which contains one or more unsaturated carbon-carbon double bonds that may occur in any point along the cycle. Examples of such cycloalkenyl include, but are not limited to cyclopentenyl, cyclohexenyl and the like.

Cycloalkynyl is a subset of alkynyl and includes any stable cyclic or polycyclic hydrocarbon groups of from 5 to 13 carbon atoms, which contains one or more unsaturated carbon-carbon triple bonds that may occur in any point along the cycle. As in the case of other alkenyl and alkynyl moieties, cycloalkenyl and cycloalkynyl may optionally be substituted.

"Heterocycle", "heterocyclyl", or "heterocyclic" as used herein refers to non-aromatic ring systems having five to fourteen ring atoms, preferably five to ten, in which one or more ring carbons, preferably one to four, are each replaced by a heteroatom such as N, O, or S, Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and may comprise one or more rings. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl, imidazo[1,2-a]pyrimidyl, imidazo[1,2-a]pyrazinyl, imidazo[1,2-a]pyiridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, pyrrolo[2,3-d]pyrimidyl, triazolopyrimidyl, pyridopyrazinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen (F, Cl, Br or I), alkyl, alkenyl, alkynyl, —CN, —$R^1$, —$OR^2$, —$S(O)_rR^2$, (wherein r is an integer of 0, 1 or 2), —$SO_2NR^1R^2$, —$NR^1R^2$, —O—$NR^1R^2$, —$NR^1$—$NR^1R^2$, —(CO)$YR^2$, —O(CO)$YR^2$, —$NR^1$(CO)$YR^2$, —S(CO)$YR^2$, —$NR^1$C(=S)$YR^2$, —OC(=S)$YR^2$, —C(=S)$YR^2$, wherein each occurrence of Y is independently —O—, —S—, —NR$^1$—, or a chemical bond; —(CO)YR$^2$ thus encompasses —C(=O)R$^2$, —C(=O)OR$^2$, and —C(=O)NR$^1$R$^2$. Additional substituents include —YC(=NR$^1$)YR$^2$, —YC(=N—OR$^1$)YR$^2$, —YC(=N—NR$^1$R$^2$)YR$^2$, —COCOR$^2$, —COM-COR$^2$ (where M is a 1-6 carbon alkyl group), —YP(=O)(YR$^3$)(YR$^3$) (including among others —P(=O)(R$^3$)$_2$), —Si(R$^3$)$_3$, —NO$_2$, —NR$^1$SO$_2$R$^2$ and —NR$^1$SO$_2$NR$^1$R$^2$. To illustrate further, substituents in which Y is —NR$^1$ thus include among others, —NR$^1$C(=O)R$^2$, —NR$^1$C(=O)NR$^1$R$^2$, —NR$^1$C(=O)OR$^2$, and —NR$^1$C(=NH)NR$^1$R$^2$. R$^3$ substituent is selected from alkyl, alkenyl, alkynyl, cycloalkyl, cycloalkenyl, cycloalkynyl, aryl, heteroaryl, heterocyclyl; R$^1$ and R$^2$ substituents at each occurrence are independently selected from hydrogen, alkyl, alkenyl, alkynyl, cycloalkyl, cycloalkenyl, cycloalkynyl, aryl, heteroaryl, heterocyclyl, and R$^1$, R$^2$ and R$^3$ substituents may themselves be substituted or unsubstituted. Examples of substituents allowed on R$^1$, R$^2$ and R$^3$ include, among others amino, alkylamino, dialkylamino, aminocarbonyl, halogen, alkyl, aryl, heteroaryl, carbocycle, heterocycle, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, haloalkoxy groups. Additional illustrative examples include protected OH (such as acyloxy), phenyl, substituted phenyl, —O-phenyl, —O-(substituted) phenyl, -benzyl, substituted benzyl, —O-phenethyl (i.e., —OCH$_2$CH$_2$C$_6$H$_5$), —O-(substituted)phenethyl. Non-limiting illustrations of a substituted R$^1$, R$^2$ or R$^3$ moiety include haloalkyl and trihaloalkyl, alkoxyalkyl, halophenyl, -M-heteroaryl, -M-heterocycle, -M-aryl, -M-OR$^2$, -M-SR$^2$, -M-NR$^1$R$^2$, -M—OC(O)NR$^1$R$^2$, -M-C(=NR$^2$)NR$^1$R$^2$, -M-C(=NR$^1$)OR$^2$, -M-P(O)R$^3$R$^3$, Si(R$^3$)$_3$, -M-NR$^1$C(O)R$^2$, -M—NR$^1$C(O)OR$^2$, -M-C(O)R$^2$, -M-C(=S)R$^2$, -M-C(=S)NR$^1$R$^2$, -M-C(O)NR$^1$R$^2$, -M-C(O)NR$^2$-M-NR$^1$R$^2$, -M-NR$^2$C(NR$^1$)NR$^1$R$^2$, -M-NR$^1$C(S)NR$^1$R$^2$, -M-S(O)$_2$R$^1$, -M-C(O)R$^1$, -M-OC(O)R$^1$, -MC(O)SR$^2$, -M-S(O)$_2$NR$^1$R$^2$, —C(O)-M-C(O)R$^2$, -MCO$_2$R$^2$, -MC(=O)NR$^1$R$^2$, -M-C(=NH)NR$^1$R$^2$, and -M—OC(=NH)NR$^1$R$^2$ (wherein M is a 1-6 carbon alkyl group).

Some more specific examples include but are not limited to chloromethyl, trichloromethyl, trifluoromethyl, methoxyethyl, alkoxyphenyl, halophenyl, —CH$_2$-aryl, —CH$_2$-heterocycle, —CH$_2$C(O)NH$_2$, —C(O)CH$_2$N(CH$_3$)$_2$, —CH$_2$CH$_2$OH, —CH$_2$OC(O)NH$_2$, —CH$_2$CH$_2$NH$_2$, —CH$_2$CH$_2$CH$_2$NEt$_2$, —CH$_2$OCH$_3$, —C(O)NH$_2$, —CH$_2$CH$_2$-heterocycle, —C(=S)CH$_3$, —C(=S)NH$_2$, —C(=NH)NH$_2$, —C(=NH)OEt, —C(O)NH-cyclopropyl, C(O)NHCH$_2$CH$_2$-heterocycle, —C(O)NHCH$_2$CH$_2$OCH$_3$, —C(O)CH$_2$CH$_2$NHCH$_3$, —CH$_2$CH$_2$F, —C(O)CH$_2$-heterocycle, —CH$_2$C(O)NHCH$_3$, —CH$_2$CH$_2$P(O)(CH$_3$)$_2$, Si(CH$_3$)$_3$ and the like.

An alkyl, alkenyl, alkynyl, alkoxy, haloalkyl, cycloalkyl, cycloalkenyl, cycloalkynyl or non-aromatic heterocyclic group may thus also contain one or more substituents. Examples of suitable substituents on such groups include, but are not limited to those listed above for the carbon atoms of an aryl or heteroaryl group and in addition include the following substituents for a saturated carbon atom: =O, =S, =NH, =NNR$^2$R$^3$, =NNHCO$_2$R$^2$, =NNHCO$_2$R$^2$, or =NNHSO$_2$R$^2$, wherein R$^2$ and R$^3$ at each occurrence are independently hydrogen, alkyl, alkenyl, alkenyl, alkynyl, cycloalkyl, cycloalkenyl, cycloalkynyl, aryl, heteroaryl, heterocyclyl.

Illustrative examples of substituents on an aliphatic, heteroaliphatic or heterocyclic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, —CN, carboxy, alkoxycarbonyl, alkylcarbonyl, —OH, haloalkoxy, or haloalkyl groups.

Illustrative substituents on a nitrogen, e.g., in an heteroaryl or non-aromatic heterocyclic ring include R$^1$, —NR$^1$R$^2$, —C(=O)R$^2$, —C(=O)OR$^2$, —C(=O)SR$^2$, —C(=O)NR$^1$R$^2$, —C(=NR$^2$)NR$^1$R$^2$, —C(=NR$^2$)OR$^2$, —C(=NR$^1$)R$^3$, —COCOR$^2$, —COMCOR$^2$, —CN, —SO$_2$R$^2$, S(O)R$^2$, —P(=O)(YR$^3$)(YR$^3$), —NR$^1$SO$_2$R$^2$ and —NR$^1$SO$_2$NR$^1$R$^2$, wherein each occurrence of R$^3$ is alkyl, alkenyl, alkynyl, cycloalkkyl, cycloalkenyl, cycloalkynyl, aryl, heteroaryl and heterocyclyl; each occurrence of R$^1$ and R$^2$ is independently hydrogen, alkyl, alkenyl, alkynyl, cycloalkkyl, cycloalkenyl, cycloalkynyl, aryl, heteroaryl and heterocyclyl.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "m" substituents (where "m" ranges from 0 to 5) can have 0 to 5 substituents, whereas it is understood that a pyridinyl ring substituted with "m" substituents has a number of substituents ranging from 0 to 4. The maximum number of substituents that a group in the compounds of the invention may have can be easily determined.

This invention encompasses only those combinations of substituents and variables that result in a stable or chemically feasible compound. A stable compound or chemically feasible compound is one that has stability sufficient to permit its preparation and detection. Preferred compounds of this invention are sufficiently stable that they are not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diasteriomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabelled form, i.e., said compounds may contain one or more atoms containing an atomic mass or mass number different from the atomic mass or mass number: ordinarily found in nature. Radioisotopes of hydrogen, carbon, phosphorous, fluorine and chlorine include $^3$H, $^{14}$C, $^{32}$P, $^{35}$S, $^{43}$F and $^{36}$Cl, respectively. Compounds of this invention which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability.

Radiolabelled compounds of this invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

4. Synthetic Overview

The practitioner has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for the $W^1$, $W^2$, $R^a$, $R^b$, $R^c$, $R^d$, R, Q, n, $L^1$ and $L^2$.

Various synthetic approaches may be used to produce the compounds described herein, including those approaches depicted schematically below. The practitioner will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire contents of these references are hereby incorporated by reference.

Also, one may chose reagents enriched for a desired isotope, e.g. deuterium in place of hydrogen, to create compounds of this invention containing such isotope(s). Compounds containing deuterium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of this invention can be synthesized using the methods described below, together with synthetic methods known in the art of synthetic organic chemistry, or by a variation thereon as appreciated by those skilled in the art. Preferred methods include, but are not limited to those described below. The reactions are preformed in a solvent appropriate to the reagents and materials employed and suitable for the transformation being effected. It will be understood by those skilled in the art of organic synthesis that the functionality present on the molecule should be consistent the transformations proposed. This will sometimes required some judgment to modify the order of the synthetic steps or to select one particular process scheme over another in order to obtain a desired compound of the invention.

A compound of the present invention could be prepared as outlined in Scheme 1 to Scheme 30 and via standard methods known to those skilled in the art.

A compound of Formula I, IA, IC or ID in which $L^1$ is a bond, $L^2$ is $CH_2$ and n is 1 can be prepared in a 5 steps synthesis as shown in Scheme 1. A $L^2$-$W^2$ moiety can first be incorporated by reacting 3,5-dibromopyrazin-2-amine with $NH_2CH_2W^2$ in a suitable solvent such as for example butanol at high temperatures in order to generate intermediate I-1. Intermediate I-1 is then reacted with ethyl chloro(oxo)acetate in the presence of a base (such as for example isopropyldiethylamine) in a suitable solvent such as dichloromethane to generate intermediate I-2. Cyclisation of intermediate I-2 can occurs at high temperature in a suitable solvent such as diglyme to generate intermediate I-3.

Intermediate I-3 can then be reduced using reducing agents such as for example $BH_3.Me_2S$ or DIBAL-H in a suitable solvent (for example THF or dichloromethane) to generate intermediate I-4. The $W^1$ moiety is introduced onto intermediate I-4 using Suzuki coupling conditions. The displacement of the bromide can be accomplished by using an aryl/heteroaryl boronic acid in the presence of a palladium catalyst (such as Pd ($PH_3$)$_4$ and a suitable base and solvent to generate a compound of Formula IA.

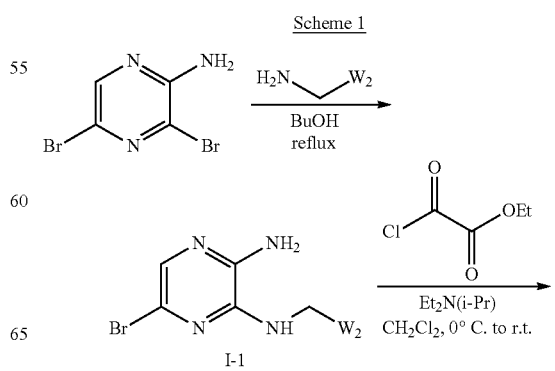

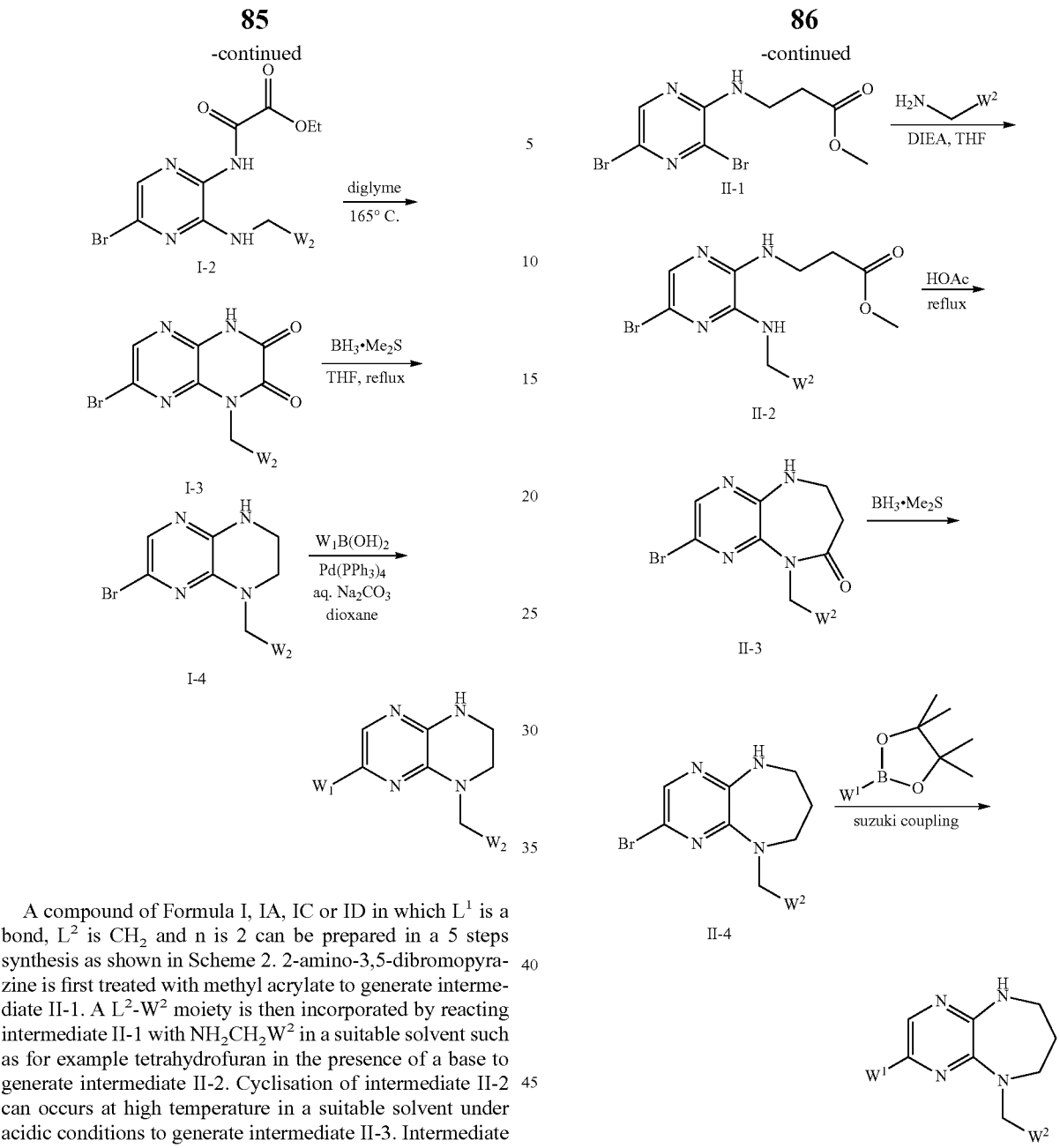

A compound of Formula I, IA, IC or ID in which $L^1$ is a bond, $L^2$ is $CH_2$ and n is 2 can be prepared in a 5 steps synthesis as shown in Scheme 2. 2-amino-3,5-dibromopyrazine is first treated with methyl acrylate to generate intermediate II-1. A $L^2$-$W^2$ moiety is then incorporated by reacting intermediate II-1 with $NH_2CH_2W^2$ in a suitable solvent such as for example tetrahydrofuran in the presence of a base to generate intermediate II-2. Cyclisation of intermediate II-2 can occurs at high temperature in a suitable solvent under acidic conditions to generate intermediate II-3. Intermediate II-3 can then be reduced using reducing agents such as for example $BH_3.Me_2S$ or DIBAL-H in a suitable solvent (for example THF or dichloromethane) to generate intermediate II-4. The $W^1$ moiety is introduced onto intermediate II-4 using Suzuki coupling conditions. The displacement of the bromide can be accomplished by using an aryl/heteroaryl boronic acid in the presence of a palladium catalyst (such as Pd $(PH_3)_4$ and a suitable base and solvent to generate a compound of Formula IA.

Scheme 2

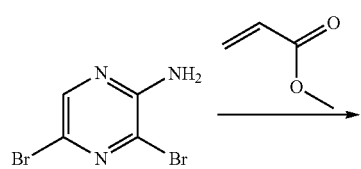

A compound of Formula IB, IC or ID in which $R^c$ is methyl, $L^1$ is a bond, $L^2$ is $CH^2$ and n is 1 can be prepared in a multiple steps synthesis as shown in Schemes 3 to 5. 5-bromo-4-methyl-3-nitropyridin-2-amine can be reacted with methyl bromo acetate in the presence of a suitable base such as sodium hydride in a suitable solvent such as dimethylformamide to generate intermediate III-2. Intermediate III-2 is then reduced and cyclized under acidic conditions to generate intermediate III-3. Intermediate III-3 can then be reduced using reducing agents such as for example $BH_3.Me_2S$ or DIBAL-H in a suitable solvent (for example THF or dichloromethane) to generate intermediate III-4. An alternative route to intermediate III-2 is also described in Scheme 3: 5-bromo-2-hydroxy-4-methyl-3-nitropyridine is reacted with phosphorous oxychloride to generate intermediate III-1 which is subsequently reacted with methyl glycinate to generate intermediate III-2.

Scheme 3

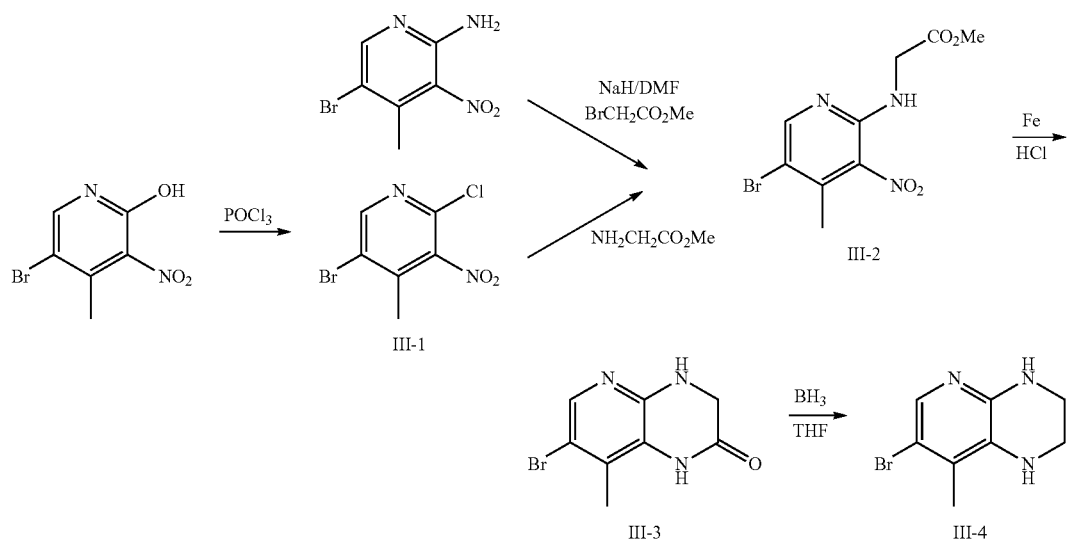

Intermediate III-4 can also be prepared using an alternative route shown in Scheme 4. 5-Bromo-4-methyl-3-nitropyridin-2-amine is reduced using a reducing agent such as Fe/HCl to generate intermediate N-1. Intermediate IV-1 is reacted with glyoxal to generate intermediate N-2. Reduction of intermediate IV-2 with sodium borohydride generates intermediate III-4.

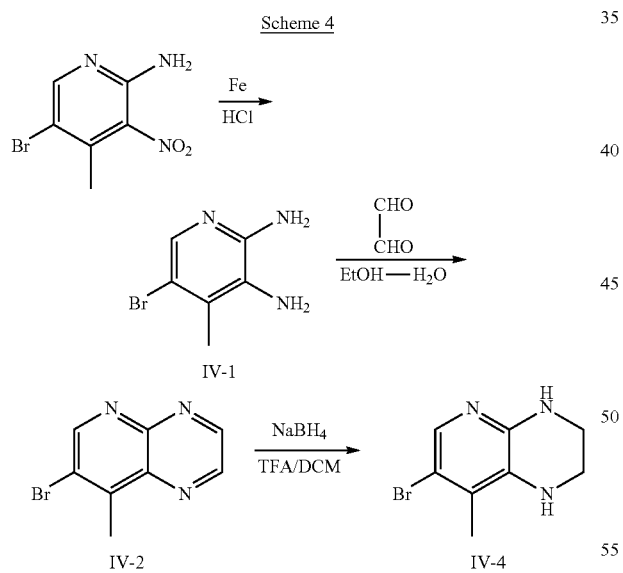

A compound of Formula IB, IC or ID in which $R^c$ is methyl, $L^1$ is a bond, $L^2$ is $CH_2$ and n is 1 can then be prepared from intermediate III-4 in two additional steps as shown is Scheme 5: Intermediate III-4 is alkylated with a LG-$CH_2$—$W^2$ moiety in which LG depicts a leaving group such as I, Br, Cl and the like in a suitable solvent such as acetonitrile. The alkylation can be facilitated by using high temperature and/or microwave chemistry. Separation of the two isomers V-1a and V-1b can be performed using high pressure liquid chromatography or other separation techniques known to those skilled in the art. Intermediate V-1b is then submitted to Suzuki coupling reaction with $W^1B(OH)_2$ in order to introduce the $W^1$ moiety. $W^1$ and $W^2$ are as previously described in part 1.

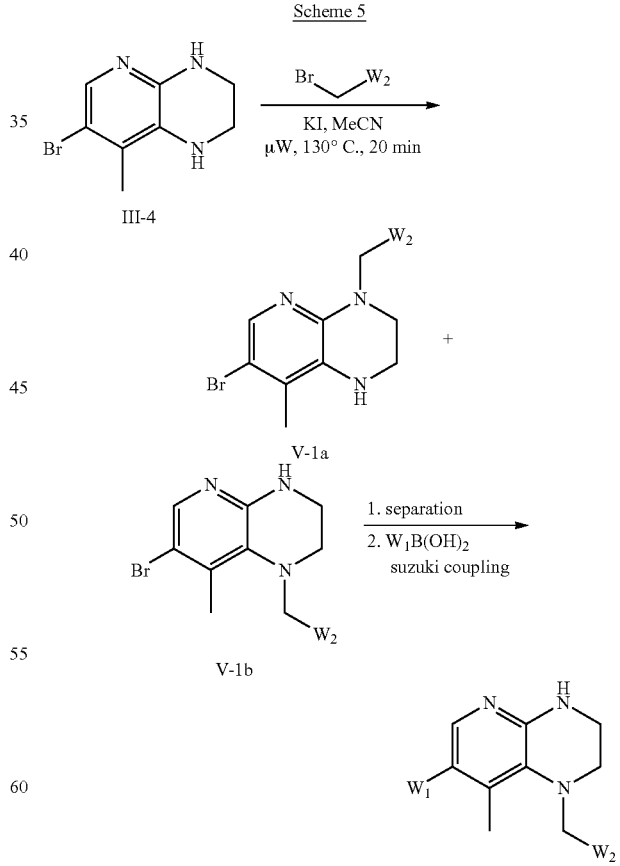

A compound of Formula ID in which $R^c$ is methyl, $L^1$ is a bond, $L^2$ is $CH^2$ and n is 2 is prepared in multiple steps as shown in Scheme 6: 5-Bromo-2-chloro-4-methyl-3-nitropyridine is reacted with methyl fβ-alaninate hydrochloride in order to generate intermediate VI-1. Reduction of the nitro group using Fe/NH₄Cl; followed by cyclization under acidic conditions generate intermediate VI-3. Selective alkylation with a LG-CH₂W² moiety, in which LG is a leaving group such as Br, I, Cl and the like, can be accomplished using a suitable base such as KN(SiMe₃)₂ to generate intermediate VI-4. Intermediate VI-4 can then be reduced using reducing agents such as for example BH₃.Me₂S or DIBAL-H in a suitable solvent (for example THF or dichloromethane) to generate intermediate VI-5. The W¹ moiety is introduced onto intermediate VI-5 using Suzuki coupling conditions as previously described in Scheme 1.

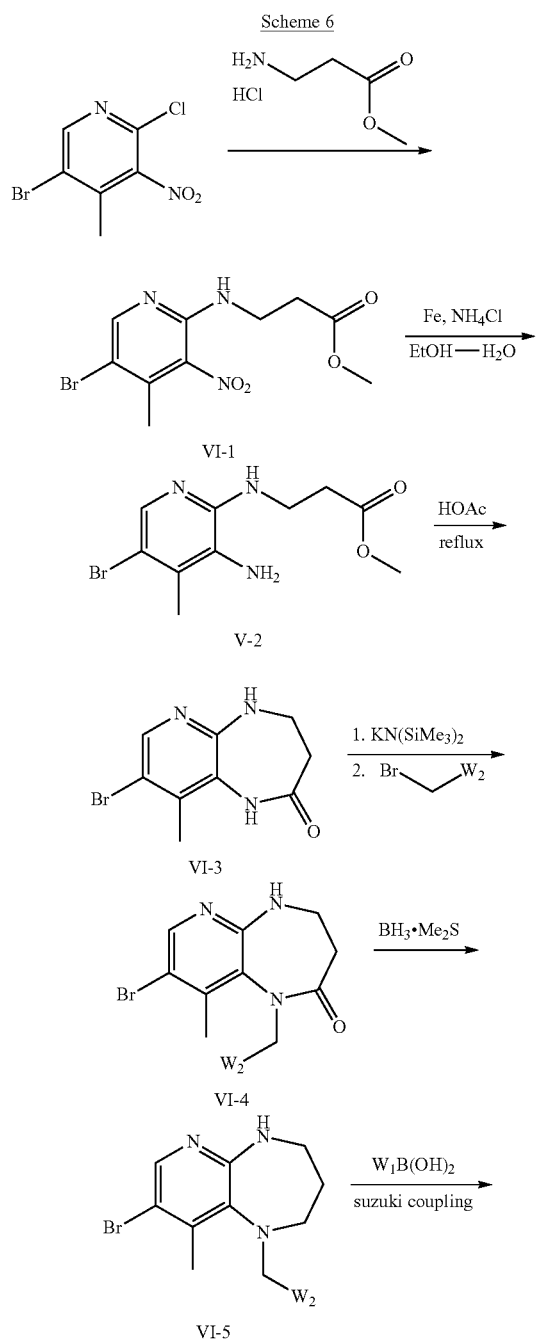

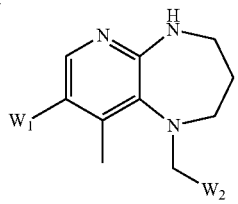

Compounds of Formula IA or IB in which L² is CH₂ and L¹ is NH can be prepared, as shown in Scheme 7, from intermediates I-4, II-4, V-1b or VI-5 and the like, by first protecting the free amine with a protective group such as SEM [2-(trimethylsilyl)ethoxymethyl], and by reacting the heteroaryl bromide (Intermediate VII-1) with a W¹NH₂ moiety using Buchwald-Hartwig amination conditions. The protecting group can then be removed using the appropriate condition such as for example TBAF for removing SEM group.

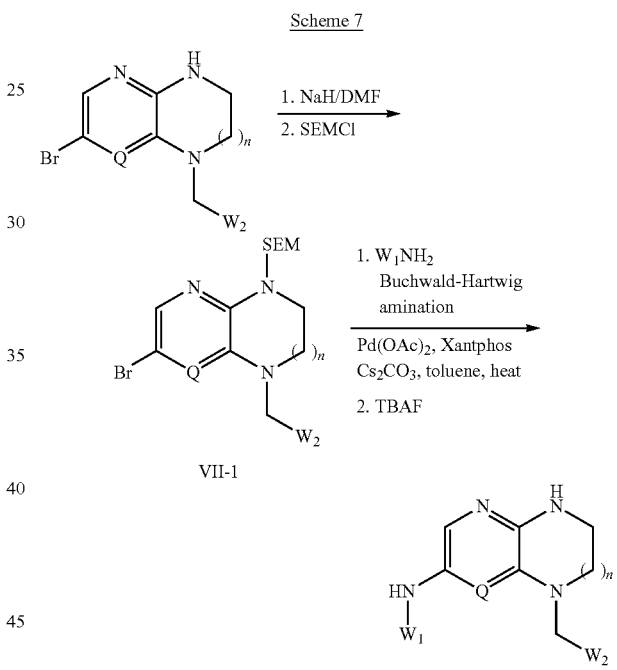

In a similar way, compounds of Formula IA or IB in which L² is CH₂ and L¹ is O can be prepared, as shown in Scheme 8, from intermediates I-4, II-4, V-1b, VI-5 or the like, by reacting an intermediate VIII-1 with W¹—OH under Buchwald-Hartwig etherification conditions.

A prior amine protection is also required as described in Scheme 7 and shown in Scheme 8.

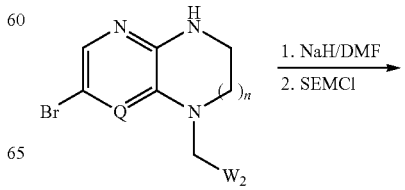

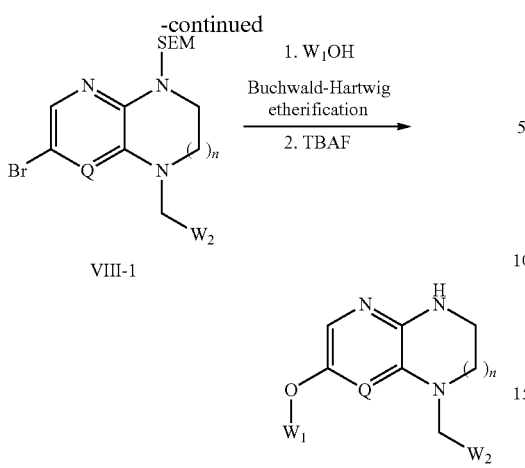

VIII-1

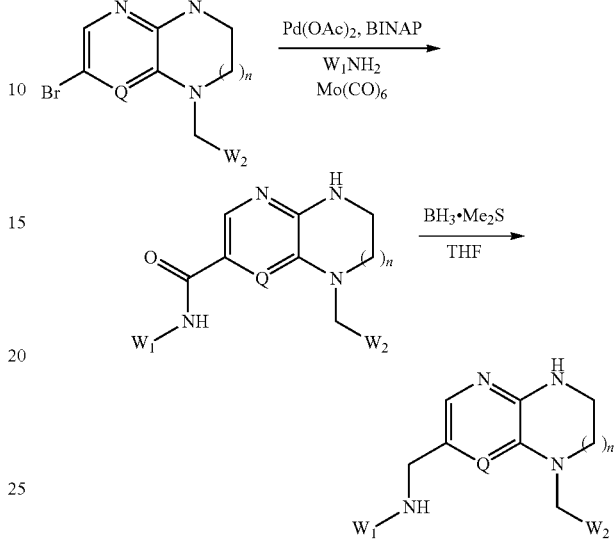

The preparation of a compound of Formula IA, IB or ID in which $L^2$ is $CH_2$, $L^1$ is a bond and $W^1$ is a N-linked 5-, 6- or 7-membered heterocyclyl, can also be achieved using Buchwald-hartwig amination conditions as described in Schemes 7 and 8. In scheme 9, the exemplified heterocyclyl is a piperazine substituted with $R^a$.

Scheme 9

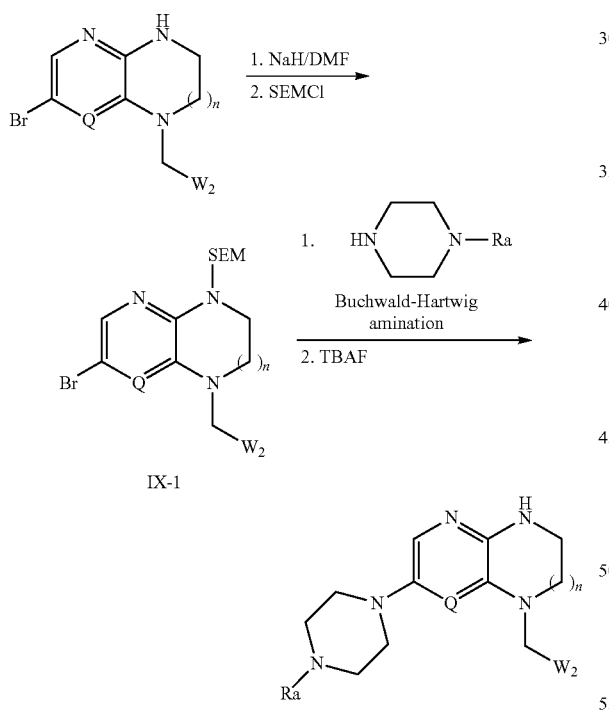

IX-1

The preparation of a compound of Formula IA or IB in which $L^2$ is $CH_2$, $L^1$ is C(O)NH or $CH_2NH$ is described in Scheme 10. An intermediate I-4, II-4, V-1b, VI-5 or the like, can be reacted with $W^1NH_2$ in the presence of $Mo(CO)_6$, BINAP and $Pd(OAc)_2$ to generate a compound of Formula IA or ID in which $L^1$ is C(O)NH. The amide bond formation can also be achieved via other Pd-catalyzed CO insertion and subsequent amination. The carbon monoxide source can also be carbon monoxide gas or other metal carbonyl complexes such as for example $Co_2(CO)_8$, $Ni(CO)_4$, $Ru_3(CO)_{12}$, $Mn_2(CO)_{12}$ and the like. Reduction of the amide functionality with a reducing agent such as for example $BH_3 \cdot Me_2S$ generates a compound of Formula IA or IB in which $L^1$ is $CH_2NH$.

Scheme 10

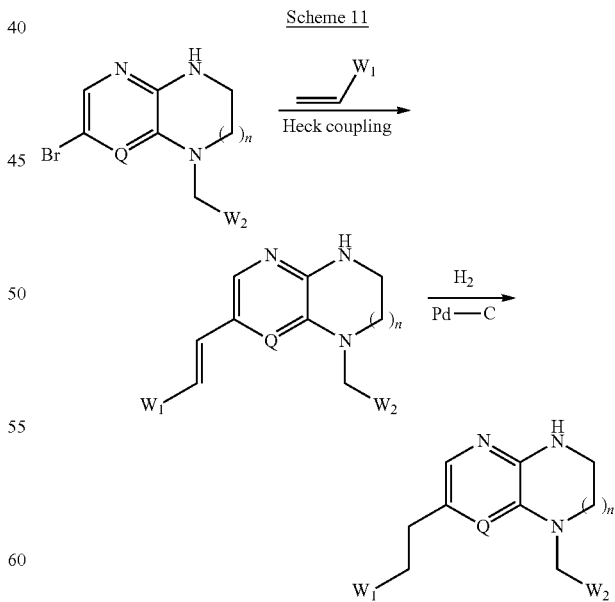

The preparation of a compound of Formula IA or IB in which $L^2$ is $CH_2$, $L^1$ is C=C or $CH_2CH_2$ is described in Scheme 11. An intermediate I-4, II-4, V-1b, VI-5 or the like is reacted with an alkene such as $W^1CHCH_2$ under Heck coupling conditions to generate a compound of Formula IA or IB in which $L^1$ is C=C. hydrogenation of the double bond in the presence of Pd—C as a catalyst generates a compound of Formula IA or IB in which $L^2$ is $CH_2CH_2$.

Scheme 11

Alternatively an intermediate I-4, II-4, V-1b, VI-5 can be reacted with $W^1C$=C—$B(OH)_2$ under Suzuki coupling conditions. A similar reaction is described in tetrahedron 64(7), 1351-1370, 2008.

The preparation of a compound of Formula IA or LB in which $L^2$ is $CH_2$, $L^1$ is $C{\equiv}C$ is described in Scheme 12. An intermediate I-4, II-4, V-1b, VI-5 or the like is reacted with an alkyne under Sonagashira coupling conditions.

Scheme 12

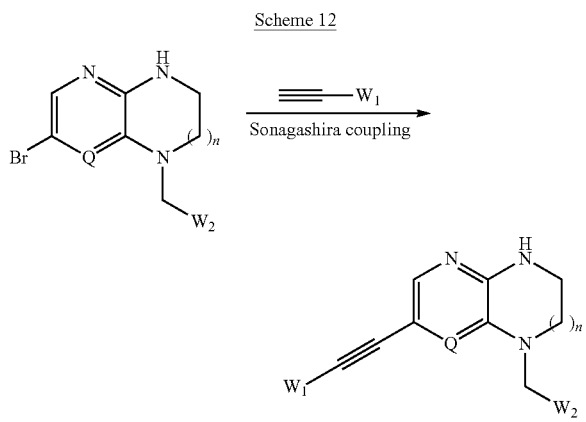

Alternatively, an intermediate I-4, II-4, V-1b, VI-5 or the like can be reacted with trimethylsilanylethyne under Sonagashira conditions to generate intermediate XIII-1. Removal of the trimethylsilane group is followed by a second Sonagashira cross coupling reaction with a $W^1$-halide moiety. This 2 steps sequence reaction is illustrated in Scheme 13. A similar reaction sequence is described in Bioorganic & Medicinal Chemistry (2007), 15(4), 1586-1605.

Scheme 13

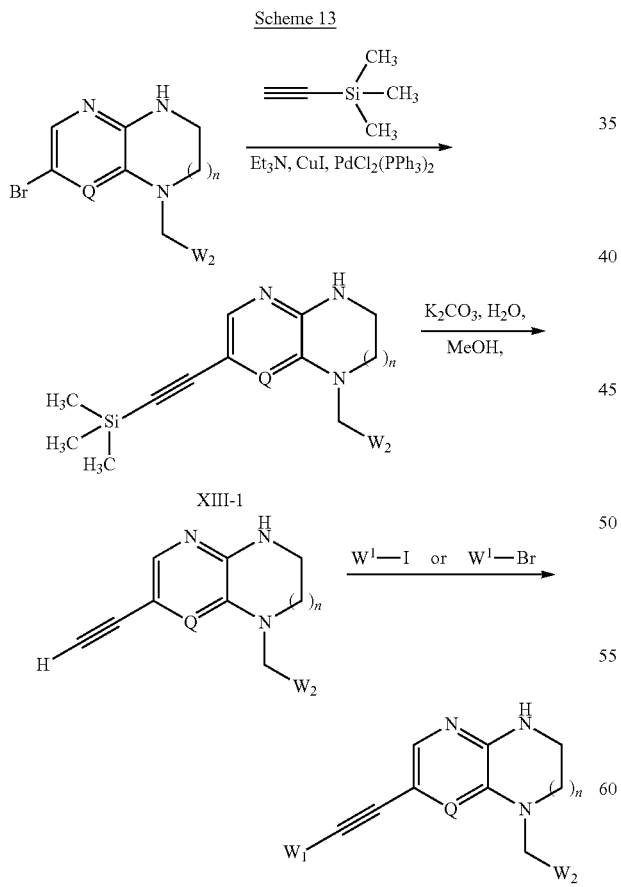

The preparation of compounds of Formula IA, IB or IC in which $L^1$ is a bond and $L^2$ is a bond, C(O), S(O)$_2$, C(O)NH, or an alkyl chain can be achieved via a common intermediate A:

Intermediate A

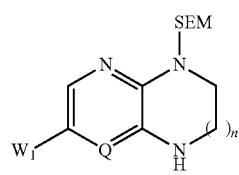

The preparation of intermediates of type A is described below in Scheme 14 and 16.

Scheme 14 described the preparation of an intermediate of type A in which Q is N and n is 1. 3,5-Dibromo-pyrazin-2-amine is converted to intermediate XIV-4 in which $W^2$ is p-methoxyphenyl in a reaction sequence as the one described in Scheme 1. p-Methoxybenzyl functionality (also known as MPM group is used as a protecting group which can be later on selectively deprotected in the presence of a SEM protecting group. Other protecting groups can also be used in place of the MPM groups as long as they can be selectively deprotected in the presence of SEM. An other example is the DMPM protecting group which can be oxidatively cleaved using for example DDQ (2,3-dichloro-5,6-dicyano-1,4-benzoquinone). Someone skilled in the art should be able to identify other suitable protecting groups for this synthetic scheme.

Intermediate XIV-4 is then treated with 2-(Trimethylsilyl) ethoxymethyl Chloride in the presence of a suitable base such as for example NaH to generate intermediate XIV-5. Intermediate XIV-5 is subjected to Suzuki coupling with $W^1B(OH)_2$. Selective deprotection of the MPM group can be achieved for example using $Ce(NH_4)_2(NO_3)_6$ to generate intermediate XIV-7.

Scheme 14

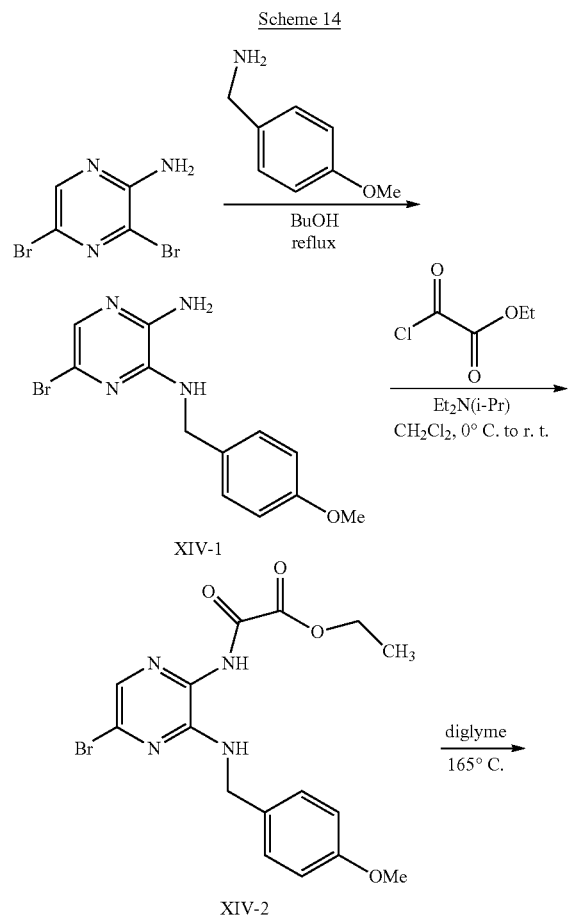

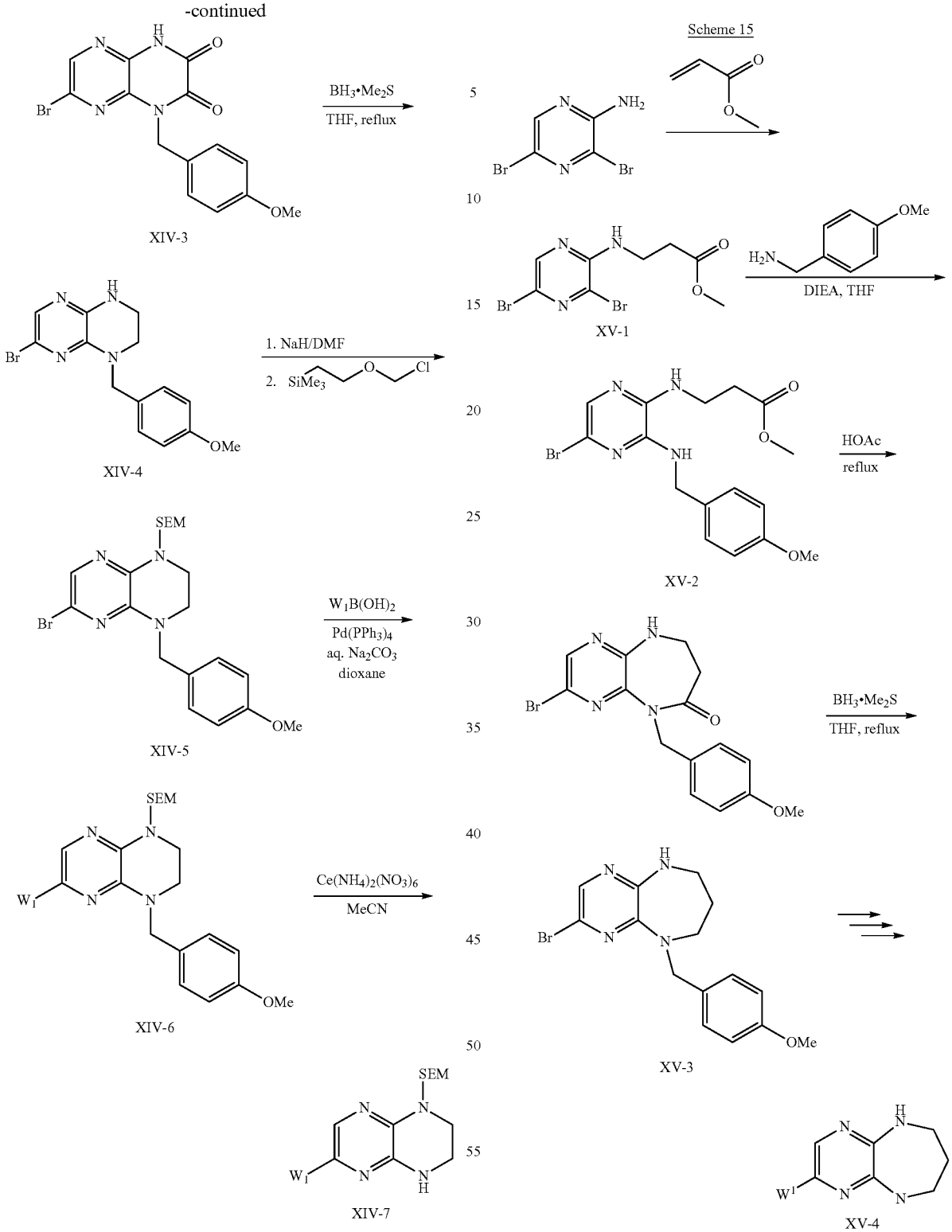

Scheme 15 described the preparation of an intermediate of type A in which Q is N and n is 2. 3,5-Dibromo-pyrazin-2-amine is converted to intermediate XV-3 using the same reaction sequence as the one described in Scheme 2 in which $W^2$ is para-methoxyphenyl. Intermediate XV-3 is then converted to intermediate XV-4 using the protection-deprotection reaction sequence described in Scheme 14.

Scheme 16 described the preparation of an intermediate of type A in which Q is $CR^c$ with $R^c$ being methyl and n is 1 or 2. 5-bromo-2-chloro-4-methyl-3-nitropyridine can be reacted with a SEM-protected methyl glycinate or a SEM-protected methyl β-alaninate to generate intermediate XVI-1 which subsequently undergoes a Suzuki coupling reaction with $W^1B(OH)_2$. Conversion of the nitro group to the amino group can be achieved using standard hydrogenation conditions and intermediate XVI-2 also undergoes cyclization under these conditions. The cyclized intermediate XVI-3 is then reduced using a reducing agent such as for example $LiAlH_4$ to generate intermediate XVI-4.

tion conditions. Removal of the SEM protecting group is done under standard conditions such as for example using TBAF or other fluoride source.

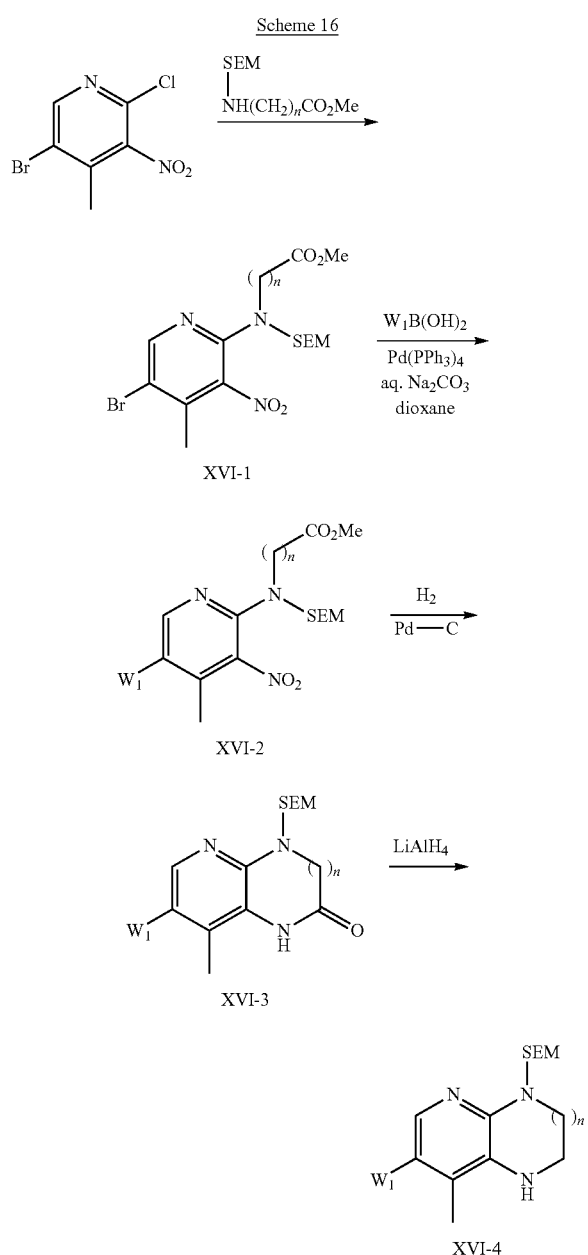

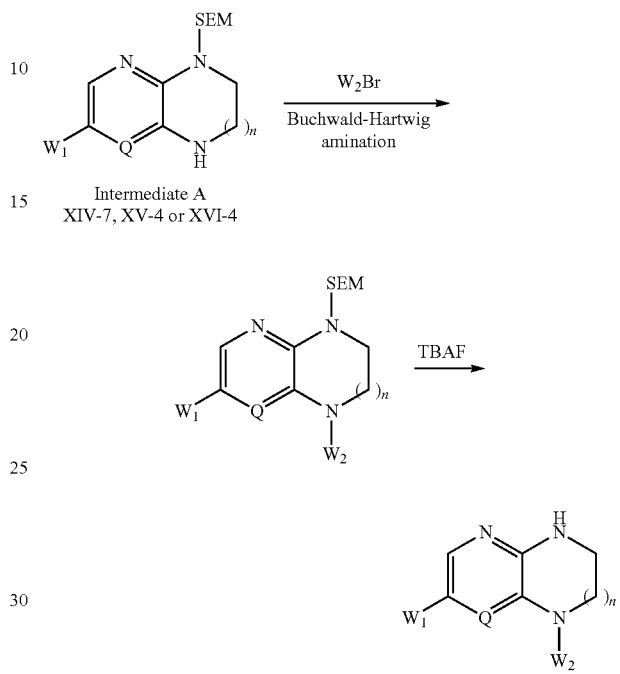

Scheme 18 described the preparation of a compound of Formula IA, IB or IC in which $L^1$ is a bond and $L^2$ is C(O). An intermediate of type A, such as for example intermediates XIV-7, XV-4 or XVI-4, can be reacted with an acyl chloride in the presence of a suitable base such as for example diethylisopropylamine. Acylation is followed by SEM deprotection.

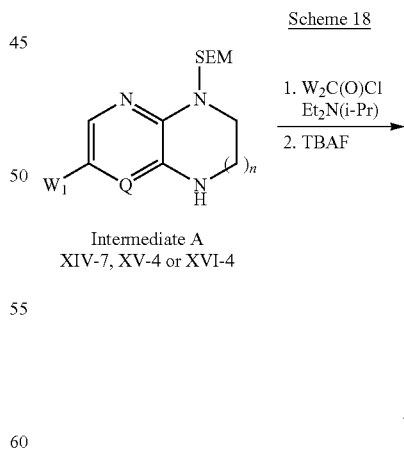

Schemes 17 to 20 illustrate the synthesis of compound of Formula IA, IB or IC in which $L^2$ is a bond, C(O), $S(O)_2$, C(O)NH or a lower alkyl.

The preparation of a compound of Formula IA or IB in which $L^1$ and $L^2$ are bonds is described in Scheme 17. An intermediate of type A, such as those described above (i.e Intermediates XIV-7, XV-4 and XVI-4) can be reacted with $W^2Br$ (or another halide) under Buchwald-Hartwig amina- Under similar conditions, a compound of Formula IA, IB or IC in which $L^1$ is a bond and $L^2$ is $S(O)_2$, can be prepared as described in Scheme 19.

Scheme 19

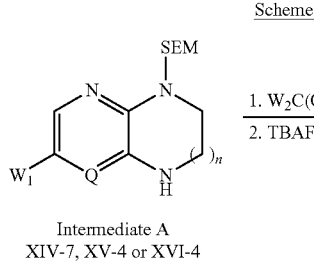

Intermediate A
XIV-7, XV-4 or XVI-4

1. W$_2$C(O)Cl, Et$_2$N(i-Pr)
2. TBAF

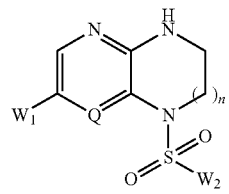

Scheme 20 depicts the synthesis of a compound of Formula IA, IB or IC in which L$^1$ is a bond and L$^2$ is C(O)NH. An intermediate of type A, such as for example intermediates XIV-7, XV-4 or XVI-4, is reacted with an isocyanate followed by SEM deprotection.

Scheme 20

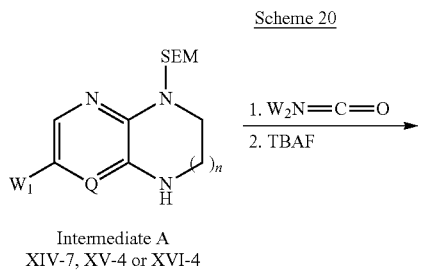

Intermediate A
XIV-7, XV-4 or XVI-4

1. W$_2$N=C=O
2. TBAF

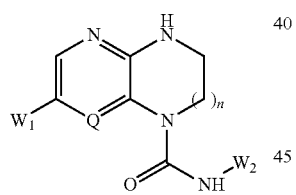

Scheme 21 illustrates an example of synthesis of a compound of Formula IA, IB or IC in which L$^1$ is a bond and L$^2$ is a substituted alkyl. Reacting an intermediate of type A with an epoxide results in the formation of a compound of Formula IA or IB in which L$^2$ is CH$_2$CH(OH).

Scheme 21

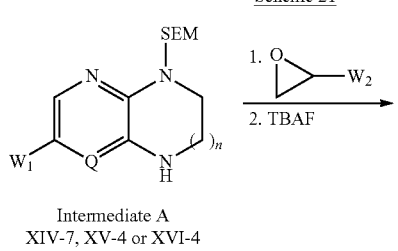

Intermediate A
XIV-7, XV-4 or XVI-4

1. O—W$_2$ (epoxide)
2. TBAF

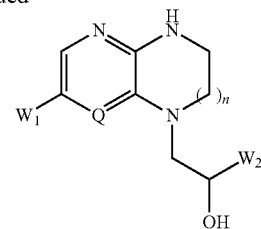

In some embodiments of this invention, one of R$^a$ and R$^b$ is or contains P(=O)(R$^3$)$_2$. Schemes 22 to 30 illustrate the preparation of phosphorous containing substituents and phosphorous containing moieties of current interest.

In a general way a P(O)(R$^3$)$_2$ group can be introduced onto an aryl or heteroaryl moiety by reaction of an aryl halide or heteroaryl halide with P(O)H(R$^3$)$_2$ in the presence of a Palladium catalyst as described in Scheme 21.

Scheme 22

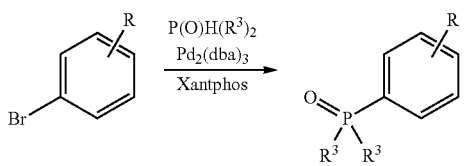

In which R is R$^a$ or R$^b$ or a functional group such as for example, NH$_2$, OH, halo, CH=CH$_2$, CCH and the like.

Scheme 23 illustrates for example the preparation of a W$^1$—NH$_2$ or W$^2$—NH$_2$ moiety in which W$^2$ is a pyridine substituted with P(=O)R$^3$R$^3$.

Scheme 23

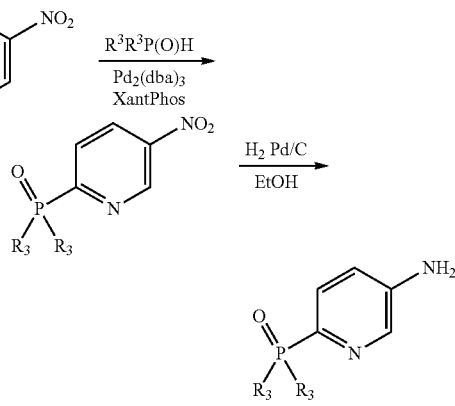

in which R$^3$ is defined in part 1. A similar synthetic route could be used to introduce a P(=O)R$^3$R$^3$ substituent onto a phenyl ring whether the ring is W$^1$ or W$^2$. This scheme can be used for example for the synthesis of compounds of this invention of Formulae IA or IB in which L$^1$ is NH.

Of other interest are compounds in which R$^a$ or R$^b$ substituent is phosphorous containing substituent. Scheme 24 illustrates the synthesis of an intermediate W$^1$—NH$_2$ or W$^2$—NH$_2$ in which W$^1$ or W$^2$ is a phenyl substituted with P(=O)(CH$_3$)$_2$.

Scheme 24

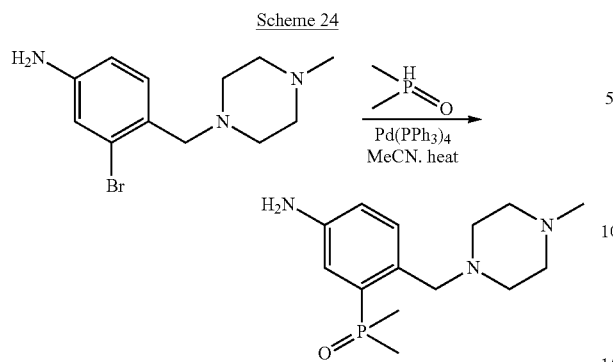

Scheme 25 illustrates the preparation of a $W^1$—$NH_2$ or $W^2$—$NH_2$ intermediate in which $W^1$ or $W^2$ is a phenyl substituted with $(CH_2)P(=O)R^3R^3$. This scheme is particularly useful for the synthesis of compounds of Formulae IA and IB in which $L^1$ is NH.

Scheme 25

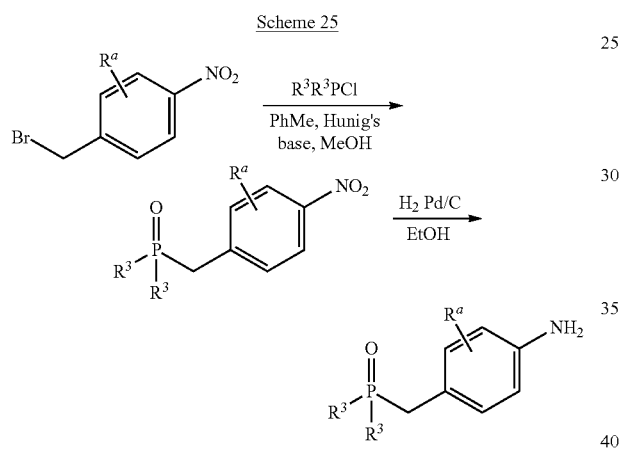

Scheme 25 illustrates the preparation of a $W^1$—$NH_2$ or $W^2$—$NH_2$ moiety in which $W^1$ or $W^2$ is a bicyclic structure such as naphthalene substituted with $P(O)(R^3)_2$.

Scheme 26

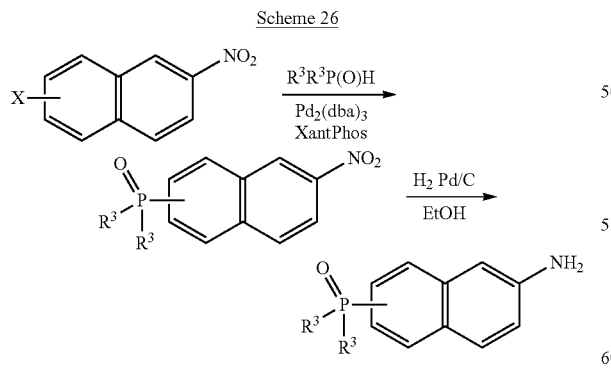

in which X is a halogen such as for example bromo or iodo.

Scheme 27 illustrates the synthesis of $W^1$—$(CH_2)$—$NH_2$ or $W^2$—$(CH_2)$—$NH_2$ intermediate in which $W^1$ or $W^2$ is phenyl substituted with $P(O)(R^3)_2$ and n is 1. This scheme is particularly useful for the synthesis of compounds of Formulae IA or IB in which $L^2$ is $CH_2$.

Scheme 27

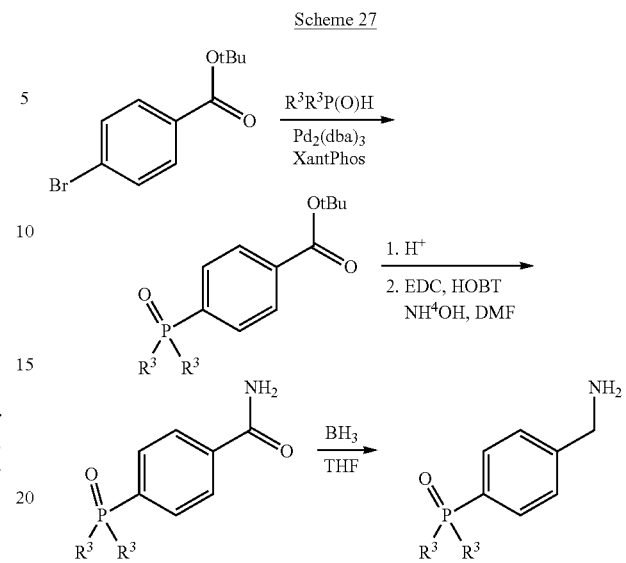

In some embodiment, a $R^a$ or $R^b$ containing $P(O)(R^3)_2$ substituent can be of cyclic structure.

Schemes 28 and 29 illustrate the synthesis of cyclic structures of interest containing $P(O)(R^3)_2$ Scheme 28 illustrates the preparation of cyclic substituent $R^a$ (or $R^b$) containing $P(O)(R^3)_2$

Scheme 28

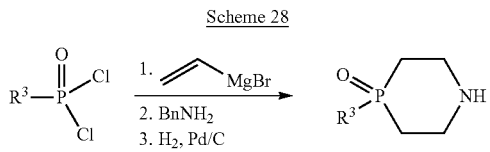

Schemes 28A and 28B illustrate the incorporation of this cyclic substituent onto a $W^1$ or $W^2$.

Scheme 28A and 28B illustrate the synthesis of a $W^1$—$NH_2$ or $W^2$—$NH_2$ moiety in which $W^1$ or $W^2$ is a phenyl substituted with a methoxy group and with a $P(=O)R^3R^3$ containing cyclic substituent.

Scheme 28A

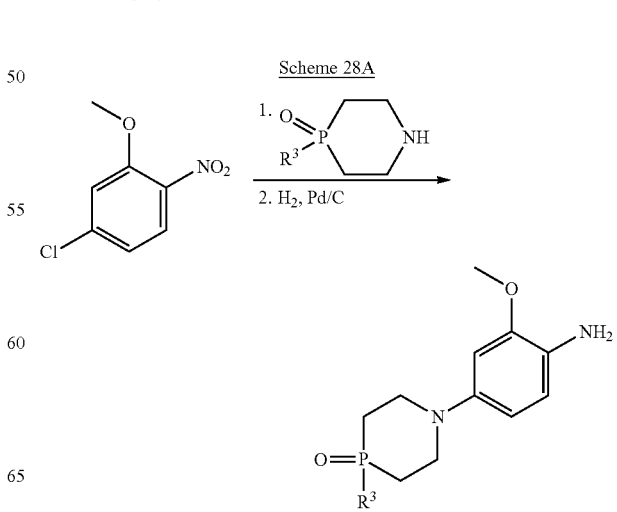

Scheme 28B

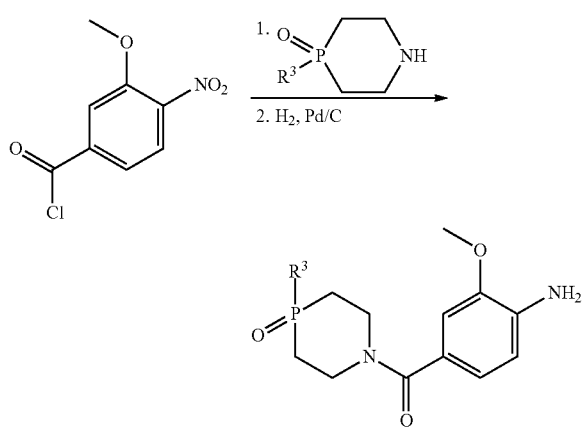

Scheme 29 illustrates the synthesis of a W1-NH$_2$ or W$^2$—NH$_2$ intermediate in which W$^1$ or W$^2$ is phenyl substituted by methoxy and a P(O)(R$_3$)$_2$ group in which the two R$^3$ groups form with the phosphorous atom to which they are attached 6-membered saturated ring.

Scheme 29

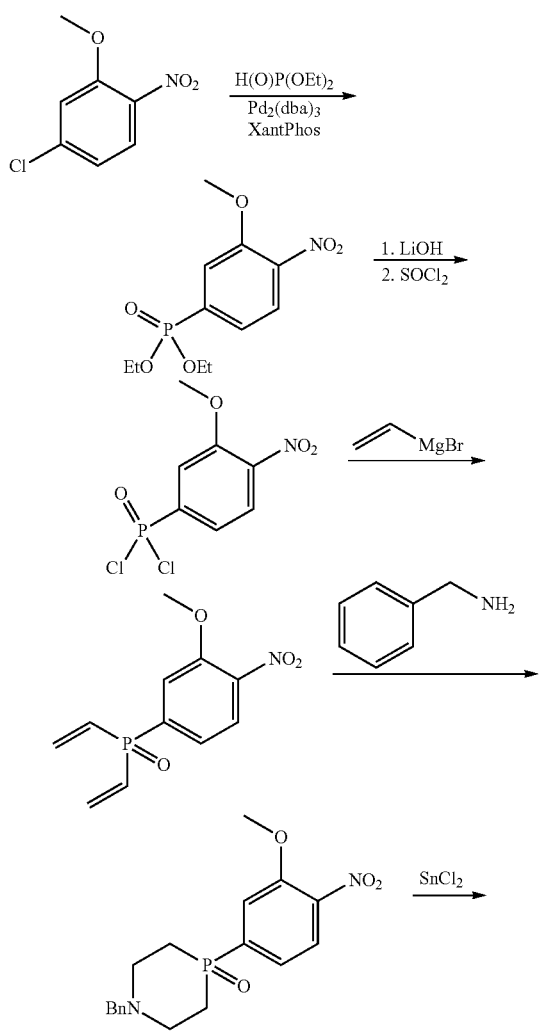

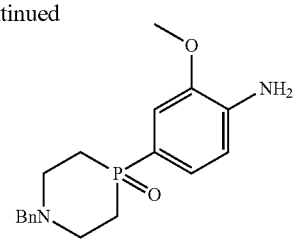

Scheme 30 illustrates the synthesis of a piperazine substituent which is further substituted with —CH$_2$P(=O)(CH$_3$)$_2$. This scheme can be used for the synthesis of W$^1$—NH$_2$ or W$^2$—NH$_2$ intermediate in which W$^1$ or W$^2$ is a phenyl substituted with a phosphorous containing piperazine group. It could also be used for the synthesis of a compound of formula IA or IB in which L$^1$ is a bond and W$^1$ is a piperazine ring substituted with —CH$_2$P(=O)(CH$_3$)$_2$.

Scheme 30

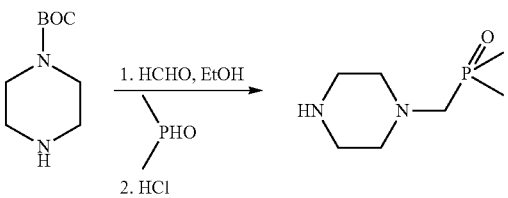

With synthetic approaches such as the foregoing, combined with the examples which follow, additional information provided herein and conventional methods and materials, the practitioner should be able to prepare the full range of compounds disclosed herein.

The synthetic guidance provided in Schemes 1 through 30 is applicable to a variety of W$^1$ and W$^2$ moieties of this invention and allows the preparation of all compounds of this invention.

5. Uses, Formulations, Administration

Pharmaceutical Uses; Indications

This invention provides compounds having biological properties which make them of interest for treating or modulating disease in which kinases may be involved, symptoms of such disease, or the effect of other physiological events mediated by kinases. For instance, a number of compounds of this invention have been shown to inhibit tyrosine kinase activity of alk, fak and c-met, among other tyrosine kinases which are believed to mediate the growth, development and/or metastasis of cancer. A number of compounds of the invention have also been found to possess potent in vitro activity against cancer cell lines, including among others karpas 299 cells. Such compounds are thus of interest for the treatment of cancers, including solid tumors as well as lymphomas and including cancers which are resistant to other therapies.

Such cancers include, among others, cancers of the breast, non small cell lung cancer (NSCLS), neural tumors such as glioblastomas and neuroblastomas; esophaegeal carcinomas, soft tissue cancers such as rhabdomyosarcomas, among others); various forms of lymphoma such as a non-Hodgkin's lymphoma (NHL) known as anaplastic large-cell lymphoma (ALCL), various forms of leukemia; and including cancers which are ALK or c-met mediated.

Anaplastic Lymphoma Kinase (ALK) is a cell membrane-spannning receptor tyrosine kinase, which belong to the insulin receptor subfamily. ALK receptor tyrosine kinase (RTK) was initially identified due to its involvement in the human non-Hodgkin lymphoma subtype known as anaplastic large-cell lymphoma (ALCL). ALK normally has a restricted distribution in mammalian cells, being found at significant levels only in nervous system during embryonic development, suggesting a possible role for ALK in brain development (Duyster, J. Et al., *Oncogene,* 2001, 20, 5623-5637).

In addition to its role in normal development, expression of the full-length normal ALK has also been detected in cell lines derived from a variety of tumors such as neuroblastomas, neuroectodermal tumors (Lamant L. Et al., *Am. J. Pathol.,* 2000, 156, 1711-1721; Osajima-Hakomori Y., et al., *Am. J. Pathol.* 2005, 167, 213-222) and glioblastoma (Powers C. et al., *J. Biol. Chem.* 2002, 277, 14153-14158; Grzelinski M. et al., Int. *J. Cancer,* 2005, 117, 942-951; Mentlein, R. Et al., *J. Neurochem.,* 2002, 83, 747-753) as well as breast cancer and melanoma lines (Dirk W G. Et al., *Int. J. Cancer,* 2002, 100, 49-56).

In common with other RTKs, translocations affect the ALK gene, resulting in expression of oncogenic fusion kinases—the most common of which is NPM-ALK. For example, approximately sixty percent of anaplastic large cell lymphomas (ALCL) are associated with a chromosome mutation that generates a fusion protein consisting of nucleophosmin (NMP) and the intracellular domain of ALK. (Armitage, J. O. et al., Cancer: principle and practice of oncology, $6^{th}$ Edition, 2001, 2256-2316; kutok, J. L. & Aster J. C., *J. Clin. Oncol.,* 2002, 20, 3691-3702; Wan, W. et al., *Blood,* 2006, 107, 1617-1623. This mutant protein, NMP-ALK, possesses a constitutively active tyrosine kinase domain that is responsible for its oncogenic property through activation of downstream effectors (Falini, B and al., *Blood,* 1999, 94, 3509-3515; Morris, S. W. et al., *Brit. J. Haematol.,* 2001, 113, 275-295). Experimental data have demonstrated that the aberrant expression of constitutively active ALK is directly implicated in the pathogenesis of ALCL and that inhibition of ALK can markedly impair the growth of ALK positive lymphoma cells (Kuefer, Mu et al., *Blood,* 1997, 90, 2901-2910; Bai, R. Y. et al., *Exp. Hematol.,* 2001, 29, 1082-1090; Slupianek, A. et al., *Cancer Res.,* 2001, 61, 2194-2199; Turturro, F. et al., *Clin. Cancer. Res.,* 2002, 8, 240-245). The constitutively activated chimeric ALK has also been demonstrated in about 60% of inflammatory myofibroblastic tumors (IMTs), a slow growing sarcoma that mainly affects children and young adults (Lawrence, B. et al., Am. J. Pathol., 2000, 157, 377-384). Furthermore, recent reports have also described the occurrence of a variant ALK fusion, TPM4-ALK, in cases of squamous cell carcinoma (SCC) of the esophagus (Jazzi fr., et al., *World J. Gastroenterol.,* 2006, 12, 7104-7112; Du X., et al., *J. Mol. Med.,* 2007, 85, 863-875; Aklilu M., *Semin. Radiat. Oncol.,* 2007, 17, 62-69). Thus, ALK is one of the few examples of an RTK implicated in oncogenesis in both non-hematopoietic and hematopoietic malignancies. More recently it has been shown that a small inversion within chromosome 2p results in the formation of a fusion gene comprising portions of the echinoderm microtubule-associated protein-like 4 (EML4) gene and the anaplastic lymphoma kinase (ALK) gene in non-small-cell lung cancer (NSCLC) cells (Soda M., et al., Nature, 2007, 448, 561-567).

We therefore envision that an ALK inhibitor would either permit durable cures when used as a single therapeutic agent or combined with current chemotherapy for ALCL, IMT, proliferative disorders, glioblastoma and other possible solid tumors cited herein, or, as a single therapeutic agent, could be used in a maintenance role to prevent recurrence in patients in need of such a treatment.

Pharmaceutical Methods

The method of the invention comprises administering to a subject in need thereof a therapeutically effective amount of a compound of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The compound, or a composition containing the compound, may be administered using any amount and any route of administration effective for killing or inhibiting the growth of tumors or other forms of cancer.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Regarding the Compounds

Compounds of present invention can exist in free form for treatment, or where appropriate, as a pharmaceutically acceptable salt or other derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, both of which are incorporated herein by reference.

Compositions

Accordingly, compositions are provided, which comprise any one of the compounds described herein (or a prodrug, pharmaceutically acceptable salt or other pharmaceutically acceptable derivative thereof), and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methyl cellulose.

In the case of skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers.

Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self emulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening and/or flavoring and/or coloring agents may be added.

The pharmaceutical compositions of this invention may comprise formulations utilizing liposome or microencapsulation techniques, various examples of which are known in the art.

The pharmaceutical compositions of this invention may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Combinations

While the compounds of the invention can be administered as the sole active pharmaceutical agent, they can also be used in combination with one or more other compounds of the invention or with one or more other agents. When administered as a combination, the therapeutic agents can be formulated as separate compositions that are administered at the same time or sequentially at different times, or the therapeutic agents can be given as a single composition.

The phrase "combination therapy", in referring to the use of a compound of this invention together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

Thus, the administration of compounds of the present invention may be in conjunction with additional therapies known to those skilled in the art in the prevention or treatment of cancer, such as radiation therapy or cytostatic agents, cytotoxic agents, other anti-cancer agents and other drugs to ameliorate symptoms of the cancer or side effects of any of the drugs.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simultaneously with, or after administration of the other anticancer or cytotoxic agent.

Currently, standard treatment of primary tumors consists of surgical excision, when appropriate, followed by either radiation or chemotherapy, and typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention includes antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co.

EX-015, fazarabine, floxuridine, fludarabine phosphate, 5-fluorouracil, N-(21-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of (xcarotene, (X-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5. antineoplaston AS2-1F Henkel APD, aphidicolin glycinate, asparaginase, Avarol, baccharin, batracylin, benfluoron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Wamer-Lambert CI-921, WarnerLambert CI-937, Warner-Lambert CI-941, Warner-Lambert CI958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MGI136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM Alternatively, the present compounds may also be used in co-therapies with other antineoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-1a, interferon beta-1b, interferon gamma, natural interferon gamma-1a, interferon gamma-1b, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama. vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of this invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

EXAMPLES

Example 1

1-(2-chloro-3,6-difluorobenzyl)-7-[3-(morpholin-4-yl)phenyl]-1,2,3,4-tetrahydropyrazino[2,3-b]pyrazine

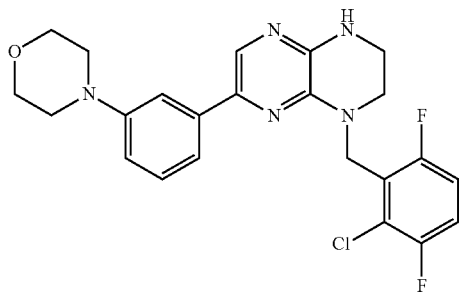 [SMILES: Fc1ccc(F)c(CN2CCNc3ncc(-c4cccc(N5CCOCC5)c4)nc32)c1Cl]

5-bromo-N$^3$-(2-chloro-3,6-difluorobenzyl)pyrazine-2,3-diamine: A solution of 2-amino-3,5-dibromopyrazine (29 mmol, 7.35 g), 2-chloro-3,6-difluorobenzylamine (29 mmol, 5.16 g), and N, N-diethylisopropylamine (32 mmol, 5.6 mL) in n-BuOH (20 mL) was refluxed for 72 hrs. After volatile components were removed on rotavap, EtOAc and water were added to the residue to facilitate the extraction. The combined organic layers were combined, dried, concentrated, and then subjected to a silica gel column chromatography by using hexanes/EtOAc (4:1) as eluents, furnishing 5-bromo-N$^3$-(2-chloro-3,6-difluorobenzyl)pyrazine-2,3-diamine in 70% yield (7.14 g).

Ethyl ({5-bromo-3-[(2-chloro-3,6-difluorobenzyl)amino]pyrazin-2-yl}amino)(oxo)acetate: To a stirred solution of 5-bromo-N$^3$-(2-chloro-3,6-difluorobenzyl)pyrazine-2,3-diamine (5.15 mmol, 1.8 g) and N,N-diethylisopropylamine (9.30 mmol, 2 mL) in CH$_2$Cl$_2$ (20 mL) was added ethyl glyoxylate (5.41 mmol, 0.74 g) at 0° C. The suspension was warmed up naturally and stirred overnight. Water was added to dissolve the precipitation. The combined organic layers from extraction were combined, dried, concentrated, and then subjected to a silica gel column chromatography by using CH$_2$Cl$_2$/MeOH (9:1) as eluents, furnishing ethyl ({5-bromo-3-[(2-chloro-3,6-difluorobenzyl)amino]pyrazin-2-yl}amino)(oxo)acetate in 52% yield (1.20 g).

7-bromo-1-(2-chloro-3,6-difluorobenzyl)-1,4-dihydropyrazino[2,3-b]pyrazine-2,3-dione: A solution of ethyl ({5-bromo-3-[(2-chloro-3,6-difluorobenzyl)amino]pyrazin-2-yl}amino)(oxo)acetate (1.20 g) in diglyme was heated at 165° C. for 16 hrs. The volatile components were removed on rotavap and then under vacuum. The residue was subjected to a silica gel column chromatography by using CH$_2$Cl$_2$/MeOH (9:1) as eluents, furnishing 7-bromo-1-(2-chloro-3,6-difluorobenzyl)-1,4-dihydropyrazino[2,3-b]pyrazine-2,3-dione in 43% yield (0.46 g).

7-bromo-1-(2-chloro-3,6-difluorobenzyl)-1,2,3,4-tetrahydropyrazino[2,3-b]pyrazine: To a solution of 7-bromo-1-(2-chloro-3,6-difluorobenzyl)-1,4-dihydropyrazino[2,3-b]pyrazine-2,3-dione (2.5 mmol, 1.0 g) in THF (5 mL) was added BH3.Me2S (7.5 mmol, 3.75 mL, 2.0 M in THF). The resulting solution was refluxed for 2 hrs under N2. Excessive BH3 was quenched by addition of MeOH at rt then heating the reaction mixture for 10 min. After volatile components were removed on rotavap, the residue was subjected to a silica gel column chromatography by using 4:1 ratio of CH$_2$Cl$_2$/MeOH (pre-saturated with ammonia gas) as eluents, furnishing 7-bromo-1-(2-chloro-3,6-difluorobenzyl)-1,2,3,4-tetrahydropyrazino[2,3-b]pyrazine in 20% yield (0.19 g).

1-(2-chloro-3,6-difluorobenzyl)-7-[3-(morpholin-4-yl)phenyl]-1,2,3,4-tetrahydropyrazino[2,3-b]pyrazine: A mixture of 7-bromo-1-(2-chloro-3,6-difluorobenzyl)-1,2,3,4-tetrahydropyrazino[2,3-b]pyrazine (0.14 mmol, 51 mg), 3-morpholinophenylboronic acid pinacol ester (0.16 mmol, 46 mg), and Pd(PPh$_3$)$_4$ (0.015 mmol, 17 mg) was placed in a Schlenk tube. This tube was degassed via 3 cycles of vacuum—refill with N2. THF (3 mL, from sureseal bottle) and aqueous K2CO$_3$ (2.0 M, 1 mL, degassed by bubbling with N2 for 10 min) was then added to the solid mixture in the Schlenk tube. The reaction was stopped after heating at 90° C. for 16 hrs. Extraction and concentration of combined organic layers gave a residue, which was purified on a silica gel column by using 6:1 ratio of CH$_2$Cl$_2$/MeOH (pre-saturated with ammonia gas) as eluents, furnishing 1-(2-chloro-3,6-difluorobenzyl)-7-[3-(morpholin-4-yl)phenyl]-1,2,3,4-tetrahydropyrazino[2,3-b]pyrazine in 61% yield (38 mg).

Example 2

3-[8-(2-chloro-3,6-difluorobenzyl)-5,6,7,8-tetrahydropyrazino[2,3-b]pyrazin-2-yl]-N-[3-(dimethylamino)propyl]benzamide

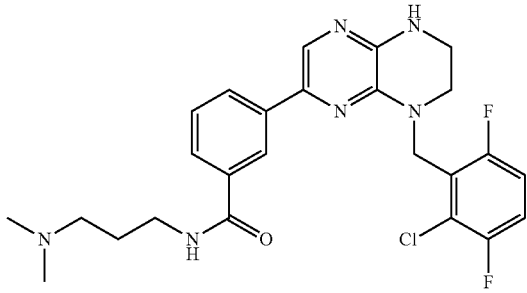 [SMILES: CN(C)CCCNC(=O)c1cccc(-c2cnc3c(n2)N(Cc2c(F)ccc(F)c2Cl)CCN3)c1]

The entitled compound was prepared from 7-bromo-1-(2-chloro-3,6-difluorobenzyl)-1,2,3,4-tetrahydropyrazino[2,3-b]pyrazine and N-[3-(N',N-Dimethylamino)propyl]benzamide-3-boronic acid, pinacol ester using Suzuki coupling conditions as described in Example 1.

Example 3

1-(2-chloro-3,6-difluorobenzyl)-7-{3-[(4-methylpiperazin-1-0)methyl]phenyl}-1,2,3,4-tetrahydropyrazino[2,3-b]pyrazine

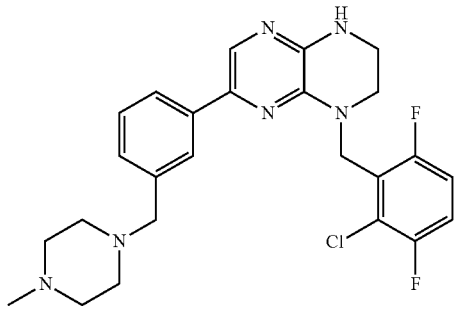 [SMILES: CN1CCN(Cc2cccc(-c3cnc4c(n3)N(Cc3c(F)ccc(F)c3Cl)CCN4)c2)CC1]

The entitled compound was prepared from 7-bromo-1-(2-chloro-3,6-difluorobenzyl)-1,2,3,4-tetrahydropyrazino[2,3-b]pyrazine and 344-Methyl-1-piperazinemethyl)benzeneboronic acid pinacol ester using Suzuki coupling as described in Example 1.

Example 4

1-(2-chloro-3,6-difluorobenzyl)-7-[2-(piperazin-1-yl)pyrimidin-5-yl]-1,2,3,4-tetrahydropyrazino[2,3-b]pyrazine

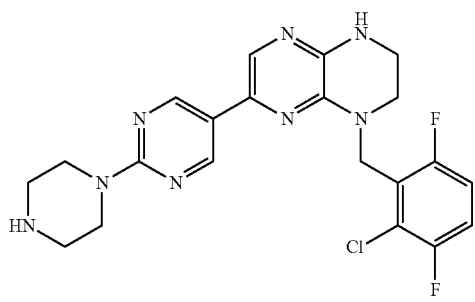 [SMILES: Fc1ccc(F)c(CN2CCNc3ncc(-c4cnc(N5CCNCC5)nc4)nc32)c1Cl]

The entitled compound was prepared from 7-bromo-1-(2-chloro-3,6-difluorobenzyl)-1,2,3,4-tetrahydropyrazino[2,3-b]pyrazine and 2-(4-Boc-piperazin-1-yl)pyrimidine-5-boronic acid pinacol ester using Suzuki coupling conditions as described in Example 1. The Suzuki coupling yielded the desired compound in its BOC protected form. The BOC protected intermediate was then treated with TFA in $CH_2Cl_2$ and purified by Silica gel column chromatography.

Example 5

{4-[8-(2-chloro-3,6-difluorobenzyl)-5,6,7,8-tetrahydropyrazino[2,3-b]pyrazin-2-yl]phenyl}(4-methylpiperazin-1-yl)methanone

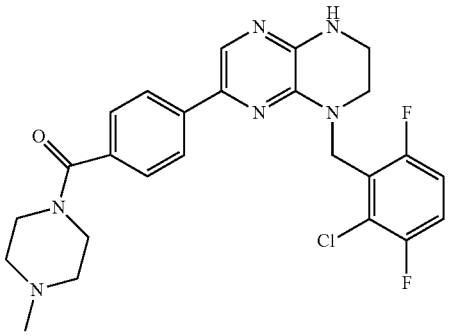 [SMILES: CN1CCN(C(=O)c2ccc(-c3cnc4c(n3)N(Cc3c(F)ccc(F)c3Cl)CCN4)cc2)CC1]

The entitled compound was prepared from 7-bromo-1-(2-chloro-3,6-difluorobenzyl)-1,2,3,4-tetrahydropyrazino[2,3-b]pyrazine and 4-(4-Methylpiperazine-1-carbonyl)phenylboronic acid pinacol ester using Suzuki coupling conditions as described in Example 1.

Example 6

1-(2-chloro-3,6-difluorobenzyl)-7-[3-(morpholin-4-ylmethyl)phenyl]-1,2,3,4-tetrahydropyrazino[2,3-b]pyrazine

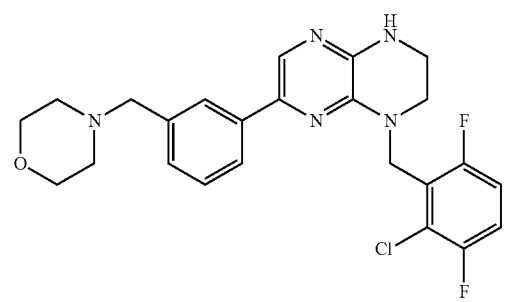 [SMILES: Fc1ccc(F)c(CN2CCNc3ncc(-c4cccc(CN5CCOCC5)c4)nc32)c1Cl]

The entitled compound was prepared from 7-bromo-1-(2-chloro-3,6-difluorobenzyl)-1,2,3,4-tetrahydropyrazino[2,3-b]pyrazine and 3-(Methylmorpholino)phenylboronic acid pinacol ester using Suzuki coupling conditions as described in Example 1.

Example 7

1-(2-chloro-3,6-difluorobenzyl)-7-[4-(morpholin-4-ylmethyl)phenyl]-1,2,3,4-tetrahydropyrazino-[2,3-b]pyrazine

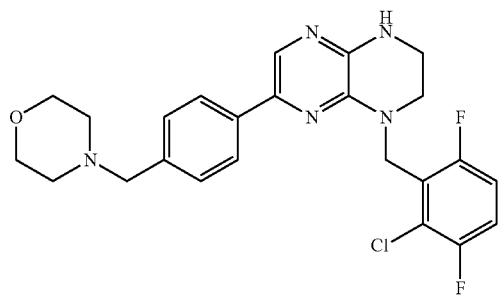 [SMILES: Fc1ccc(F)c(CN2CCNc3ncc(-c4ccc(CN5CCOCC5)cc4)nc32)c1Cl]

The entitled compound was prepared from 7-bromo-1-(2-chloro-3,6-difluorobenzyl)-1,2,3,4-tetrahydropyrazino[2,3-b]pyrazine and 4-(Methylmorpholino)phenylboronic acid pinacol ester using Suzuki coupling conditions as described in Example 1.

Example 8

1-(2-chloro-3,6-difluorobenzyl)-7-[3-(morpholin-4-yl)phenyl]-1,2,3,4-tetrahydropyrazino[2,3-b]pyrazine

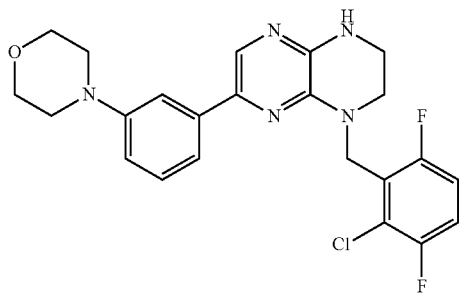 [SMILES: Fc1ccc(F)c(CN2CCNc3ncc(-c4cccc(N5CCOCC5)c4)nc32)c1Cl]

The entitled compound was prepared from 7-bromo-1-(2-chloro-3,6-difluorobenzyl)-1,2,3,4-tetrahydropyrazino[2,3-b]pyrazine and 3-(Morpholino)phenylboronic acid pinacol ester using Suzuki coupling conditions as described in Example 1.

Example 9

1-(2-chloro-3,6-difluorobenzyl)-7-{1-[2-(morpholin-4-yl)ethyl]-1H-pyrazol-4-yl}-1,2,3,4-tetrahydropyrazino[2,3-b]pyrazine

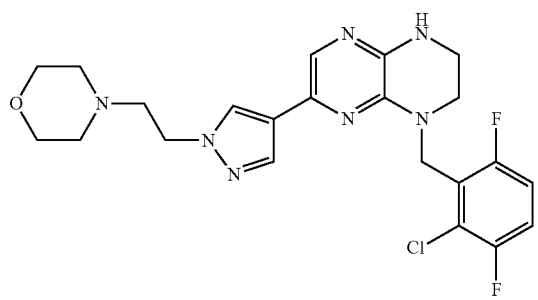 [SMILES: Fc1ccc(F)c(CN2CCNc3ncc(-c4cnn(CCN5CCOCC5)c4)nc32)c1Cl]

The entitled compound was prepared from 7-bromo-1-(2-chloro-3,6-difluorobenzyl)-1,2,3,4-tetrahydropyrazino[2,3-b]pyrazine and 1-(2-Morpholinoethyl)-1H-pyrazole-4-boronic acid, pinacol ester using Suzuki coupling conditions as described in Example 1.

Example 10

3-{4-[8-(2-chloro-3,6-difluorobenzyl)-5,6,7,8-tetrahydropyrazino[2,3-b]pyrazin-2-yl]phenyl}propanehydrazide

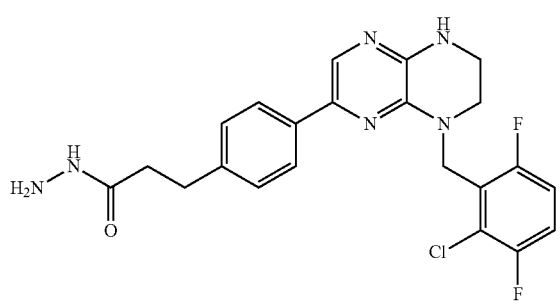 [SMILES: NNC(=O)CCc1ccc(-c2cnc3c(n2)N(Cc2c(F)ccc(F)c2Cl)CCN3)cc1]

The entitled compound was prepared from 7-bromo-1-(2-chloro-3,6-difluorobenzyl)-1,2,3,4-tetrahydropyrazino[2,3-b]pyrazine and 4-(3-Hydrazino-3-oxopropyl)benzeneboronic acid using Suzuki coupling conditions as described in Example 1.

Example 11

1-(2,5-dichlorobenzyl)-7-[6-(4-methylpiperazin-1-yl)pyridin-3-yl]-1,2,3,4-tetrahydropyrazino-[2,3-b]pyrazine

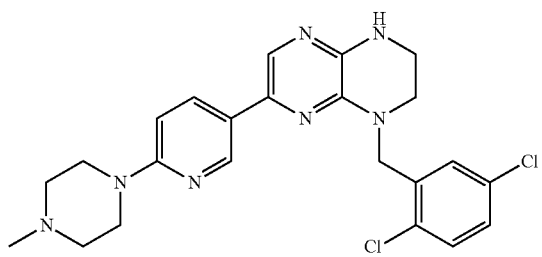 [SMILES: CN1CCN(c2ccc(-c3cnc4c(n3)N(Cc3cc(Cl)ccc3Cl)CCN4)cn2)CC1]

The entitled compound was prepared from 7-bromo-1-(2,5-dichlorobenzyl)-1,2,3,4-tetrahydropyrazino[2,3-b]pyrazine and 2-(4-Methylpiperazin-1-yl)pyridine-5-boronic acid pinacol ester using Suzuki coupling conditions as described in Example 1.

7-bromo-1-(2,5-dichlorobenzyl)-1,2,3,4-tetrahydropyrazino[2,3-b]pyrazine was prepared from 2-amino-3,5-dibromopyrazine as described in Example 1 by replacing 2-chloro-3,6-difluorobenzylamine in step 1 with 2,5-dichlorobenzylamine.

Example 12

{3-[8-(2-chloro-3,6-difluorobenzyl)-5,6,7,8-tetrahydropyrazino[2,3-b]pyrazin-2-yl]phenyl}(4-methylpiperazin-1-yl)methanone

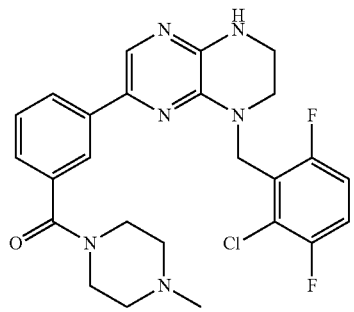 [SMILES: CN1CCN(C(=O)c2cccc(-c3cnc4c(n3)N(Cc3c(F)ccc(F)c3Cl)CCN4)c2)CC1]

The entitled compound was prepared from 7-bromo-1-(2-chloro-3,6-difluorobenzyl)-1,2,3,4-tetrahydropyrazino[2,3-b]pyrazine and 3-(4-Methylpiperazine-1-carbonyl)phenylboronicacid, pinacol ester using Suzuki coupling conditions as described in Example 1.

Example 13

4-[8-(2-chloro-3,6-difluorobenzyl)-5,6,7,8-tetrahydropyrazino[2,3-b]pyrazin-2-yl]-N-[2-(morpholin-4-yl)ethyl]benzamide

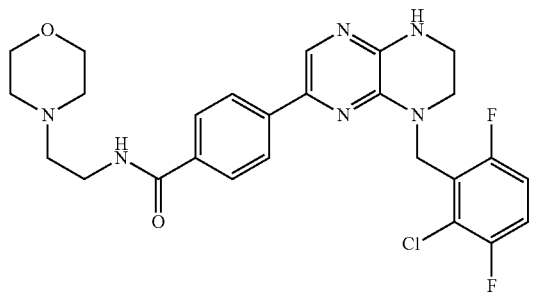 [SMILES: O=C(NCCN1CCOCC1)c1ccc(-c2cnc3c(n2)N(Cc2c(F)ccc(F)c2Cl)CCN3)cc1]

The entitled compound was prepared from 7-bromo-1-(2-chloro-3,6-difluorobenzyl)-1,2,3,4-tetrahydropyrazino[2,3-b]pyrazine and 4-{2-[4-(4,4,5,5-Tetramethyl-[1,3,2]dioxaborolan-2-yl)-phenoxy]-ethyl}-morpholine using Suzuki coupling conditions as described in Example 1.

Example 14

{4-[8-(2-chloro-3,6-difluorobenzyl)-5,6,7,8-tetrahydropyrazino[2,3-b]pyrazin-2-yl]phenyl}[4-(pyrrolidin-1-yl)piperidin-1-yl]methanone

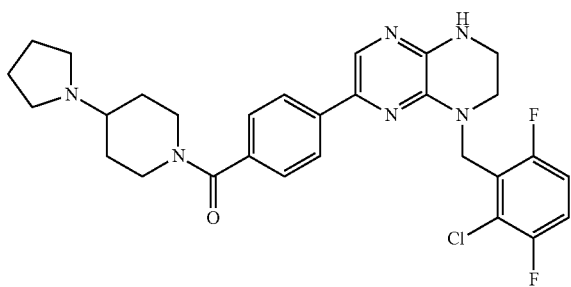 [SMILES: O=C(c1ccc(-c2cnc3c(n2)N(Cc2c(F)ccc(F)c2Cl)CCN3)cc1)N1CCC(N2CCCC2)CC1]

The entitled compound was prepared from 7-bromo-1-(2-chloro-3,6-difluorobenzyl)-1,2,3,4-tetrahydropyrazino[2,3-b]pyrazine and [4-(pyrrolidin-1-yl)piperidin-1-yl][4-(4,4,5,5-tetramethyl-1,3,2-dioxaborolan-2-yl)phenyl]methanone using Suzuki coupling conditions as described in Example 1.

[4-(pyrrolidin-1-yl)piperidin-1-yl][4-(4,4,5,5-tetramethyl-1,3,2-dioxaborolan-2-yl)phenyl]methanone: A solution of 4-(4,4,5,5-tetramethyl[1,3,2]dioxaborolan-2-yl)benzoic acid (9.80 mmol, 2.43 g), 4-(1-pyrrolidinyl)piperidine (10.77 mol, 1.66 g), 1-hydroxybenzotriazole (16.67 mmol, 2.25 g), and N-(3-dimethylaminopropyl)-N'-ethylcarbodiimide hydrochloride (19.57 mmol, 3.75 g) in DMF (30 mL) was stirred overnight at 60° C. Upon removal of DMF on rotavap, the residue was taken into mixture of EtOAc and H2O. The combined organic layers from extraction were stirred with aq. 2N HCl for 20 min and the aqueous layer was purified by reverse phase prep-HPLC to furnish the desired boronic acid (1.24 g. 42%).

Example 15

2-{3-[8-(2-chloro-3,6-difluorobenzyl)-5,6,7,8-tetrahydropyrazino-[2,3-b]pyrazin-2-yl]phenyl}acetamide

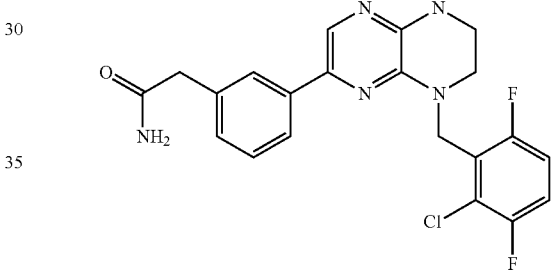

The entitled compound was prepared from 7-bromo-1-(2-chloro-3,6-difluorobenzyl)-1,2,3,4-tetrahydropyrazino[2,3-b]pyrazine and 3-(2-Acetamidyl)phenylboronic acid pinacol ester using Suzuki coupling conditions as described in Example 1.

Example 16

1-(2-chloro-3,6-difluorobenzyl)-7-[2-(4-methylpiperazin-1-yl)pyridine-4-yl]-1,2,3,4-tetrahydropyrazino[2,3-b]pyrazine

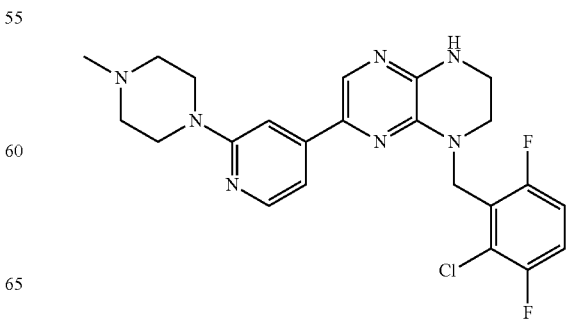

The entitled compound was prepared from 7-bromo-1-(2-chloro-3,6-difluorobenzyl)-1,2,3,4-tetrahydropyrazino[2,3-b]pyrazine and 2-(4-Methylpiperazin-1-yl)pyridine-5-boronic acid pinacol ester using Suzuki coupling conditions as described in Scheme 1.

Example 17

1-(2-chloro-3,6-difluorobenzyl)-7-[1-(piperidin-4-0)-1H-pyrazol-3-yl]-1,2,3,4-tetrahydropyrazino-[2,3-b]pyrazine

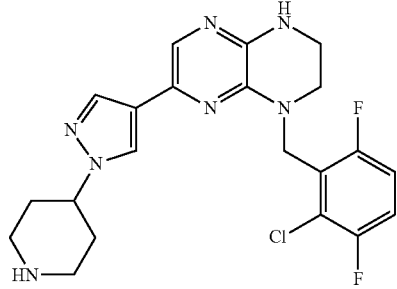 [SMILES: Fc1ccc(F)c(CN2CCNc3ncc(-c4cnn(C5CCNCC5)c4)nc32)c1Cl]

To a solution of 7-bromo-1-(2-chloro-3,6-difluorobenzyl)-1,2,3,4-tetrahydropyrazino[2,3-b]pyrazine (prepared as in Example 1: 0.17 g, 0.45 mmol) and 4-(-pyrazol-1-yl)-N-Boc piperidine boronic acid pinacol ester (prepared as described in WO 2007066185: 0.17 g, 0.45 mmol) in dioxane (2 ml) was added Pd(PPh$_3$)$_4$ (0.026 g, 0.022 mmol) and aq. K2CO3 (2M, 1 mL). The resulting solution was subjected to microwave irradiation at 140° C. for 14 min. The solvent was evaporated and the residue was then chromatographed, eluting with MeOH-DCM (1:9) to yield the desired compound in its BOC protected form; the BOC protected intermediate was then treated with TFA in CH$_2$Cl$_2$. Silica gel column chromatography purification gave the title compound.

Example 18

3-[8-(2-chloro-3,6-difluorobenzyl)-5,6,7,8-tetrahydropyrazino[2,3-b]pyrazin-2-yl]-N-[2-(dimethylamino)ethyl]benzamide

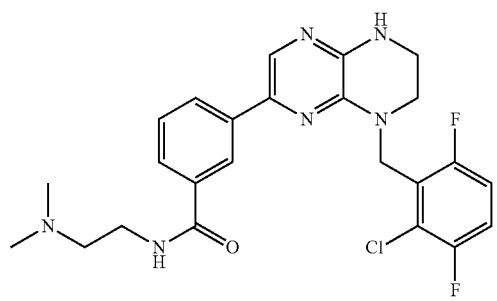 [SMILES: CN(C)CCNC(=O)c1cccc(-c2cnc3c(n2)N(Cc2c(F)ccc(F)c2Cl)CCN3)c1]

The entitled compound was prepared from 7-bromo-1-(2-chloro-3,6-difluorobenzyl)-1,2,3,4-tetrahydropyrazino[2,3-b]pyrazine and N-[2-(N',N'-Dimethylamino)ethyl]benzamide-3-boronic acid pinacol ester using Suzuki coupling conditions as described in Example 1.

Example 19

4-[8-(2-chloro-3,6-difluorobenzyl)-5,6,7,8-tetrahydropyrazino[2,3-b]pyrazin-2-yl]-N-[3-(dimethylamino)propyl]benzamide

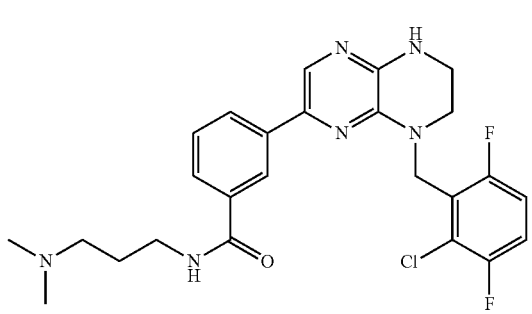 [SMILES: CN(C)CCCNC(=O)c1cccc(-c2cnc3c(n2)N(Cc2c(F)ccc(F)c2Cl)CCN3)c1]

The entitled compound was prepared from 7-bromo-1-(2-chloro-3,6-difluorobenzyl)-1,2,3,4-tetrahydropyrazino[2,3-b]pyrazine and N-[3-(N',N'-Dimethylamino)propyl]benzamide-4-boronic acid, pinacol ester using Suzuki coupling conditions as described in Example 1.

Example 20

4-[8-(2-chloro-3,6-difluorobenzyl)-5,6,7,8-tetrahydropyrazino[2,3-b]pyrazin-2-yl]-N-[2-(diethylamino)ethyl]benzamide

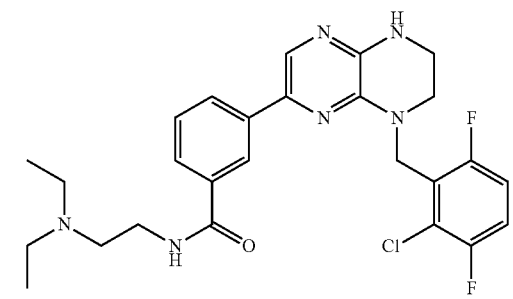 [SMILES: CCN(CC)CCNC(=O)c1cccc(-c2cnc3c(n2)N(Cc2c(F)ccc(F)c2Cl)CCN3)c1]

The entitled compound was prepared from 7-bromo-1-(2-chloro-3,6-difluorobenzyl)-1,2,3,4-tetrahydropyrazino[2,3-b]pyrazine and 4-{[2-(Diethylamino)ethyl]carbamoyl}benzeneboronic acid hydrochloride using Suzuki coupling conditions as described in Scheme 1.

Example 21

{4-[8-(2-chloro-3,6-difluorobenzyl)-5,6,7,8-tetrahydropyrazino[2,3-b]pyrazin-2-yl]phenyl}[(2R)-2-(pyrrolidin-1-ylmethyl)pyrrolidin-1-yl]methanone

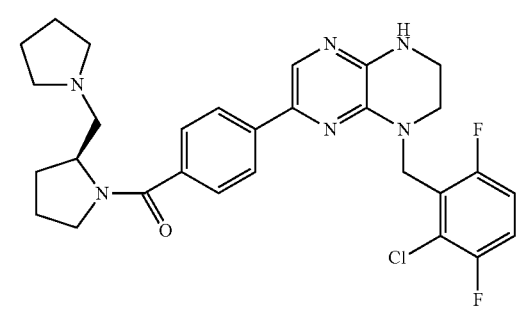 [SMILES: O=C(c1ccc(-c2cnc3c(n2)N(Cc2c(F)ccc(F)c2Cl)CCN3)cc1)N1CCC[C@H]1CN1CCCC1]

The entitled compound was prepared from 7-bromo-1-(2-chloro-3,6-difluorobenzyl)-1,2,3,4-tetrahydropyrazino[2,3-b]pyrazine and [(2R)-2-(pyrrolidin-1-ylmethyl)pyrrolidin-1-yl][4-(4,4,5,5-tetramethyl-1,3,2-dioxaborolan-2-yl)phenyl]methanone using Suzuki coupling conditions as described in Scheme 1.

[(2R)-2-(pyrrolidin-1-ylmethyl)pyrrolidin-1-yl][4-(4,4,5,5-tetramethyl-1,3,2-dioxaborolan-2-yl)phenyl]methanone was prepared as described in Example 14 from 4-(4,4,5,5-tetramethyl[1,3,2]dioxaborolan-2-yl)benzoic acid and (R)-(−)-1-(2-pyrrolidinylmethyl)pyrrolidine.

Example 22

1-(2,6-dichlorobenzyl)-7-[2-(4-methylpiperazin-1-yl)pyridin-4-yl]-1,2,3,4-tetrahydropyrazino[2,3-b]pyrazine

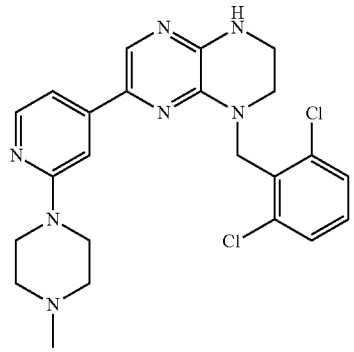 [SMILES: CN1CCN(c2cc(-c3cnc4c(n3)N(Cc3c(Cl)cccc3Cl)CCN4)ccn2)CC1]

The entitled compound was prepared from 7-bromo-1-(2,6-dichlorobenzyl)-1,2,3,4-tetrahydropyrazino[2,3-b]pyrazine and 2-(4-Methylpiperazin-1-yl)pyridine-5-boronic acid pinacol ester using Suzuki coupling conditions as described in Example 1.

7-bromo-1-(2,6-dichlorobenzyl)-1,2,3,4-tetrahydropyrazino[2,3-b]pyrazine was prepared from 2-amino-3,5-dibromopyrazine as described in Example 1 by replacing 2-chloro-3,6-difluorobenzylamine in step 1 with 2,6-dichlorobenzylamine.

Example 23

1-(2,5-difluorobenzyl)-7-[2-(4-methylpiperazin-1-yl)pyridin-4-yl]-1,2,3,4-tetrahydropyrazino[2,3-b]pyrazine

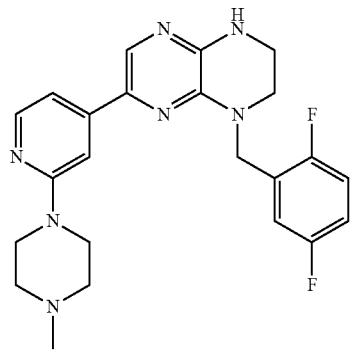 [SMILES: CN1CCN(c2cc(-c3cnc4c(n3)N(Cc3cc(F)ccc3F)CCN4)ccn2)CC1]

The entitled compound was prepared from 7-bromo-1-(2,5-difluorobenzyl)-1,2,3,4-tetrahydropyrazino[2,3-b]pyrazine and 2-(4-Methylpiperazin-1-yl)pyridine-5-boronic acid pinacol ester using Suzuki coupling conditions as described in Example 1.

7-bromo-1-(2,5-difluorobenzyl)-1,2,3,4-tetrahydropyrazino[2,3-b]pyrazine was prepared as described in Example 1, from 2-amino-3,5-dibromopyrazine as described in Example 1 by replacing 2-chloro-3,6-difluorobenzylamine in step 1 with 2,5-difluorobenzylamine.

Example 24

1-[5-chloro-2-(trifluoromethyl)benzyl]-7-[2-(4-methylpiperazin-1-yl)pyridin-4-yl]-1,2,3,4-tetrahydropyrazino[2,3-b]pyrazine

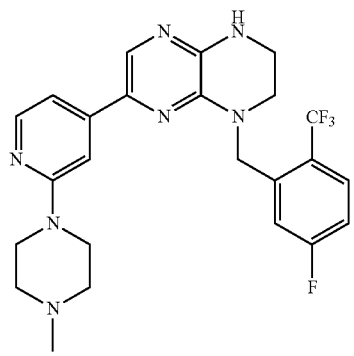 [SMILES: CN1CCN(c2cc(-c3cnc4c(n3)N(Cc3cc(F)ccc3C(F)(F)F)CCN4)ccn2)CC1]

The entitled compound was prepared from 7-bromo-1-[5-chloro-2-(trifluoromethyl)benzyl]-1,2,3,4-tetrahydropyrazino[2,3-b]pyrazine and 2-(4-Methylpiperazin-1-yl)pyridine-5-boronic acid pinacol ester using Suzuki coupling conditions as described in Example 1.

7-bromo-1-[5-chloro-2-(trifluoromethyl)benzyl]-1,2,3,4-tetrahydropyrazino[2,3-b]pyrazine was prepared as described in Example 1 from 2-amino-3,5-dibromopyrazine as described in Example 1 by replacing 2-chloro-3,6-difluorobenzylamine in step 1 with 5-chloro-2-trifluoromethyl-benzylamine.

Example 25

1-(2-chloro-3,6-difluorobenzyl)-8-methyl-7-[3-(morpholin-4-0)phenyl]-1,2,3,4-tetrahydropyrido[2,3-b]pyrazine

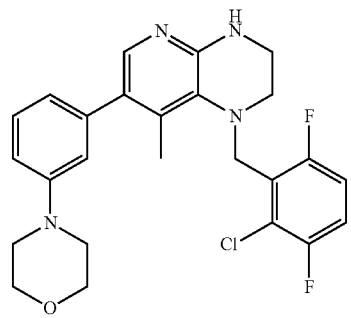 [SMILES: Cc1c(-c2cccc(N3CCOCC3)c2)cnc2c1N(Cc1c(F)ccc(F)c1Cl)CCN2]

5-bromo-4-methylpyridine-2,3-diamine: 2-Amino-5-bromo-4-methyl-3-nitropyridine (5 g) was dissolved in 6M HCl (50 mL) and iron powder was slowly added. The reaction was then heated to reflux until no starting material was seen via HPLC. The reaction was then cooled to room temperature and filtered. The bis-HCl salt was dried to a cream solid which was then taken up in EtOAc, neutralized with 50% NaOH solution to yield 5-bromo-4-methylpyridine-2,3-diamine as a free base.

7-bromo-8-methylpyrido[2,3-b]pyrazine: 5-bromo-4-methylpyridine-2,3-diamine (0.21 g, 1 mmol) was dissolved in a mixture of EtOH—H2O; to this was added aqueous glyoxal 40% (0.2 ml, 4 mmol) and the resulting mixture was refluxed for 1 h. Upon cooling to room temperature, water was then added. The product was separated, filtered and washed with excess water yielded 7-bromo-8-methylpyrido[2,3-b]pyrazine as a sufficiently enough pure material (0.21 g) for the next step.

7-bromo-8-methyl-1,2,3,4-tetrahydropyrido[2,3-b]pyrazine: 7-bromo-8-methylpyrido[2,3-b]pyrazine (0.21 g) and NaBH4 (0.21 g) in THF (1.4 ml) was treated with trifluoroacetic acid (1.4 ml) at room temperature over a period of 15 min. Stirring continued for additional 45 min then water was added followed by 50% sodium hydroxide. The residue was extracted into $CH_2Cl_2$, filtered, dried, and concentrated to furnish the desired product (0.12 g).

7-bromo-1-(2-chloro-3,6-difluorobenzyl)-8-methyl-1,2,3,4-tetrahydropyrido[2,3-b]pyrazine: 1,2,3,4-Tetrahydro-6-methyl-7-bromo pyrido[2,3-b]pyrazine (0.15 g, 1 mmol), 2-chloro 3,6-difluoro-benzyl bromide (0.16 g, 1.05 mmol), KI (0.016 mmol, 0.01 g) in acetonitrile was subjected to microwave irradiation at 130° C. for 20 min. The solvent was stripped off and the crude residue was re-dissolved in $CH_2Cl_2$, washed with aqueous $NaHCO_3$ solution. Upon drying, the residue was chromatographed, eluting with a mixture of hexanes-EtOAc (7:3) to furnish pure desired product (0.086 g 23%). The undesired N-alkylation product was also obtained and the structural differentiation was based on NOE NMR experiment.

1-(2-chloro-3,6-difluorobenzyl)-8-methyl-7-[3-(morpholin-4-yl)phenyl]-1,2,3,4-tetrahydropyrido[2,3-b]pyrazine:
To a solution of 7-bromo-1-(2-chloro-3,6-difluorobenzyl)-8-methyl-1,2,3,4-tetrahydropyrido[2,3-b]pyrazine (0.048 g, 0.124 mmol) and 3-morpholinophenylboronic acid pinacol ester (0.035 g, 0.124 mmol) in DMF-$H_2O$ (9:1, 2 mL) was added $PdCl_2(PPh_3)_2$ (0.0087 g, 0.0124 mmol) and K2CO3 (0.043 mg, 0.31 mmol). The resulting solution was subjected to microwave irradiation at 125° C. for 20 min. The solvent was filtered using a PTFE frit and then directly purified by prep HPLC using a gradient mixture of ACN—H2O— 0.1% TFA to yield the desired product (0.023 g 40%).

Example 26

1-(2-chloro-3,6-difluorobenzyl)-8-methyl-7-[1-(piperidin-4-yl)-1H-pyrazol-4-yl]-1,2,3,4-tetrahydropyrido[2,3-b]pyrazine

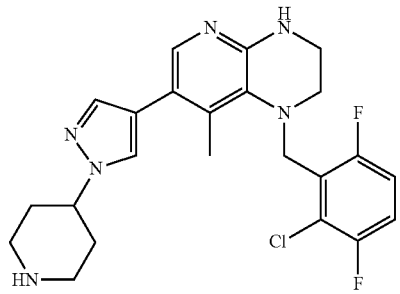 [SMILES: Cc1c(-c2cnn(C3CCNCC3)c2)cnc2c1N(Cc1c(F)ccc(F)c1Cl)CCN2]

To a solution of 7-bromo-1-(2-chloro-3,6-difluorobenzyl)-8-methyl-1,2,3,4-tetrahydropyrido[2,3-b]pyrazine (prepared as in Example 25: 0.17 g, 0.45 mmol) and 4-(-pyrazol-1-yl)-N-Boc piperidine boronic acid pinacol ester (prepared as described in WO 2007066185: 0.17 g, 0.45 mmol) in dioxane (2 ml) was added $Pd(PPh_3)_4$ (0.026 g, 0.022 mmol) and aq. $K_2CO_3$ (2M, 1 mL). The resulting solution was subjected to microwave irradiation at 140° C. for 14 min. The solvent was evaporated and the residue was then chromatographed, eluting with MeOH-DCM (1:9) to yield the desired compound in its BOC protected form. The BOC protected intermediate was then treated with TFA in $CH_2Cl_2$. Silica gel column chromatography purification gave the title compound.

Example 27

1-(2-chloro-3,6-difluorobenzyl)-8-methyl-7-{1-[2-(morpholin-4-0)ethy]-1H-pyrazol-4-yl}-1,2,3,4-tetrahydropyrido[2,3-b]pyrazine

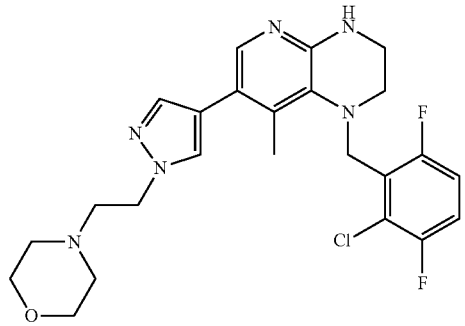 [SMILES: Cc1c(-c2cnn(CCN3CCOCC3)c2)cnc2c1N(Cc1c(F)ccc(F)c1Cl)CCN2]

The entitled compound can be prepared from 7-bromo-1-(2-chloro-3,6-difluorobenzyl)-8-methyl-1,2,3,4-tetrahydropyrido[2,3-b]pyrazine and 1-(2-morpholinoethyl)-1H-pyrazole-4-boronic acid pinacol ester as described in Example 25.

Example 28

5-[1-(2-chloro-3,6-difluorobenzyl)-8-methyl-1,2,3,4-tetrahydropyrido[2,3-b]pyrazin-7-yl]-N-[2-(morpholin-4-yl)ethyl]pyridin-2-amine

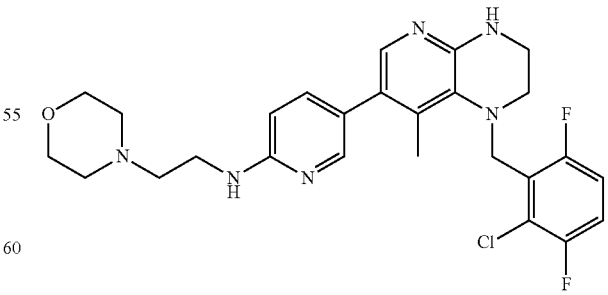

The entitled compound can be prepared from 7-bromo-1-(2-chloro-3,6-difluorobenzyl)-8-methyl-1,2,3,4-tetrahydropyrido[2,3-b]pyrazine and 2-(2-morpholinoethylamino)pyridine-5-boronic acid pinacol ester as described in example 25.

Example 29

1-(2-chloro-3,6-difluorobenzyl)-8-methyl-7-{4-[2-(4-methylpiperazin-1-yl)ethoxy]phenyl}-1,2,3,4-tetrahydropyrido[2,3-b]pyrazine

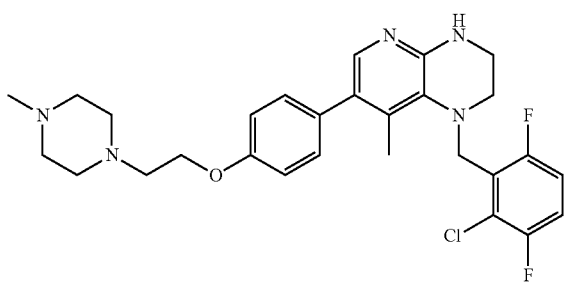 [SMILES: Cc1c(-c2ccc(OCCN3CCN(C)CC3)cc2)cnc2c1N(Cc1c(F)ccc(F)c1Cl)CCN2]

The entitled compound can be prepared from 7-bromo-1-(2-chloro-3,6-difluorobenzyl)-8-methyl-1,2,3,4-tetrahydropyrido[2,3-b]pyrazine and 1-methyl-4-{2-[4-(4,4,5,5-tetramethyl-[1,3,2]-dioxaborolan-2-yl)-phenoxy]-ethyl}-piperazine as described in example 25.

Example 30

9-(2-chloro-3,6-difluorobenzyl)-2-[3-(morpholin-4-yl)phenyl]-6,7,8,9-tetrahydro-5H-pyrazino[2,3-b][1,4]diazepine

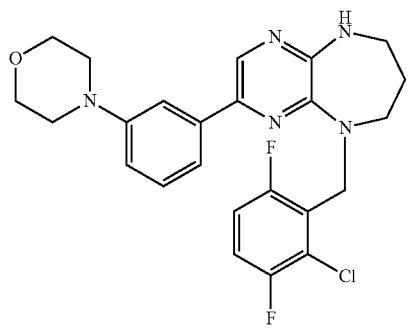 [SMILES: Fc1ccc(F)c(CN2CCCNc3ncc(-c4cccc(N5CCOCC5)c4)nc32)c1Cl]

Methyl N-(3,5-dibromopyrazin-2-yl)-β-alaninate: A solution of 2-amino-3,5-dibromopyrazine (40 mmol, 10 g) and methyl acrylate (56 mmol, 4.82 g) in pyridine (60 mL) was heated at 100° C. overnight. Upon cooling, volatile components were removed on rotavap and the residue was directly used in the next step.

Methyl N-{5-bromo-3-[(2-chloro-3,6-difluorobenzyl)amino]pyrazin-2-yl}-β-alaninate was prepared from methyl N-(3,5-dibromopyrazin-2-yl)-β-alaninate and 2-chloro-3,6-difluorobenzylamine in the presence of N,N-diethylisopropylamine as described in Example 1.

3-Bromo-5-(2-chloro-3,6-difluorobenzyl)-5,7,8,9-tetrahydro-6H-pyrazino[2,3-b][1,4]diazepin-6-one: A solution of methyl N-{5-bromo-3-[(2-chloro-3,6-difluorobenzyl)amino]pyrazin-2-yl}-β-alaninate in HOAc was heated at reflux for 4 hrs. After volatile components were removed on rotavap, the residue was taken in to a mixture of EtOAc and aq. NaHCO₃. The combined organic layers from extraction was dried, concentrated, and then purified by silica gel column chromatography (EtOAc/Hexanes 4:1) to furnish 3-bromo-5-(2-chloro-3,6-difluorobenzyl)-5,7,8,9-tetrahydro-6H-pyrazino[2,3-b][1,4]diazepin-6-one.

2-Bromo-9-(2-chloro-3,6-difluorobenzyl)-6,7,8,9-tetrahydro-5H-pyrazino[2,3-b][1,4]diazepine was prepared from 3-bromo-5-(2-chloro-3,6-difluorobenzyl)-5,7,8,9-tetrahydro-6H-pyrazino[2,3-b][1,4]diazepin-6-one by reducing the amide functionality using BH₃.Me₂S as described in Example 1.

9-(2-chloro-3,6-difluorobenzyl)-2-[3-(morpholin-4-yl)phenyl]-6,7,8,9-tetrahydro-5H-pyrazino[2,3-b][1,4]diazepine was prepared from 2-bromo-9-(2-chloro-3,6-difluorobenzyl)-6,7,8,9-tetrahydro-5H-pyrazino[2,3-b][1,4]diazepine and 3-morpholinophenylboronic acid pinacol ester using standard Suzuki conditions as described in Example 1 or 2.

Example 31

3-[9-(2-chloro-3,6-difluorobenzyl)-6,7,8,9-tetrahydro-5H-pyrazino[2,3-b][1,4]diazepin-2-yl]-N-[2-(morpholin-4-yl)ethyl]benzamide

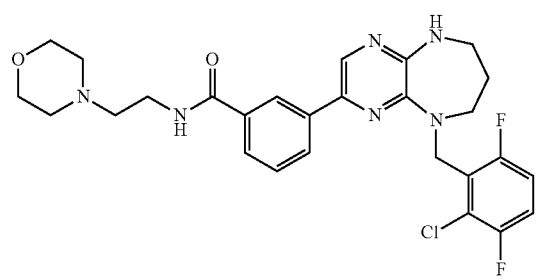 [SMILES: O=C(NCCN1CCOCC1)c1cccc(-c2cnc3c(n2)N(Cc2c(F)ccc(F)c2Cl)CCCN3)c1]

The entitled compound can be prepared from 2-Bromo-9-(2-chloro-3,6-difluorobenzyl)-6,7,8,9-tetrahydro-5H-pyrazino[2,3-b][1,4]diazepine and 3-(2-morpholinoethylcarbamoyl)phenyl boronic acid as described in example 1 or 30.

Example 32

{3-[9-(2-chloro-3,6-difluorobenzyl)-6,7,8,9-tetrahydro-5H-pyrazino[2,3-b][1,4]diazepin-2-yl]phenyl}[4-(2-hydroxyethyl)piperazin-1-yl]-methanone

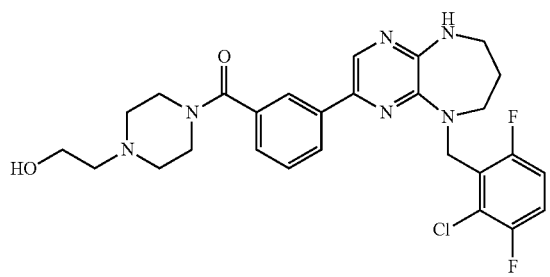 [SMILES: O=C(c1cccc(-c2cnc3c(n2)N(Cc2c(F)ccc(F)c2Cl)CCCN3)c1)N1CCN(CCO)CC1]

The entitled compound can be prepared from 2-Bromo-9-(2-chloro-3,6-difluorobenzyl)-6,7,8,9-tetrahydro-5H-pyrazino[2,3-b][1,4]diazepine and 3-(4-(2-hydroxyethyl)piperazine-1-carbonyl)phenylboronic acid as described in example 1 or 30.

Example 33

9-(2-chloro-3,6-difluorobenzyl)-2-(2-methyl-1,2,3,4-tetrahydroisoquinolin-6-0)-6,7,8,9-tetrahydro-5H-pyrazino[2,3-b][1,4]diazepine

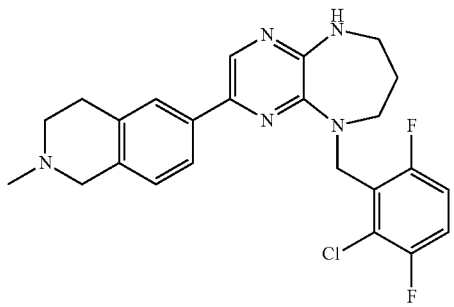 [SMILES: CN1CCc2cc(-c3cnc4c(n3)N(Cc3c(F)ccc(F)c3Cl)CCCN4)ccc2C1]

The entitled compound can be prepared from 2-Bromo-9-(2-chloro-3,6-difluorobenzyl)-6,7,8,9-tetrahydro-5H-pyrazino[2,3-b][1,4]diazepine and 2-methyl-6-(4,4,5,5-tetramethyl-1,3,2-dioxaborolan-2-yl)-1,2,3,4-tetrahydroquinoline as described in example 1 or 30.

Example 34

6-[9-(2-chloro-3,6-difluorobenzyl)-6,7,8,9-tetrahydro-5H-pyrazino[2,3-b][1,4]diazepin-2-yl]-N-methylquinazolin-2-amine

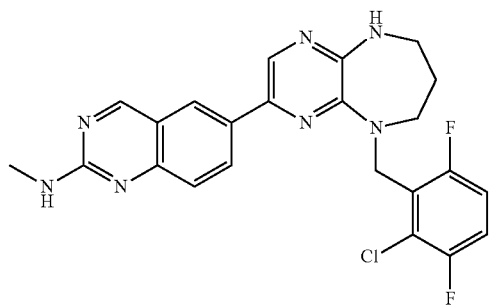 [SMILES: CNc1ncc2cc(-c3cnc4c(n3)N(Cc3c(F)ccc(F)c3Cl)CCCN4)ccc2n1]

The entitled compound can be prepared from 2-Bromo-9-(2-chloro-3,6-difluorobenzyl)-6,7,8,9-tetrahydro-5H-pyrazino[2,3-b][1,4]diazepine and N-methyl-6-(4,4,5,5-tetramethyl-1,3,2-dioxaborolan-2-yl)-quinazolin-2-amine as described in example 1 or 30.

Example 35

9-(2-chloro-3,6-difluorobenzyl)-2-{4-[2-(1H-imidazol-1-yl)ethoxy]phenyl}-6,7,8,9-tetrahydro-5H-pyrazino[2,3-b][1,4]diazepine

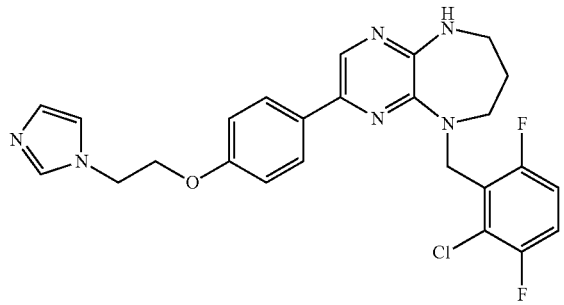 [SMILES: Fc1ccc(F)c(CN2CCCNc3ncc(-c4ccc(OCCn5ccnc5)cc4)nc32)c1Cl]

The entitled compound can be prepared from 2-Bromo-9-(2-chloro-3,6-difluorobenzyl)-6,7,8,9-tetrahydro-5H-pyrazino[2,3-b][1,4]diazepine and 4-(2-(1H-imidazol-1-yl)ethoxy)phenyl boronic acid as described in example 1 or 30.

Example 36

Biological Evaluation of Compounds

Compounds of this invention are evaluated in a variety of assays to determine their biological activities. For example, the compounds of the invention are tested for their ability to inhibit various protein kinases of interest. Some of the compounds tested displayed potent nanomolar activity against the kinase Alk. Furthermore some of these compounds were screened for antiproliferative activity in the human Karpas-299 and in the human SU-DHL-1 lymphoma cell lines. The compounds can also be evaluated for their cytotoxic or growth inhibitory effects on tumor cells of interest, e.g., as described in more detail below and as shown above for some representative compounds. See e.g., WO 03/000188, pages 115-136, the full contents of which are incorporated herein by reference.

Some representative compounds of this invention are depicted below:

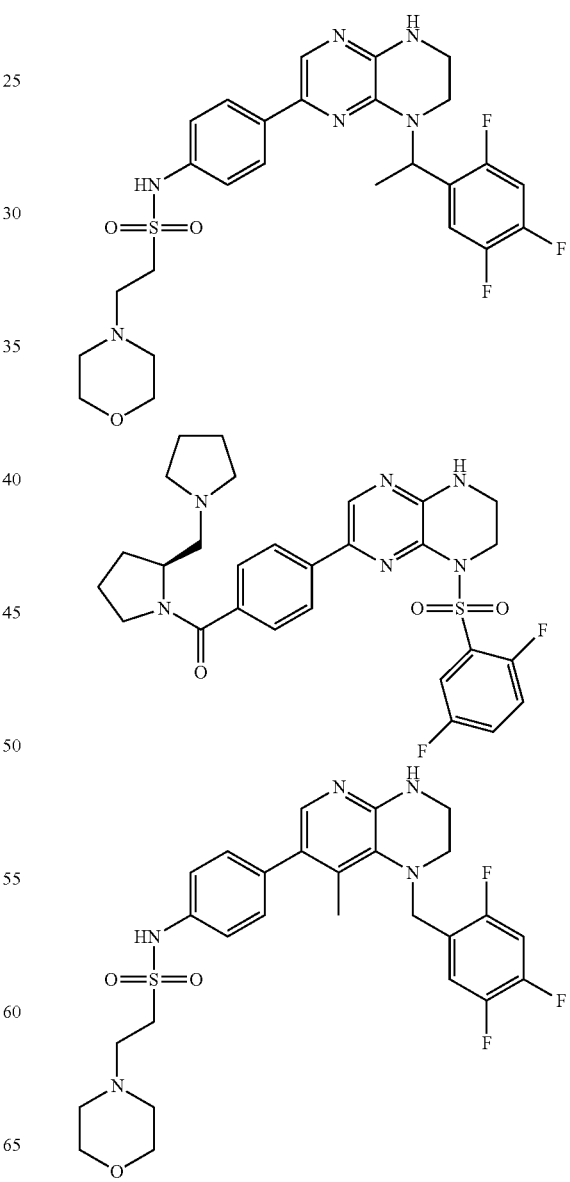

135
-continued
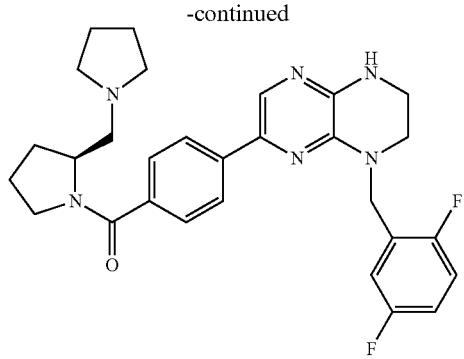
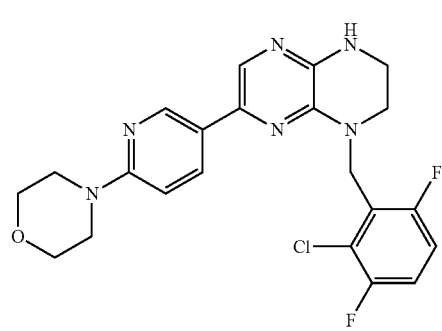
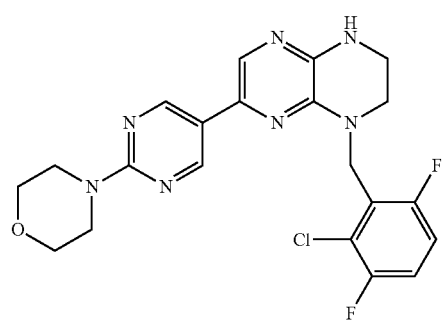
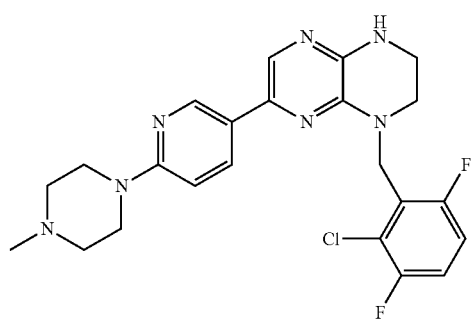
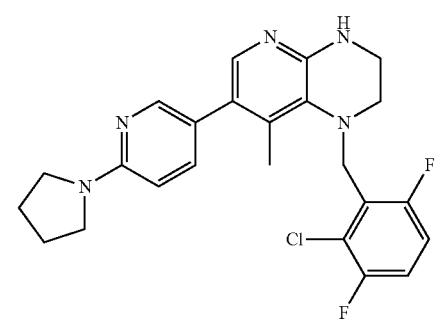
136
-continued
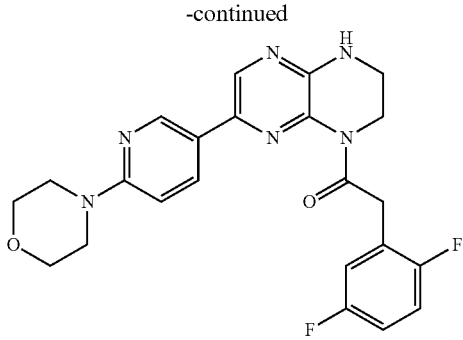
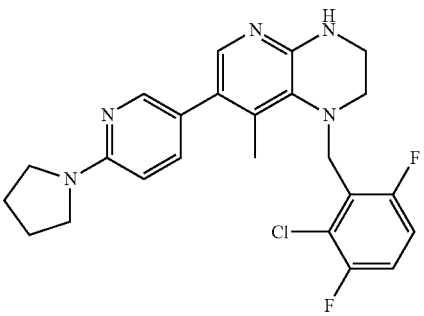
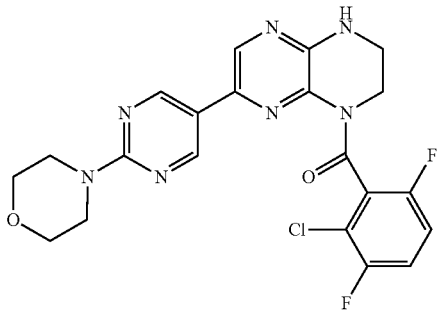
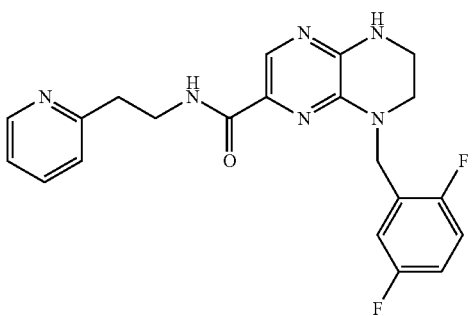
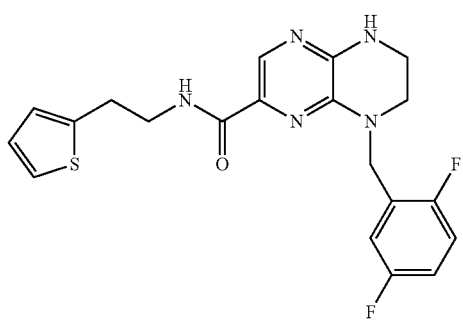

137
-continued
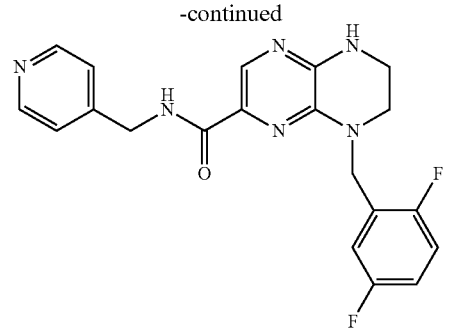
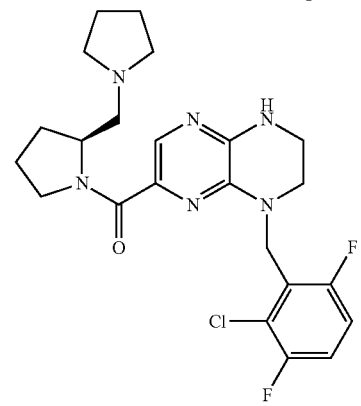
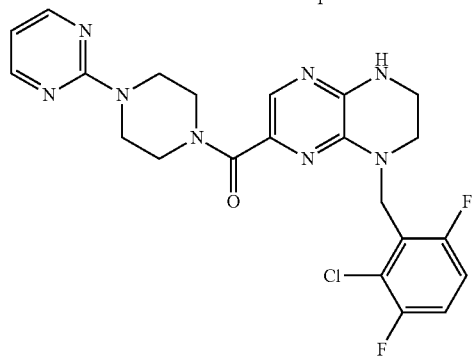
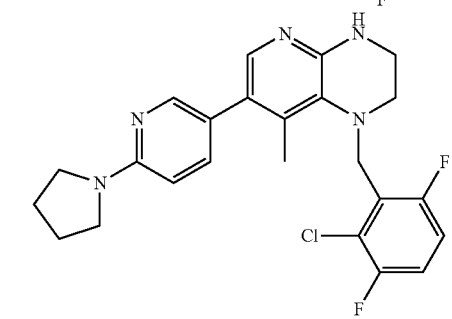
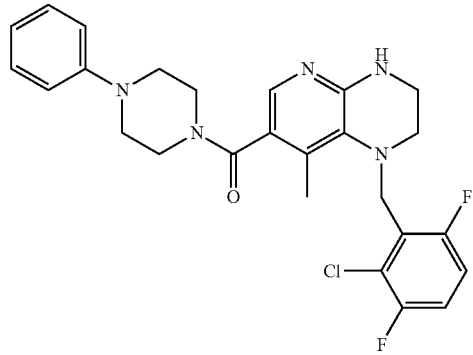
138
-continued
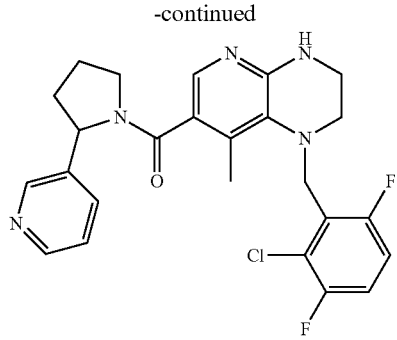
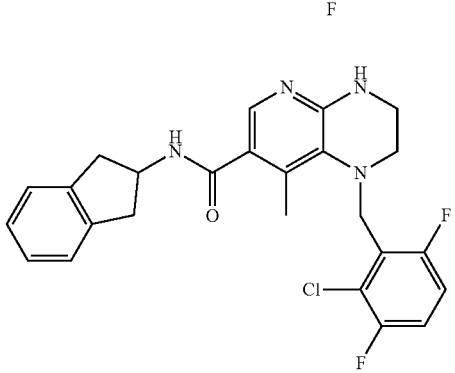
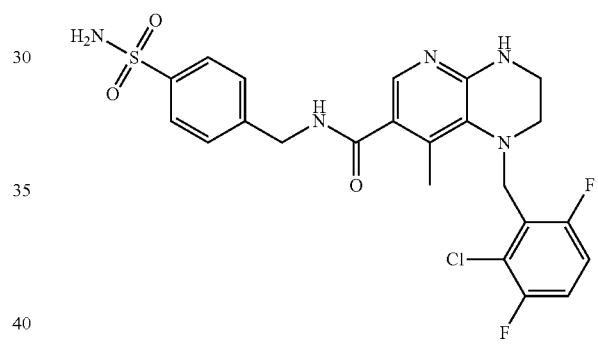
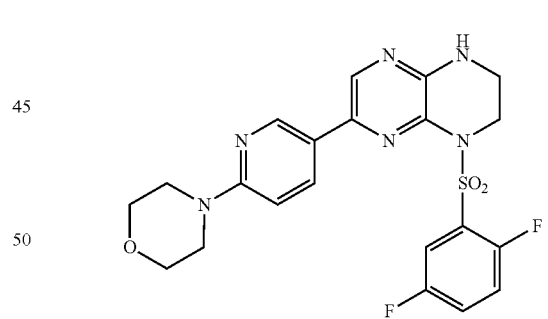
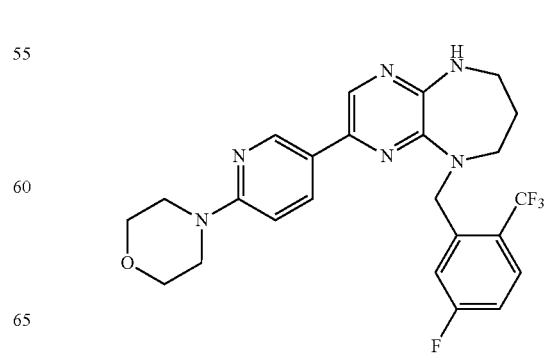

139
-continued
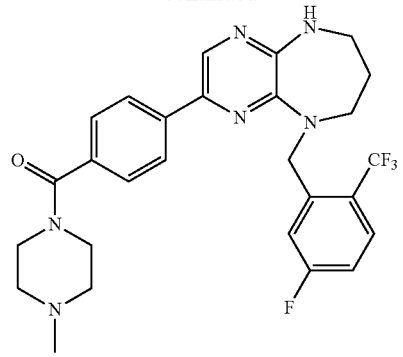
140
-continued
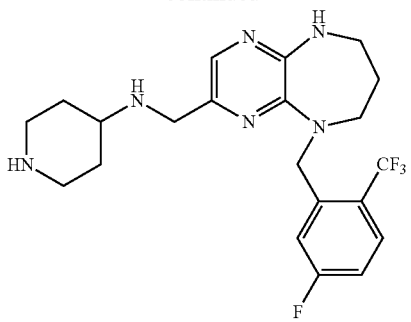
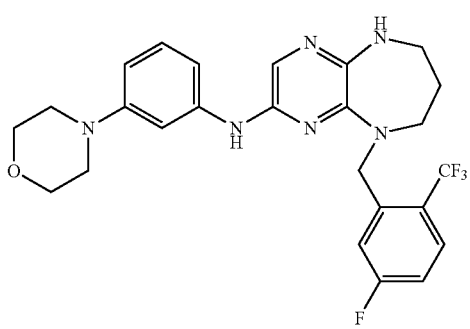
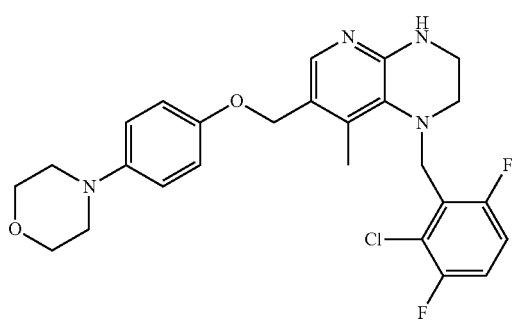
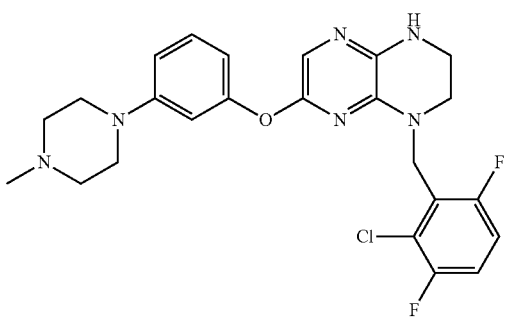
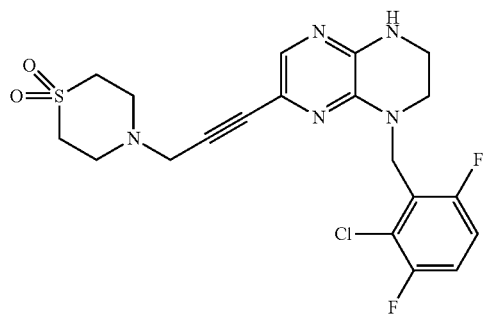

-continued

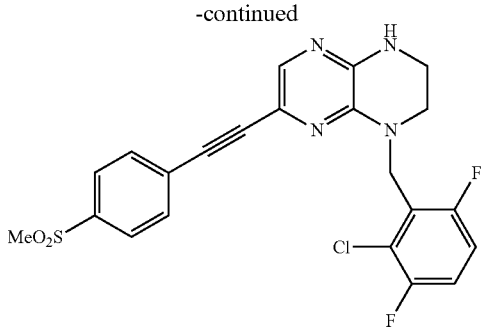

Kinase Inhibition

More specifically, the compounds described herein are screened for kinase inhibition activity as follows. Kinases suitable for use in the following protocol include, but are not limited to: ALK, Jak2, b-Raf, c-Met, Tie-2, FLT3, Abl, Lck, Lyn, Src, Fyn, Syk, Zap-70, Itk, Tec, Btk, EGFR, ErbB2, Kdr, FLT1, Tek, InsR, and AKT.

Kinases are expressed as either kinase domains or full length constructs fused to glutathione S-transferase (GST) or polyHistidine tagged fusion proteins in either E. coli or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition can be measured by established protocols (see e.g., Braunwalder et al., 1996). In such cases, the transfer of $^{33}PO_4$ from ATP to the synthetic substrates poly(Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization and homogeneous time-resolved fluorescence. Alternatively, kinase activity can be measured using antibody-based methods in which an antibody or polypeptide is used as a reagent to detect phosphorylated target polypeptide.

For additional background information on such assay methodologies, see e.g., Braunwalder et al., 1996, Anal. Biochem. 234(1):23; Cleaveland et al., 1990, Anal Biochem. 190(2):249 Gish et al. (1995). Protein Eng. 8(6):609 Kolb et al. (1998). Drug Discov. Toda V. 3:333 Lehr et al. (1996). Gene 169(2):27527-87 Seethala et al. (1998). Anal Biochem. 255(2):257 Wu et al. (2000).

The inhibition of ALK tyrosine kinase activity can be demonstrated using known methods. For example, in one method, compounds can be tested for their ability to inhibit kinase activity of baculovirus-expressed ALK using a modification of the ELISA protocol reported for trkA in Angeles, T. S. et al., Anal. Biochem. 1996, 236, 49-55, which is incorporated herein by reference. Phosphorylation of the substrate, phospholipase C-gamma (PLC-γ) generated as a fusion protein with glutathione-5-transferase (GST) as reported in rotin, D. et al., EMBO J. 1992, 11, 559-567, which is incorporated by reference, can be detected with europium-labeled anti-phosphotyrosine antibody and measured by time-resolved fluorescence (TRF). In this assay, 96-well plate is coated with 100 µL/well of 10 µg/mL substrate (phospholipase C-γ in tris-buffered saline (TBS). The assay mixture (total volume=100 µL/well) consisting of 20 nM HEPES (pH 7.2, 1 µMATP ($K_m$ level), 5 nM $MnCl_2$, 0.1% BSA, 2.5% DMSO, and various concentrations of test compound is then added to the assay plate. The reaction is initiated by adding the enzyme (30 ng/mL ALK) and is allowed to proceed at 37 degrees C. for 15 minutes. Detection of the phosphorylated product can be performed by adding 100 µL/well of Eu—N1 labeled PT66 antibody (Perkim Elmer #AD0041). Incubation at 37 degrees C. then proceeds for one hour, followed by addition of 100□L enhancement solution (for example Wallac #1244-105). The plate is gently agitated and after thirty minutes, the fluorescence of the resulting solution can be measured (for example using EnVision 2100 (or 2102) multilabel plate reader from Perkin Elmer).

Data analysis can then be performed. $IC_{50}$ values can be calculated by plotting percent inhibition versus $log_{10}$ of concentration of compound.

The inhibition of ALK tyrosine kinase activity can also be measured using the recombinant kinase domain of the ALK in analogy to VEDG-R kinase assay described in J. Wood et al., Cancer Res 2000, 60, 2178-2189. In vitro enzyme assays using GST-ALK protein tyrosine kinase can be performed in 96-well plate as a filter binding assay in 20 mMTris.HCl, pH 7.5, 3 mM $MgCl_2$, 10 mM $MnCl_2$, 1 nM DTT, 0.1 µCi/assay (=30 µl) [γ-$^{33}P$]-ATP, 2 µM ATP, 3 µg/mL poly (Glu, tyr 4:1) Poly-EY (sigma P-0275), 1% DMSO, 25 ng ALK enzyme. Assays can be incubated for 10 min, at ambient temperature. Reactions can be terminated by adding 50 µL of 125 mM EDTA, and the reaction mixture can be transferred onto a MAIP Multiscreen plate (Millipore, Bedford, Mass.) previously wet with methanol, and rehydrated for 5 minutes with water. Following washing (0.5% $H_3PO_4$), plates can be counted in a liquid scintillation counter. $IC_{50}$ values are calculated by linear regression analysis of the percentage inhibition.

$IC_{50}$ values in the low nanomolar range have been observed for compounds of this invention against various kinases, including ALK and Met.

Cell-Based Assays

Certain compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of this invention, the terms "anti-tumor" and "anti-cancer" activity are used interchangeably.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability)(e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Particularly preferred compounds are tetrazolium salts and include without limitation MIT (3-(4,5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1):73-81, 1999). More commonly used assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Other methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

In addition, a wide variety of cell types may be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

While the cell line is preferably mammalian, lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, others may be used as well.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem. Biol. 6:541-51; incorporated herein by reference) used HeLa cells containing an inducible variant of GFP to detect compounds that inhibited expression of the GFP, and thus inhibited cell proliferation.

An example of cell-based assay is shown as below. The cell lines that can be used in the assay are Ba/F3, a murine pro-B cell line, which has been stably transfected with an expression vector pClneo™ (Promega Corp., Madison Wis.) coding for NPM-ALK and subsequent selection of G418 resistant cells. Non-transfected Ba/F3 cells depend on IL-3 for cell survival. In constrast NPM-ALK expressing Ba/F3 cells (named Ba/F3-NPM-ALK) can proliferate in the absence of IL-3 because they obtain proliferative signal through NMP-ALK kinase. Putative inhibitors of NPM-ALK kinase therefore abolish the growth signal and result in antiproliferative activity. The antiproliferative activity of inhibitors of the NPM-ALK kinase can however be overcome by addition of IL-3 which provides growth signals through an NPM-ALK independent mechanism. For an analogous cell system using FLT3 kinase see E. Weisberg et al. *Cancer cell*, 2002, 1, 433-443. The inhibitory activity of the compounds of formula I can be determined as follows: BaF3-NPM-ALK cells (15,000/microtitre plate well) can be transferred to a 96-well microtitre plates. The test compound (dissolved in DMSO) is then added in a series of concentrations (dilution series) in such a manner that the final concentration of DMSO is not greater than 1% (v/v). After the addition, the plates can be incubated for two days during which the control cultures without test compound are able to undergo two cell-division cycles. The growth of BaF3-NPM-ALK cells can be measured by means of Yopro™ staining (T Idziorek et al., *J. Immunol. Methods* 1995, 185, 249-258). 25 µl of lysis buffer consisting of 20 mM sodium citrate, pH 4.0, 26.8 nM sodium chloride, 0.4% NP40, 20 mM EDTA and 20 mM is added into each well. Cell lysis is completed within 60 minutes at room temperature and total amount of Yopro bound to DNA is determined by measurement using for example a CytoFluor II 96-well reader (PerSeptive Biosystems). The $IC_{50}$ can be determined by a computer aided system using the formula:

$$IC_{50}=[(ABS_{test}-ABS_{start})/(ABS_{control}-ABS_{start})]\times 100$$

in which ABS is absorption. The $IC_{50}$ value in such an experiment is given as that concentration of the test compound in question that results in a cell count that is 50% lower than that obtained using the control without inhibitor.

The antiproliferative action of the compounds of this invention can also be determined in the human KARPAS-299 lymphoma cell line by means of an immunoblot as described in W G Dirks et al. *Int. J Cancer* 2002, 100, 49-56., using the methodology described above for the BaF3-NPM-ALK cell line.

In another example, antiproliferative activity can be determined using KARPAS-299 lumphoma cell line in the following procedure: Compounds of the invention were incubated with the cells for 3 days, and the number of viable cells in each well was measured indirectly using an MTS tetrazolium assay (Promega). This assay is a colorimetric method for determining the number of viable cells through measurement of their metabolic activity. For example the detection of the product of the enzymatic conversion of tetrazolium salts into blue formazan derivatives is achieved by measuring absorbance at 490 nm using a plate reader. 40 μL of the MTS reagent was added to all wells except the edge wells and then the plates were returned to the incubator at 37° C. for 2 hours. The absorbance in each well was then measured at 490 nm using a Wallac Victor²V plate reader. The $IC_{50}$ was calculated by determining the concentration of compound required to decrease the MTS signal by 50% in best-fit curves using Microsoft XLfit software, by comparing with baseline, the DMSO control, as 0% inhibition.

Several compounds of Formula I exhibit inhibitory activity with an $IC_{50}$ in the range of 10 nM to 200 nM.

Compounds identified by such cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (Cancer Metastasis Rev. 17:301-304, 1998-99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207-218, 1997; incorporated herein by reference).

Example 37

Pharmaceutical Compositions

Representative pharmaceutical dosage forms of the compounds of this invention (the active ingredient being referred to as "Compound"), are provided for therapeutic or prophylactic use in humans:

| (a) Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyffolidone (5% w/v paste) | 2.25 |
| Magnesium stearate | 3.0 |

| (c) Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

| (d) Capsule | mg/capsule |
|---|---|
| Compound | 10 |
| Lactose Ph. Eur | 488.5 |
| Magnesium | 1.5 |

| (e) Injection I | (50 mg/ml) |
|---|---|
| Compound | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol | I mg/ml |
|---|---|
| Compound | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound | 40 mg |
| Ethanol | 300 μl |
| Water | 300 μl |
| 1-Dodecylazacycloheptan one | 50 μl |
| Propylene glycol | to 1 ml |

Note: These formulations may be prepared using conventional procedures well known in the pharmaceutical art. The

The invention claimed is:

1. A compound of Formula I:

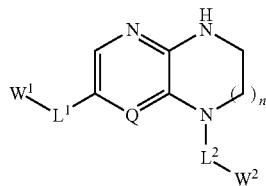

Formula I or a tautomer or pharmaceutically acceptable salt thereof, wherein $W^1$ represents an aryl, a 3- to 8-membered carbocyclyl, a 5-, 6- or 7-membered heterocyclic or heteroaryl ring comprising carbon atoms and 1-4 heteroatoms independently selected from O, N, P(O) and S(O)$_r$, and $W^1$ is optionally substituted with 1-5 $R^a$ groups;

$W^2$ represents an aryl or a 5- or 6-membered heteroaryl ring comprising carbon atoms and 1-3 heteroatoms independently selected from O, N, P(O) and S(O)$_r$, and $W^2$ is optionally substituted with 1-5 $R^b$ groups;

Q is N;

$L^1$ and $L^2$ are independently selected from a bond, $C_{1-6}$-alkyl, O—$C_{0-6}$-alkyl, $NR^1$—$C_{0-6}$-alkyl, C(O)$NR^1$—$C_{0-6}$-alkyl, $NR^1$C(O)—$C_{0-6}$-alkyl, $C_{2-6}$-alkenyl, $C_{2-6}$-alkynyl, $C_{0-6}$-alkyl-S(O)$_r$, $C_{0-6}$-alkyl-S(O)$_2NR^1$, $C_{0-6}$-alkyl-$NR^1$S(O)$_2$, C(O)—$C_{0-6}$-alkyl, OC(O)$NR^1$—$C_{0-6}$-alkyl, $NR^1$C(O)O—$C_{0-6}$-alkyl, $NR^1$C(O)$NR^1$—$C_{0-6}$-alkyl; and the linkers $L^1$ and $L^2$ can be included in either direction;

$R^a$ and $R^b$ are independently selected from halo, —CN, —NO$_2$, —$R^1$, —OR$^2$, —O—$NR^1R^2$, —$NR^1R^2$, —$NR^1$—$NR^1R^2$, —$NR^1$—OR$^2$, —C(O)YR$^2$, —OC(O)YR$^2$, —$NR^1$C(O)YR$^2$, —SC(O)YR$^2$, —$NR^1$C(=S)YR$^2$, OC(=S)YR$^2$, —C(=S)YR$^2$, —YC(=NR$^1$)YR$^2$, —YC(=N—OR$^1$)YR$^2$, —YC(=N—NR$^1R^2$)YR$^2$, —YP(=O)(YR$^3$)(YR$^3$), —Si(R$^3$)$_3$, —$NR^1$SO$_2R^2$, —S(O)$_rR^2$, —SO$_2NR^1R^2$ and —$NR^1$SO$_2NR^1R^2$; alternatively two adjacent $R^a$ or two adjacent $R^b$ groups form with the atoms to which they are attached, a 5-, 6- or 7-membered saturated, partially saturated or unsaturated ring, which is optionally substituted and which contains 0-3 heteroatoms selected from N, O, P(O) and S(O)$_r$;

each Y is independently a bond, —O—, —S— or —$NR^1$—;

r is 0, 1 or 2;

n is 1 or 2;

each occurrence of $R^1$ and $R^2$ is independently selected from H, alkyl, alkenyl, alkynyl, cycloalkyl, cycloalkenyl, cycloalkynyl, aryl, heterocyclic and heteroaryl;

each occurrence of $R^3$ is independently selected from alkyl, alkenyl, alkynyl, cycloalkyl, cycloalkenyl, cycloalkynyl, aryl, heterocyclic and heteroaryl;

alternatively, each $NR^1R^2$ moiety is a 5-, 6- or 7-membered saturated, partially saturated or unsaturated ring, which is optionally substituted and which contains 0-2 additional heteroatoms selected from N, O, P(O) and S(O)$_r$; and each of the foregoing alkyl, alkenyl, alkynyl, cycloalkyl, cycloalkenyl, cycloalkynyl, aryl, heteroaryl and heterocyclic moiety is optionally substituted.

2. The compound of claim 1 in which n is 1.

3. The compound of claim 1 in which n is 2.

4. The compound of any of claim 1, 2 or 3 having one of the following formulae:

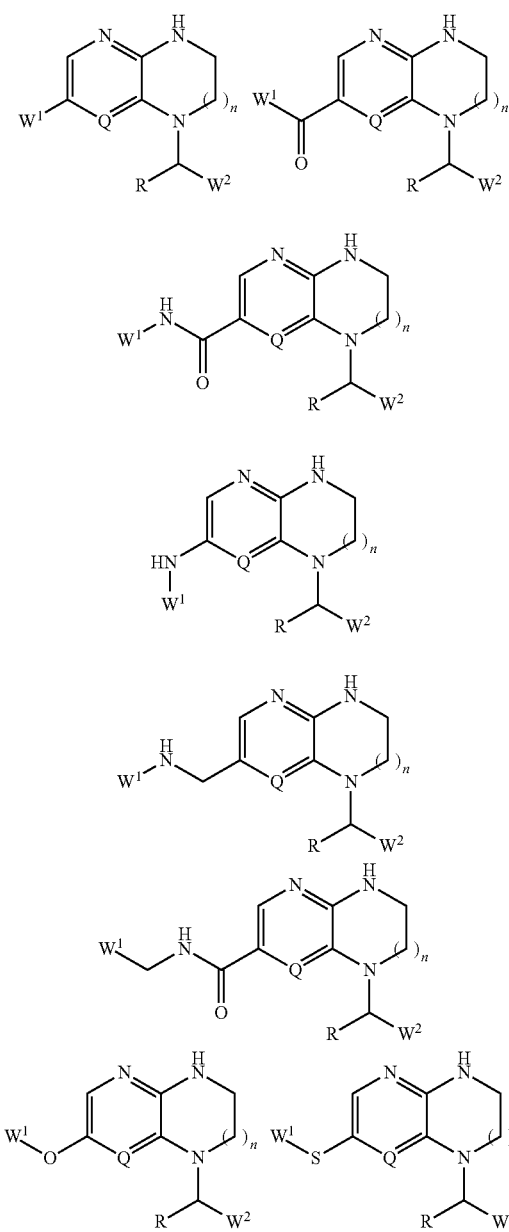

in which R is CH$_3$ or H.

5. The compound of any of claim 1, 2 or 3 having either of the following formulae:

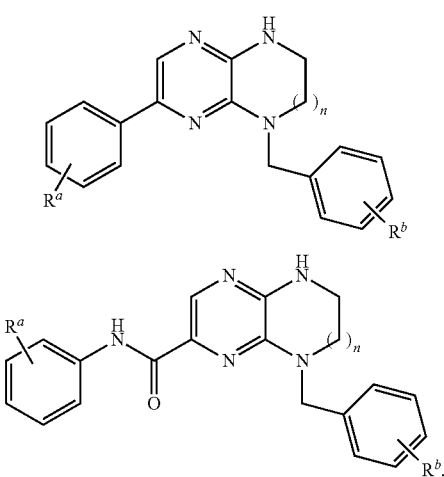

6. The compound of any of claim 1, 2 or 3 having the formula:

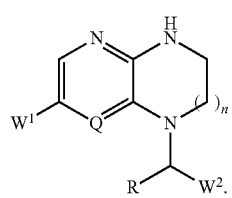

7. The compound of claim 6 in which $W^1$ and $W^2$ are aryl optionally substituted with 1-5 $R^a$ and 1-5 $R^b$ respectively; and R is H.

8. The compound of claim 6 in which $W^1$ is a 5- or 6-membered heteroaryl optionally substituted with 1-5 $R^a$ and $W^2$ is an aryl optionally substituted with 1-5 $R^b$ respectively; and R is H.

9. The compound of any of claims 1 to 3 in which $L^2$ is $C(O)C_{0-6}$alkyl.

10. The compound of claim 9 in which $L^2$ is $C(O)$.

11. The compound of claim 9 in which $L^2$ is $C(O)CH_2$.

12. The compound of claim 9 having one of the following formulae:

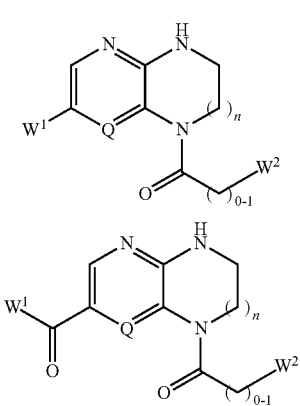

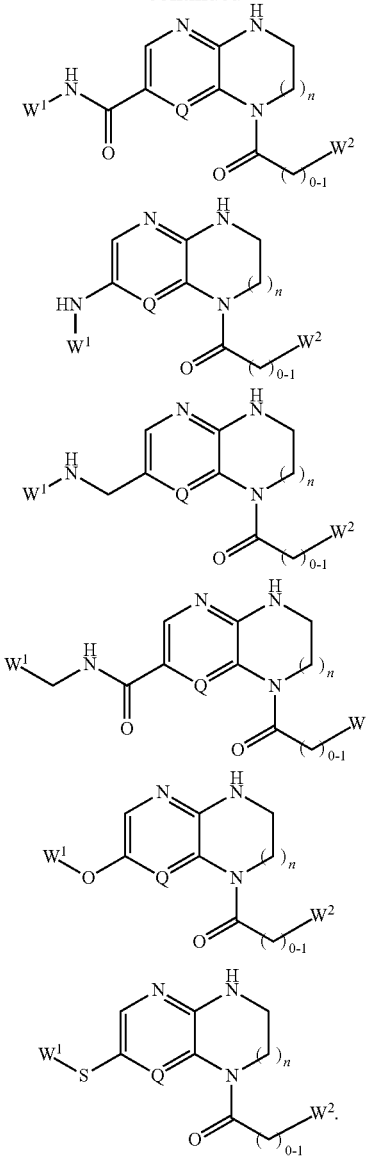

13. The compound of claim 12 in which $W^1$ and $W^2$ are aryl optionally substituted with 1-5 $R^a$ and 1-5 $R^b$ respectively.

14. The compound of claim 12 in which $W^1$ is a 5- or 6-membered heteroaryl optionally substituted with 1-5 $R^a$, $W^2$ is an aryl optionally substituted with 1-5 $R^b$.

15. The compound of claim 12 in which n is 1.

16. The compound of claim 12 in which n is 2.

17. The compound of claim 1 in which $L^1$ is a bond.

18. The compound of claim 2 in which $L^1$ is a bond.

19. The compound of claim 3 in which $L^1$ is a bond.

20. The compound of claim 1 in which $L^1$ is $C(O)C_{0-6}$alkyl.

21. The compound of claim 2 in which $L^1$ is $C(O)C_{0-6}$alkyl.

22. The compound of claim 3 in which $L^1$ is $C(O)C_{0-6}$alkyl.

23. The compound of claim 1 in which $L^1$ is $C(O)NHC_{0-6}$alkyl.

24. The compound of claim 2 in which $L^1$ is $C(O)NHC_{0-6}$alkyl.

25. The compound of claim 3 in which $L^1$ is $C(O)NHC_{0-6}$alkyl.

26. The compound of claim 1 in which $L^2$ is $CH_2$ or $CH(CH_3)$.

27. The compound of claim 2 in which $L^2$ is $CH_2$ or $CH(CH_3)$.

28. The compound of claim 3 in which $L^2$ is $CH_2$ or $CH(CH_3)$.

29. The compound, tautomer or salt of claim 1 selected from the following;
- 1-(2-chloro-3,6-difluorobenzyl)-7-[3-(morpholin-4-yl)phenyl]-1,2,3,4-tetrahydropyrazino[2,3-b]pyrazine;
- 3-[8-(2-chloro-3,6-difluorobenzyl)-5,6,7,8-tetrahydropyrazino[2,3-b]pyrazin-2-yl]-N-[3-(dimethylamino)propyl]benzamide;
- 1-(2-chloro-3,6-difluorobenzyl)-7-{3-[(4-methylpiperazin-1-yl)methyl]phenyl}-1,2,3,4-tetrahydropyrazino[2,3-b]pyrazine;
- 1-(2-chloro-3,6-difluorobenzyl)-7-[2-(piperazin-1-yl)pyrimidin-5-yl]-1,2,3,4-tetrahydropyrazino[2,3-b]pyrazine;
- {4-[8-(2-chloro-3,6-difluorobenzyl)-5,6,7,8-tetrahydropyrazino[2,3-b]pyrazin-2-yl]phenyl}(4-methylpiperazin-1-yl)methanone;
- 1-(2-chloro-3,6-difluorobenzyl)-7-[3-(morpholin-4-ylmethyl)phenyl]-1,2,3,4-tetrahydropyrazino[2,3-b]pyrazine;
- 1-(2-chloro-3,6-difluorobenzyl)-7-[4-(morpholin-4-ylmethyl)phenyl]-1,2,3,4-tetrahydropyrazino[2,3-b]pyrazine;
- 1-(2-chloro-3,6-difluorobenzyl)-7-{1-[2-(morpholin-4-yl)ethyl]-1H-pyrazol-4-yl}-1,2,3,4-tetrahydropyrazino[2,3-b]pyrazine;
- 3-{4-[8-(2-chloro-3,6-difluorobenzyl)-5,6,7,8-tetrahydropyrazino[2,3-b]pyrazin-2-yl]phenyl}propanehydrazide;
- 1-(2,5-dichlorobenzyl)-7-[6-(4-methylpiperazin-1-yl)pyridin-3-yl]-1,2,3,4-tetrahydropyrazino[2,3-b]pyrazine;
- {3-[8-(2-chloro-3,6-difluorobenzyl)-5,6,7,8-tetrahydropyrazino[2,3-b]pyrazin-2-yl]phenyl}(4-methylpiperazin-1-yl)methanone;
- 4-[8-(2-chloro-3,6-difluorobenzyl)-5,6,7,8-tetrahydropyrazino[2,3-b]pyrazin-2-yl]-N-[2-(morpholin-4-yl)ethyl]benzamide;
- {4-[8-(2-chloro-3,6-difluorobenzyl)-5,6,7,8-tetrahydropyrazino[2,3-b]pyrazin-2-yl]phenyl}[4-(pyrrolidin-1-yl)piperidin-1-yl]methanone;
- 2-{3-[8-(2-chloro-3,6-difluorobenzyl)-5,6,7,8-tetrahydropyrazino[2,3-b]pyrazin-2-yl]phenyl}acetamide;
- 1-(2-chloro-3,6-difluorobenzyl)-7-[2-(4-methylpiperazin-1-yl)pyridine-4-yl]-1,2,3,4-tetrahydropyrazino[2,3-b]pyrazine;
- 1-(2-chloro-3,6-difluorobenzyl)-7-[1-(piperidin-4-yl)-1H-pyrazol-3-yl]-1,2,3,4-tetrahydropyrazino[2,3-b]pyrazine
- 4-[8-(2-chloro-3,6-difluorobenzyl)-5,6,7,8-tetrahydropyrazino[2,3-b]pyrazin-2-yl]-N-[3-(dimethylamino)propyl]benzamide;
- 4-[8-(2-chloro-3,6-difluorobenzyl)-5,6,7,8-tetrahydropyrazino[2,3-b]pyrazin-2-yl]-N-[2-(diethylamino)ethyl]benzamide;
- {4-[8-(2-chloro-3,6-difluorobenzyl)-5,6,7,8-tetrahydropyrazino[2,3-b]pyrazin-2-yl]phenyl}[(2R)-2-(pyrrolidin-1-ylmethyl)pyrrolidin-1-yl]methanone;
- 1-(2,6-dichlorobenzyl)-7-[2-(4-methylpiperazin-1-yl)pyridin-4-yl]-1,2,3,4-tetrahydropyrazino[2,3-b]pyrazine;
- 1-(2,5-difluorobenzyl)-7-[2-(4-methylpiperazin-1-yl)pyridin-4-yl]-1,2,3,4-tetrahydropyrazino[2,3-b]pyrazine;
- 1-[5-chloro-2-(trifluoromethyl)benzyl]-7-[2-(4-methylpiperazin-1-yl)pyridin-4-yl]-1,2,3,4-tetrahydropyrazino[2,3-b]pyrazine;
- 9-(2-chloro-3,6-difluorobenzyl)-2-[3-(morpholin-4-yl)phenyl]-6,7,8,9-tetrahydro-5H-pyrazino[2,3-b][1,4]diazepine;
- 3-[9-(2-chloro-3,6-difluorobenzyl)-6,7,8,9-tetrahydro-5H-pyrazino[2,3-b][1,4]diazepin-2-yl]-N-[2-(morpholin-4-yl)ethyl]benzamide;
- {3-[9-(2-chloro-3,6-difluorobenzyl)-6,7,8,9-tetrahydro-5H-pyrazino[2,3-b][1,4]diazepin-2-yl]phenyl}[4-(2-hydroxyethyl)piperazin-1-yl]methanone;
- 9-(2-chloro-3,6-difluorobenzyl)-2-(2-methyl-1,2,3,4-tetrahydroisoquinolin-6-yl)-6,7,8,9-tetrahydro-5H-pyrazino[2,3-b][1,4]diazepine;
- 6-[9-(2-chloro-3,6-difluorobenzyl)-6,7,8,9-tetrahydro-5H-pyrazino[2,3-b][1,4]diazepin-2-yl]-N-methylquinazolin-2-amine; and,
- 9-(2-chloro-3,6-difluorobenzyl)-2-{-4-[2-(1H-imidazol-1-yl)ethoxy]phenyl}-6,7,8,9-tetrahydro-5H-pyrazino[2,3-b][1,4]diazepine.

30. The compound of any of claim 1 to 3 or 17-25 in which $W^1$ is aryl.

31. The compound of any of claim 1 to 3 or 17-25 in which $W^1$ is 5- or 6-membered heteroaryl.

32. The compound of any of claim 1 to 3 or 17-25 in which $W^1$ is a 5-, 6- or 7-membered heterocyclyl.

33. The compound of any of claim 1 to 3 or 17-25 in which $W^1$ is a 3- to 8-membered carbocyclyl.

34. A composition comprising a compound of any of claim 1-3, 30-33, 4-6, 7-14, 15-16, or 17-29; or a pharmaceutically acceptable salt thereof and a pharmaceutical carrier, diluent or vehicle.

* * * * *